(12) United States Patent
Bennett et al.

(10) Patent No.: US 9,707,201 B2
(45) Date of Patent: Jul. 18, 2017

(54) ALLIUM EXTRACTS

(71) Applicant: Leptrex Ltd, Hythe Kent (GB)

(72) Inventors: Norman John Bennett, Hythe Kent (GB); Edward Dalhousie Ramsey, Hythe Kent (GB)

(*) Notice: Subject to any disclaimer, the term of this patent is extended or adjusted under 35 U.S.C. 154(b) by 0 days.

(21) Appl. No.: 14/905,220

(22) PCT Filed: Jan. 10, 2014

(86) PCT No.: PCT/GB2014/050060
§ 371 (c)(1),
(2) Date: Jan. 14, 2016

(87) PCT Pub. No.: WO2015/008019
PCT Pub. Date: Jan. 22, 2015

(65) Prior Publication Data
US 2016/0151324 A1 Jun. 2, 2016

(30) Foreign Application Priority Data

Jul. 15, 2013 (WO) ..................... PCT/GB13/51892

(51) Int. Cl.
| | | |
|---|---|---|
| *A61K 31/10* | (2006.01) | |
| *A61K 31/255* | (2006.01) | |
| *A61K 36/8962* | (2006.01) | |
| *C12P 11/00* | (2006.01) | |

(52) U.S. Cl.
CPC ........ *A61K 31/255* (2013.01); *A61K 36/8962* (2013.01); *C12P 11/00* (2013.01)

(58) Field of Classification Search
USPC ........................................ 514/706, 708, 517
See application file for complete search history.

(56) References Cited

PUBLICATIONS

Keusgen; Journal of Agricultural and Food Chemistry, vol. 50(10), 2002, pp. 2884-2890.*
Benkeblia (Food 1(2) 193-201, 2007, Global Science Books).*
Gnan (Journal of Ethnopharmacology, 68, 1999, 103-108).*
Kwon (Bioscience, biotechnology, and biochemistry, 65(4), 966-968, 2001).*
Sigma (http://www.sigmaaldrich.com/catalog/product/sial/nist2897a?lang=en&region=US; Ethanol solution, downloaded on Sep. 22, 2016).*

* cited by examiner

*Primary Examiner* — Pancham Bakshi
(74) *Attorney, Agent, or Firm* — Wood, Phillips, Katz, Clark & Mortimer

(57) ABSTRACT

Improvements in or relating to *Allium* extracts. In particular, improvements in or relating to extending the therapeutic half-life or duration of *Allium* extracts. The invention further relates to the synthesis of methyl methyl thiosulfinate in a mixture with varying molar or mass ratios depending on the reaction conditions, in particular from either methiin or alliin alone or a mixture of both. Methods of treatment methicillin-resistant *Staphylococcus aureus* are also provided. Also provided is a kit comprising methiin in a first container and alliin in a second container.

7 Claims, 69 Drawing Sheets

ALLIUM EXTRACTS

FIELD OF THE INVENTION

The present invention relates to improvements in or relating to *Allium* extracts. In particular, it relates to improvements in or relating to extending the therapeutic half-life or duration of *Allium* extracts. The invention also relates to the synthesis of certain thiosulfinate compounds, especially to the synthesis of methyl allyl thiosulfinate and allyl methyl thiosulfinate, in particular from either methiin or alliin alone or a mixture of both. The invention further relates to the synthesis of methyl allyl thiosulfinate, allyl methyl thiosulfinate, allicin, and methyl methyl thiosulfinate in a mixture with varying molar or mass ratios depending on the reaction conditions, in particular from either methiin or alliin alone or a mixture of both. A high yielding, optimized synthesis of allicin starts from alliin, whereas methyl methyl thiosulfinate is advantageously obtained from methiin. Also provided is a kit comprising methiin in a first container and/or alliin in a second container and an allinase source, in particular garlic powder in a third container. Finally, the invention provides a method of preparing a mixture of methyl allyl thiosulfinate, allyl methyl thiosulfinate, allyl allyl thiosulfinate (allicin) and methyl methyl thiosulfinate from methiin and pieces of an *Allium* species.

BACKGROUND OF THE INVENTION

The present invention relates to improvements in or relating to *Allium* extracts. In particular, it relates to improvements in or relating to extending the therapeutic half-life or duration of *Allium* extracts. We describe a method of preparing an *Allium* species extract, the process comprising the steps of preparing a preparation of chopped, minced, ground or crushed cloves of an *Allium* species; allowing the preparation to stand for a first predetermined period at a first temperature; mixing with water at a second temperature for a second predetermined period; freezing the *Allium*/water mixture; maintaining the *Allium*/water mixture in a frozen state for a third predetermined period of time; allowing the *Allium*/water mixture to thaw at a third temperature; and removing solid material from the mixture to leave an aqueous *Allium* extract. We also describe a method of enhancing the methyl allyl-thiosulfinate and/or allyl methyl-thiosulfinate content of an aqueous *Allium* extract; the method comprising freezing the extract; allowing the frozen extract to begin to thaw; and collecting the liquid produced before thawing is complete; a method of enhancing the methyl allyl-thiosulfinate and/or allyl methyl-thiosulfinate content of an *Allium* species extract, the method comprising preparing a preparation of chopped, minced, ground or crushed cloves in an *Allium* species; adding methiin or a source of methiin to the *Allium* species preparation; and a method of extending the shelf-life or the bioactivity duration of an *Allium* species extract; the method comprising increasing a methyl allyl-thiosulfinate and/or allyl methyl-thiosulfinate content of the extract. We also describe an *Allium* species extract comprising allicin and at least one of methyl allyl-thiosulfinate and allyl methyl-thiosulfinate wherein the methyl allyl-thiosulfinate and allyl methyl-thiosulfinate is present in a combined amount of 17.5 wt % or more based on the combined amount of allicin, methyl allyl-thiosulfinate and allyl methyl-thiosulfinate, preferably 30 wt % or more.

S-Alk(enyl)-cysteine sulfoxides are widely distributed throughout the species in the genus *Allium*. Common examples of edible species that help form the approximate 700 species that belong to the genus *Allium* include: shallot (*A. asacalonicum* aust.), scallion (*A. fitstulosum* L.), leek (*A. porrum* L.), garlic (*A. sativum* L.), onion (*A. cepa* L.), chive (*A. schoenoprasum* L.), wild garlic (*A. ursinum* L.), Welsh onion (*A. fistulosum* L.), and Chinese chives (*A. tuberosum* L.).

Common to all *Allium* species is the enzyme allinase which catalyses the hydrolysis of S-alk(en)yl-L-cysteine sulfoxides (SACSs) in the presence of the cofactor pyridoxal 5'-phosphate to produce pyruvate, ammonia and sulfenic acids. In intact *Allium* species tissues, allinase is separately compartmentalized within plant vacuoles and the representative SACSs are located in the cytoplasm. Once *Allium* species tissue is damaged, the contents of the vacuole and cytoplasm mix, resulting in allinase being able to act on SACSs in a hydrolysis reaction leading to the formation of highly reactive sulfenic acids.

The sulfenic acids once formed, typically react with each other rapidly eliminating water in a condensation reaction that results in the synthesis of mixtures of thiosulfinates. The general reaction scheme showing the allinase-mediated hydrolysis of SACSs leading to the formation of sulfenic acids that can undergo condensation reaction with one another to form thiosulfinates is given in Scheme 1:

Scheme 1. Formation of *Allium* species thiosulfinates. (i) Initial production of sulfenic acids by the action of allinase on various S-Alk(en)yl cysteine sulfoxides. Followed by (ii) Sulfenic acids undergoing rapid condensation reaction to produce thoisulfinates.

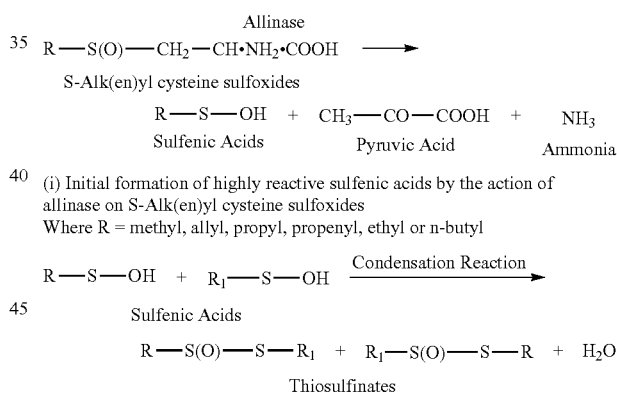

(i) Initial formation of highly reactive sulfenic acids by the action of allinase on S-Alk(en)yl cysteine sulfoxides
Where R = methyl, allyl, propyl, propenyl, ethyl or n-butyl (ii) Two molecules of sulfenic acids formed from reaction (i) above, undergoing condensation reaction to produce thiosulinates.
Where R and $R_1$ = methyl, allyl, propyl, propenyl, ethyl or n-butyl
If R = $R_1$ then a symmetrical thiosulfinate is produced. If R and $R_1$ are different alk(en)yl groups then an asymmetrical thiosulfinate is produced.

According to a comprehensive review article, [P. Rose, M. Whiteman, P. K. Moore and Y. Z. Zhu, *Natural Product Reports*, (2005), 22, pp. 351-368] concerning the biosynthesis, bioactivity and chemistry of SACSs, to date four major and two minor SACSs have been identified in the genus *Allium* and from these six SACSs approximately fifty additional sulfur containing compounds can be generated. The structures of the six SACSs commonly found in *Allium* species are given in Table 1:

TABLE 1

Structures of six of the most common S-Alk(en)yl cysteine sulfoxides found in the genus *Allium*.

| Common Name | Chemical Name | Chemical Structure |
|---|---|---|
| Methiin | (+)-S-Methyl-L-cysteine sulfoxide | $H_3C-S(O)-CH_2-CH(NH_2)-COOH$ |
| Ethiin | (+)-S-Ethyl-L-cysteine sulfoxide | $H_3C-CH_2-S(O)-CH_2-CH(NH_2)-COOH$ |
| Alliin | (+)-S-Allyl-L-cysteine sulfoxide | $H_2C=CH-CH_2-S(O)-CH_2-CH(NH_2)-COOH$ |
| Isoalliin | (+)-S-Propenyl-L-cysteine sulfoxide | $H_3C-CH=CH-S(O)-CH_2-CH(NH_2)-COOH$ |
| Propiin | (+)-S-Propyl-L-cysteine sulfoxide | $H_3C-CH_2-CH_2-S(O)-CH_2-CH(NH_2)-COOH$ |
| Butiin | (+)-S-n-Butyl-L-cysteine sulfoxide | $H_3C-CH_2-CH_2-CH_2-S(O)-CH_2-CH(NH_2)-COOH$ |

Condensation of two molecules of sulfenic acids gives rise to the formation of one thiosulfinate molecule (general formula $RS(O)SR_1$ where R and $R_1$ are alkyl and/or alkenyl groups). The thiosulfinates thus formed can be divided into two groups: (1) symmetrical thiosulfinates formed by the condensation of two molecules of sulfenic acid each with the same alk(en)yl substituent group $R=R_1$ or (2) asymmetrical thiosulfinates generated from two different molecules of sulfenic acid each with a different alk(en)yl substituent ($R \neq R_1$). Thus, the thiosulfinate allicin [$CH_2CH=CH_2S(O)SCH_2CH=CH_2$, whose structure can be represented as AllS(O)SAll where All represents an allyl substituent] is a symmetrical thiosulfinate since $R=R_1=-CH_2CH=CH_2$.

Since the six SACSs shown in Table 1 produce six different sulfenic acids due to hydrolysis brought about by allinase then numerous thiosulfinates can be produced. The structures of commonly produced thiosulfinates brought about by condensation reaction between the sulfenic acids that *Allium* species commonly produce have been identified [C. Shen, H. Xiao and K. L. Parkin, *Journal of Agricultural and Food Chemistry*, (2002), 50, pp. 2644-2651] and include those structures given in Table 2:

TABLE 2

Structures of symmetric and examples of asymmetric thiosulfinates produced by the species in the genus *Allium*. Some thiosulfinates that contain a propenyl group (—CH=CH—CH₃) also exist in the form of E,Z-geometric isomers.

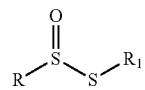

| Alk(en)yl Groups In Symmetrical Thiosulfinates | Thiosulfinate $RS(O)SR_1$ Alk(en)yl Groups In Asymmetrical Thiosulfinates | |
|---|---|---|
| $R = R_1 = -CH_3$ | $R = -CH_3$ | with $R_1 = -CH_2-CH=CH_2$ |
| $-CH_2-CH_3$ | $R = -CH_3$ | with $R_1 = -CH_2-CH_2-CH_3$ |
| $-CH_2-CH_2-CH_3$ | $R = -CH_3$ | with $R_1 = -CH=CH-CH_3$ |
| $-CH_2-CH=CH_2$ | $R = -CH_2-CH=CH_2$ | with $R_1 = -CH_3$ |
| $-CH=CH-CH_3$ | $R = -CH_2-CH=CH_2$ | with $R_1 = -CH_2-CH=CH_2$ |
| $-CH_2-CH_2-CH_2-CH_3$ | $R = -CH_2-CH=CH_2$ | with $R_1 = -CH=CH-CH_3$ |
| | $R = -CH_2-CH_2-CH_3$ | with $R_1 = -CH_3$ |
| | $R = -CH_2-CH_2-CH_3$ | with $R_1 = -CH=CH-CH_3$ |
| | $R = -CH=CH-CH_3$ | with $R_1 = -CH_3$ |
| | $R = -CH=CH-CH_3$ | with $R_1 = -CH_2-CH_2-CH_3$ |

The pathways of thiosulfinate production have been studied [C. Shen, Z. Hong and K. L. Parkin, *Journal of Agricultural and Food Chemistry*, (2002), 50, pp. 2652-2659; and C. Shen and K. L. Parkin, *Journal of Agricultural and*

*Food Chemistry*, (2000), 48, pp. 6254-6260] stemming from which it has been revealed that the precursor SACSs undergo hydrolysis at different rates. The reported rates of allinase mediated SACSs hydrolysis to form sulfenic acids are: (+)-S-trans-1-propenyl-L-cysteine sulfoxide (isoalliin)>(+)-S-allyl-L-cysteine sulfoxide (alliin)>(+)-propyl-L-cysteine sulfoxide (propiin)>(+)-S-ethyl-L-cysteine sulfoxide (ethiin)>(+)-S-methyl-L-cysteine sulfoxide (methiin). It is also reported that those thiosulfinates more rapidly formed from the SACSs that more rapidly undergo hydrolysis in an allinase mediated reaction can in turn react with the sulfenic acids produced by SACSs that are more slowly hydrolysed by the action allinase.

Allicin is known to have a range of therapeutic effects. However, its half-life is short [H. Fujisawa, K. Suma, K. Origuchi, T. Seki and T. Ariga, *Journal of Agricultural and Food Chemistry*, (2008), 56, pp. 4229-4235; and H. Fujisawa, K. Suma, K. Origuchi, T. Seki and T. Ariga, *Bioscience, Biotechnology and Biochemistry*, (2008), 72, pp. 2877-2883].

Although the vast majority of published scientific literature concerning the therapeutic action of garlic tends to focus on allicin [whose structural formula is: $H_2=CH-CH_2-S(O)-S-CH_2-CH=CH_2$ and whose abbreviation is AllS(O)SAll], there are a limited number of reports that indicate that both allyl methyl-thiosulfinate [whose structural formula is: $CH_3-S(O)-S-CH_2-CH=CH_2$ and whose abbreviation is MeS(O)SAll] and methyl allyl-thiosulfinate [whose structural formula is: $CH_2=CH-CH_2-S(O)-S-CH_3$ and whose abbreviation is AllS(O)SMe], also possess significant therapeutic biological activity. Examples of such reports are: (i) the potency of the antibacterial and antifungicidal activity of AllS(O)SMe tested against a range of gram-positive bacteria, gram-negative bacteria and yeasts has been found to be similar [H. Yoshida, H. Katsuzaki, R. Ohta, K. Ishikawa, H. Fukuda, T. Fujino and A. Suzuki, *Bioscience, Biotechnology and Biochemistry*, (1999), 63, pp. 591-594] to that of allicin; (ii) in vitro virucidal studies concerning compounds present in garlic extracts against a range of selected viruses including herpes simplex virus types 1 and 2, parainfluenza virus type 3 and rhinovirus type 2 have established that allicin, MeS(O)SAll and AllS(O)SMe thiosulfinates all possess virucidal activity; and (iii) that allicin, MeS(O)SAll and AllS(O)SMe all show inhibition [P. Canizares. I. Gracia, L. A. Gomez, C. M. de Argila, D. Boixeda, A. Garcia and L. de Rafael, *Biotechnology Progress*, (2004), pp. 397-401] of the in vitro growth of *Helicobacter pylori*.

Hence, apart from the presence of allicin, it is advantageous for both the MeS(O)SAll and AllS(O)SMe thiosulfinate analogues to be present to support and help compliment the therapeutic activity of allicin in *Allium* species extracts, in particular those extracts derived from garlic. However, Block et al. [J. Agric. Food Chem., (1992), 40, pp. 2418-2430] have reported very significant variation in the quantities of MeS(O)SAll and AllS(O)SMe in extracts derived from different species of garlic obtained from different geographical locations and/or stored under different conditions prior to extraction. Some garlic extracts provide relatively very low concentrations of AllS(O)SMe and MeS(O)SAll. The present invention seeks to address this problem.

In view of allicin's relatively short half-life there is a need to enhance the therapeutic half-life of garlic and other *Allium* species extract compositions to overcome the limitations of the short half-life of allicin. The present inventions seek to provide a solution.

BRIEF SUMMARY OF THE INVENTION

The present invention thus provides
(1) a method of producing an aqueous solution of methyl allyl thiosulfinate and/or allyl methyl thiosulfinate, the method comprising the steps of (i) dissolving alliin and/or methiin in water at a temperature controlled to be within a range of 0° C. to 50° C.; and (ii) contacting the solution with allinase for a predetermined period;
(2) the method according embodiment (1) wherein the source of allinase is an *Allium* species or parts thereof, the parts preferably being the cloves, the *Allium* species preferably being garlic;
(3) the method according to embodiment (2) wherein the garlic is freshly minced garlic;
(4) the method according to embodiment (2) wherein the garlic is garlic powder;
(5) the method according to anyone of embodiments (1) to (4) which produces an aqueous solution additionally containing allyl allyl thiosulfinate (allicin) and/or methyl methyl thiosulfinate;
(6) a kit comprising a container containing methiin and/or a container containing alliin and a container containing an allinase source;
(7) a kit according to embodiment (6) comprising a container containing alliin and a container containing an allinase source;
(8) the use of a kit which comprises
(i) methiin in a first container, alliin in second container, and an allinase source in a third container for producing methyl allyl thiosulfinate and/or allyl methyl thiosulfinate; or
(ii) alliin in a first container and an allinase source in a second container for producing allicin; or
(iii) methiin in a first container and an allinase source in a second container for producing methyl methyl thiosulfinate;
(9) a method of producing a mixture comprising methyl allyl thiosulfinate, allyl methyl thiosulfinate and/or methyl methyl thiosulfinate comprising the steps of
(i) chopping, mincing, grinding and/or crushing cloves of an *Allium* species;
(ii) adding water; and
(iii) adding methiin;
(10) the use of an *Allium* species or parts thereof for producing a compound selected from the group consisting of methyl allyl thiosulfinate, allyl methyl thiosulfinate, allyl allyl thiosulfinate (allicin), and methyl methyl thiosulfinate, preferably selected from the group consisting of methyl allyl thiosulfinate, allyl methyl thiosulfinate, and methyl methyl thiosulfinate;
(11) the use according to embodiment (10) for producing a mixture comprising methyl allyl thiosulfinate, allyl methyl thiosulfinate, allyl allyl thiosulfinate (allicin), and methyl methyl thiosulfinate, preferably comprising methyl allyl thiosulfinate, allyl methyl thiosulfinate, and methyl methyl thiosulfinate;
(12) a method of preparing an *Allium* species extract, the process comprising the steps of preparing a preparation of chopped, minced, ground or crushed cloves of an *Allium* species; allowing the preparation to stand for a first predetermined period at a first temperature; mixing with water at a second temperature for a second predetermined period; freezing the *Allium*/water mixture; maintaining the *Allium*/water mixture in a frozen state for a third predetermined period of time; allowing the *Allium*/water mixture to thaw at a third temperature; and removing solid material from the mixture to leave an aqueous *Allium* extract;
(13) a method of enhancing the methyl allyl-thiosulfinate and/or allyl methyl-thiosulfinate content of an aqueous *Allium* extract; the method comprising freezing the extract;

allowing the frozen extract to begin to thaw; and collecting the liquid produced before thawing is complete;

(14) a method of enhancing the methyl allyl-thiosulfinate and/or allyl methyl-thiosulfinate content of an *Allium* species extract, the method comprising preparing a preparation of chopped, minced, ground or crushed cloves in an *Allium* species; and adding methiin or a source of methiin to the *Allium* species preparation;

(15) a method of extending the shelf-life and/or the bioactivity duration of an *Allium* species extract; the method comprising increasing a methyl allyl-thiosulfinate and/or allyl methyl-thiosulfinate content of the extract;

(16) the method according to anyone of embodiments (12) to (15) wherein the *Allium* species extract is an extract of *Allium Sativum* L;

(17) an *Allium* species extract having an enhanced methyl allyl-thiosulfinate and/or allyl methyl-thiosulfinate content, obtainable by the method of any one of the embodiments (12) to (16);

(18) an *Allium* species extract comprising allicin and at least one of methyl allyl-thiosulfinate and allyl methylthiosulfinate wherein the methyl allyl-thiosulfinate and allyl methyl-thiosulfinate is present in a combined amount of 17.5 wt % or more based on the combined amount of allicin, methyl allyl-thiosulfinate and allyl methyl-thiosulfinate, preferably 30 wt % or more; and

(19) the *Allium* species extract according to embodiment (17) or (18) wherein the *Allium* extract is an extract of *Allium Sativum* L.

Preferably the an *Allium* species extract having an enhanced methyl allyl-thiosulfinate and/or allyl methyl-thiosulfinate content, obtainable by the method of any one of the embodiments (12) to (16) has a content enhanced by at least 10% more preferably at least 50%, even more preferably at least 100% or from 50 to 75 compared to the original methyl allyl-thiosulfinate and/or allyl methyl-thiosulfinate content;

In its broadest sense, the present invention is based on the determination by the present inventors that the methyl allyl-thiosulfinate and allyl methyl-thiosulfinate products have significantly longer half-lives than allicin. Based on this determination products containing allicin can be formulated to provide extended shelf-lives or extended duration therapeutic efficacy. The present inventors have also developed procedures for enhancing the content of MeS(O)SAll and AllS(O)SMe in therapeutic compositions containing *Allium* extracts. It has surprisingly been found that the synthesis of each of methyl allyl thiosulfinate and allyl methyl thiosulfinate or both together in a mixture can be accomplished not only from a mixture of methiin or alliin, but most notably from either methiin or alliin alone when contacted with the enzyme allinase, i.e. subjected as a substrate to the action of that enzyme.

As used herein

Analogue-1 (also briefly dubbed "A-1") collectively refers to a mixture of allyl methyl-thiosulfinate (AM) represented by formula $CH_3—S(O)—S—CH_2—CH=CH_2$ (often abbreviated MeS(O)SAll) and methyl allyl-thiosulfinate (MA) represented by formula $CH_2=CH—CH_2—S(O)—S—CH_3$ (often abbreviated AllS(O)SMe); analogue-1 is herein also referred to as MAAM or MA-AM Analogue-2 (also dubbed "A-2") refers to allyl allyl-thiosulfinate, which is also named allicin and represented by formula $CH_2=CH—CH_2—S(O)—S—CH_2—CH=CH_2$ (often abbreviated as AllS(O)SAll)

Analogue-3 (also dubbed "A-3") collectively refers to both geometric isomers of 1-propenyl-(E,Z) allyl-thiosulfinate represented by formula $CH_2=CH—CH_2—S(O)—S—CH_2=CH—CH_3$ (often abbreviated as AllS(O)SPn-(E,Z))

Analogue-4 (also dubbed "A-4") refers to methyl methyl-thiosulfinate represented by formula $CH_3—S(O)—S—CH_3$ (often abbreviated as MeS(O)SMe or MMTSO).

In one aspect, the present invention provides a method of preparing an *Allium* extract. The process comprises the steps of chopping cloves of an *Allium* species; allowing the chopped cloves to stand for a first predetermined period at a first temperature; mixing with water at a second temperature for a second predetermined period; freezing the *Allium*/water mixture; maintaining the *Allium*/water mixture in a frozen state for a third predetermined period of time; allowing the *Allium*/water mixture to thaw at a third temperature; and removing solid material from the mixture to leave an aqueous *Allium* extract.

Advantageously, the process further comprises the step of freezing the aqueous *Allium* extract at a fourth temperature until ice formation is complete; allowing the frozen extract to begin to thaw collecting the liquid so obtained. Liquid collection is stopped before the frozen extract has completely thawed.

Advantageously, the first predetermined period is from 3 to 30 minutes, preferably 5 to 20 minutes, more preferably 10 to 15 minutes, particularly about 15 minutes.

Advantageously, the second predetermined period is 3 to 10 minutes, preferably about 5 minutes.

Advantageously, the third predetermined period of time is less than about 48 hours, preferably from 8 to 36 hours, more preferably from 12 to 24 hours.

Preferably, the water mixture is frozen for fractional freeze concentration of the mixture, suitably at a temperature of −10° C. to −30° C., more preferably at a temperature of about −20° C.

Preferably, the fourth predetermined period is from 12 to 36 hours, more preferably about 24 hours. Alternatively the predetermined period is less than 24 hours and more than 12 hours, for example from 14 to 20 hours.

Advantageously, the first temperature is from 10° C. to 30° C., preferably 15-25° C., more preferably about 20° C.

Advantageously, the second temperature is less than 10° C., more preferably less than about 6° C., suitably about 4° C.

Advantageously, the third temperature is between 5° C. and 15° C., preferably about 10° C.

Advantageously, the fourth temperature is −10° C. to −30° C., preferably about −20° C.

Preferably, the chopped/minced cloves and water are mixed in a ratio 0.5:1 (w/v) to 3:1 (w/v), more preferably 0.5:1 (w/v) to 2:1 (w/v), even more preferably 0.6:1 (w/v).

In a second aspect, the present invention provides a method of enhancing the methyl allyl-thiosulfinate and/or allyl methyl-thiosulfinate content of an aqueous *Allium* extract; the method comprising freezing the extract; allowing the frozen extract to begin to thaw; and collecting the liquid produced, stopping collection before the extract has completely thawed.

In an alternative embodiment, the *Allium* extract composition is improved by addition of isolated semi purified or synthetic methyl allyl-thiosulfinate and/or allyl methyl-thiosulfinate.

In a third aspect, the present invention comprises an *Allium* species extract having an enhanced methyl allyl-thiosulfinate and/or allyl methyl-thiosulfinate content, obtainable by the method described above.

Preferably the an *Allium* species extract having an enhanced methyl allyl-thiosulfinate and/or allyl methyl-thiosulfinate content, obtainable by the method of any one of the embodiments (12) to (16) has a content enhanced by at least 10% more preferably at least 50%, even more preferably at least 100% or from 50 to 75% compared to the original methyl allyl-thiosulfinate and/or allyl methyl-thiosulfinate content;

In a fourth aspect, the present invention provides an *Allium* species extract comprising allicin and methyl allyl-thiosulfinate and/or allyl methyl-thiosulfinate wherein the methyl allyl-thiosulfinate and/or allyl methyl-thiosulfinate is present in a combined amount of 17.5 wt % or more based on the combined amount of allicin, methyl allyl-thiosulfinate and allyl methyl-thiosulfinate; preferably 30 wt % or more.

In the fifth aspect, the present invention provides a method of extending the shelf-life or bioactivity duration of an *Allium* species extract, the method comprising increasing a methyl allyl-thiosulfinate and/or allyl methyl-thiosulfinate content of the extract.

Advantageously, the *Allium* species extract is an extract of *Allium Sativum* L.

In a modification, powdered *Allium* species is also added typically during the initial preparation of the *Allium*/water mixture.

The present invention also seeks to provide a synthetically-enhanced route to the MA and AM analogues.

Accordingly, in a sixth aspect, the present invention provides a method of producing an aqueous solution of methyl allyl thiosulfinate and allyl methyl thiosulfinate, the method comprising the steps of (i) dissolving alliin and/or methiin in water at a temperature controlled to be within a range of 0° C. to 50° C.; and (ii) contacting the solution with allinase for a predetermined period.

Preferably, the temperature range is between 10° C. and 40° C.

Preferably, the source of allinase is garlic, more preferably freshly minced garlic.

Preferably, the garlic is added in an amount of from 5 wt % to 200 wt % based on the amount of alliin.

Typically, the predetermined period is 5 to 20 minutes; more typically about 10 minutes.

Preferably, HPLC assay is used to determine completion of the reaction.

Preferably, the process further comprises the step, upon completion of the reaction, of dilution of the solution with water at a temperature of between 0° C. and 10° C., preferably about 4° C.

Preferably, water is added to provide a 5-20 times dilution, more preferably about 10 times dilution.

Preferably, the method further comprises the steps of filtration and storage at a temperature of 0° C. or less, more preferably about –20° C.

In one embodiment of the sixth aspect of the invention, alliin and methiin are dissolved in the water in substantially equimolar amounts. Preferably, there is a slight molar excess of methiin over alliin.

In a second embodiment of the sixth aspect of the invention, there is a molar excess of alliin over methiin.

Suitably the molar excess is about 2 moles of alliin to 1 mole of methiin.

In accordance with the second embodiment of the sixth aspect of the invention, the method produces an aqueous solution of methyl allyl thiosulfinate, allyl methyl thiosulfinate and allicin.

According to a seventh aspect of the invention there is provided a method of producing an aqueous solution of methyl methyl-thiosulfinate comprising the steps of (i) dissolving methiin in water and (ii) contacting the solution with a powdered source of allinase for a predetermined time. Preferably the powdered source of allinase is garlic powder.

Use of garlic powder offers numerous advantages when compared to use of fresh garlic, as set out below:

1. To wash, peel, and chop/mince fresh garlic are labour intensive processes.

2. Freshly chopped/minced garlic tissue produces a pungent odour that causes irritation to the eyes and lingers in the preparation area. The preparation area must be equipped with ventilation equipment/extraction hoods to facilitate the preparation of fresh garlic that is either chopped or minced.

3. Many potential sub-contractors despite having the space, manpower and facilities to prepare freshly chopped/minced garlic decline to do so on the basis that the odour is offensive and may taint other products that they prepare.

4. Once chopped/minced fresh garlic bulb tissue is prepared it must be used very quickly—since without extraction/dilution the rapid build up in allicin concentration in damaged fresh garlic tissue (or other *Allium* Species tissue) denatures allinase.

5. The quality of fresh garlic is seasonally and geographically variable. For example, early season garlic from Shandong Province typically produces a higher relative A-1 content to A-2 content with a low A-3 content. In contrast Autumn season garlic from Shandong Province provides highest A-2 content and high A-3 content.

6. Garlic powder is in effect purchased as a: cheap, highly stable pre-prepared source of dehydrated allinase. It has a very long-shelf life and can be weighed and used as required. It is compact to store.

7. Commercially available garlic powder is derived from very large batch sizes of essentially uniform composition whose manufacture is traceable. From an incoming Quality Assurance perspective garlic powder is ideal—only one assay is required to assess allinase content, microbial contamination etc.

8. For the reasons given in point 5, processes involving garlic powder to provide allinase vastly serve to promote process reproducibility.

9. The use of garlic powder eliminates labour intensive fresh garlic preparation stages (washing, peeling and chopping/mincing) and massively reduces the problems associated with garlic odour and eye irritation.

10. Garlic powder when hydrated provides no/virtually no A-3 species. The inventors have noted that liquids prepared from fresh garlic that provide a significant quantity of A-3 tend to go green in colour rather than remaining a stable yellow or a stable pineapple colour. This is especially the case for those liquids prepared from late season Shandong Province garlic crops.

11. According to the R&D work disclosed herein approximately 3 g of garlic powder provides the same allinase activity of 6 g chopped/minced fresh garlic bulb.

12. Once hydrated, garlic powder is easily and reproducibly blended into an aqueous medium. In contrast homogenized fresh garlic tissue provides a very wide distribution of particle sizes and shapes (therefore contact surface area) that can significantly influence process reproducibility.

13. Unlike processes requiring a freezing stage—slurries made from garlic powder are not frozen since the finely ground garlic powder provides a large heavily damaged area of garlic tissue when hydrated.

14. At the end of the alliin and/or methiin reaction period with contacting allinase derived from garlic powder, it is still relatively convenient to filter away the swollen hydrated garlic powder.

15. In terms of providing kits to customers—the supply of garlic powder that will provide the correct level of allinase activity along with powdered/granules of dry alliin and/or methiin is an ideal way to reduce transport costs to customers rather than shipping large volumes of pre-prepared liquids.

16. The concentrations of A-4, A-2 and A-1 provided in kits prepared from garlic powder of the correct specification and alliin and/or methiin can be easily adjusted by mixing in the appropriate volume of water to prepare liquids of many different types of compositions and strengths. The concentrations of A-4, A-2 and A-1 in liquids prepared using such kits is easy for the customer to prepare.

In contrast kits cannot be supplied with fresh garlic tissue—International Regulations do not permit the free transport of either live vegetable/herbal tissue or their seeds.

End user prepared kits in which the customer will provide fresh garlic bulb as a source of allinase has all the drawbacks of preparing fresh garlic but is especially vulnerable to the age, season and specific type of garlic used. Kits prepared from supplied quantities of dry alliin and or methiin when made up by the customer using water and fresh garlic bulb tissue (or other fresh *Allium* species tissue) will potentially provide liquids of widely varying A-4, A-1 and A-2 composition compared with binary powder kits provided that provide garlic powder and are tested before release.

17. Kits providing separate sources of alliin and/or methiin and garlic powder have long shelf-lives even if stored at ambient temperatures and can be made up by the simple addition of water and mixing as and when the end-user requires. This feature of supplying the correct grade garlic powder to be contacted with different controlled concentrations of alliin and/or methiin in water to provide the end user with liquids with different concentrations of A-4, A-2 and A-1 is considered to be commercially very attractive and has potential to provide completely new, compact, long shelf-life type of product to the diverse market place for such products.

In the method of the seventh aspect of the invention the aqueous solution of step (i) is preferably prepared prior to the addition of garlic powder in step (ii).

In the method, preferably methiin is synthetic, preferably semi-synthetic and most preferably fully synthetic.

In the method, preferably methiin is the only Cysteine sulfoxide, preferably the only sulfoxide dissolved in the water to form the solution. This produces a solution high in methyl methyl-thiosulfinate (MMTSO) concentration, which is shown to have useful properties, such as a very high shelf-life relative to both allicin and MA-AM.

The method may include the step (ia) of also dissolving alliin in the water to form the solution. This produces a solution with a high concentration of MA-AM, in addition to MMTSO.

Preferably, the alliin is synthetic, preferably semi-synthetic or most preferably fully synthetic.

Preferably the water is at a temperature controlled to be within a range of 0° C. to 50° C. for producing a solution of methyl allyl-thiosulfinate and/or allyl methyl-thiosulfinate.

In an eighth aspect of the invention there is provided a method of producing an aqueous solution of methyl allyl-thiosulfinate and/or allyl methyl-thiosulfinate comprising the steps of (i) dissolving methiin and alliin in water and (ii) contacting the solution with freshly minced garlic as a source of allinase for a predetermined time. This method produces a liquid containing MA-AM, Allicin and MMTSO, which all have useful properties, and in particular is characterized by the production of MMTSO which has a particularly long half-life.

Preferably the alliin and methiin are synthetic, preferably semi-synthetic and more preferably fully synthetic.

Preferably the water is at a temperature controlled to be within a range of 0° C. to 50° C.

In a ninth aspect of the invention, there is provided an aqueous solution of methyl methyl-thiosulfinate for use as an antimicrobial agent against methicillin-resistant *staphylococcus aureus* (MRSA). Allicin has previously been used against MRSA, but it is surprising that MMTSO is as effective as Allicin, and also has a longer half-life making it more stable.

Preferably the aqueous solution of methyl methyl-thiosulfinate according to claim 10 has a concentration of greater than 100 ppm.

More preferably the concentration is greater than 200 ppm; even more preferably the concentration is greater than 500 ppm; yet more preferably the concentration is greater than 1000 ppm and most preferably the concentration is greater than 2000 ppm. Ranges between these limits are also preferred. Using the methods disclosed, the relative concentration of A1, A2 and A4 can be balanced depending on the amount of methiin and alliin introduced and the time that the solution is mixed for. Ranges of MMTSO from 100-2000 are preferable, 500-1000 is more preferable, especially when the solution also contains MAAM and Allicin. The same preferred ranges apply to Allicin and MAAM concentrations.

An aqueous alcoholic, preferably aqueous ethanolic, solution as set out above is also provided. This may be useful in a hospital environment as a hand gel or rub.

Preferably the aqueous solution of MMTSO is manufactured by the process of the $7^{th}$ or $8^{th}$ aspect of the invention The invention also provide use of an aqueous solution of methyl methyl-thiosulfinate according to any of the preceding claims against methicillin-resistant *Staphylococcus aureus* and a pharmaceutical composition comprising methyl methyl-thiosulfinate as an active ingredient, preferably the only active ingredient.

Preferably methyl methyl-thiosulfinate is the only active thiosulfinate in the pharmaceutical composition. Preferably the pharmaceutical composition is for treatment of methicillin-resistant *Staphylococcus aureus*.

In a tenth aspect of the invention, there is provided a kit of parts for use in the methods set out above; the kit comprising a container containing methiin and a container containing garlic powder.

Preferably the kit further comprises a container containing alliin.

In an eleventh aspect of the invention, there is provided a kit of parts for use in the methods set out above; the kit comprising a container containing methiin and a container containing alliin.

In either the tenth or eleventh aspects, preferably wherein ratio of the amount of components in the containers is predetermined to produce a predetermined quantity of a thiosulfinate.

More preferably the kits comprise instructions concerning the amount of water to add to the components to carry out the methods set out above.

In either the methods or the kits, preferably the weight ratio of garlic powder to methiin is from 200:1 to 1:1; preferably from 80:1 to 1:1, and most preferably from 40:1 to 1:1. Similarly where both alliin and methiin are provided in the kits or the methods it is preferred that the weight ratio of methiin to alliin is 1:0 to 4:1, preferably from 1:0 to 2:1.

BRIEF DESCRIPTION OF THE DRAWINGS

The above and other aspects of the invention will now be described in further detail by way of example only, with reference to the following examples and the accompanying drawings, in which.

Figure 23:
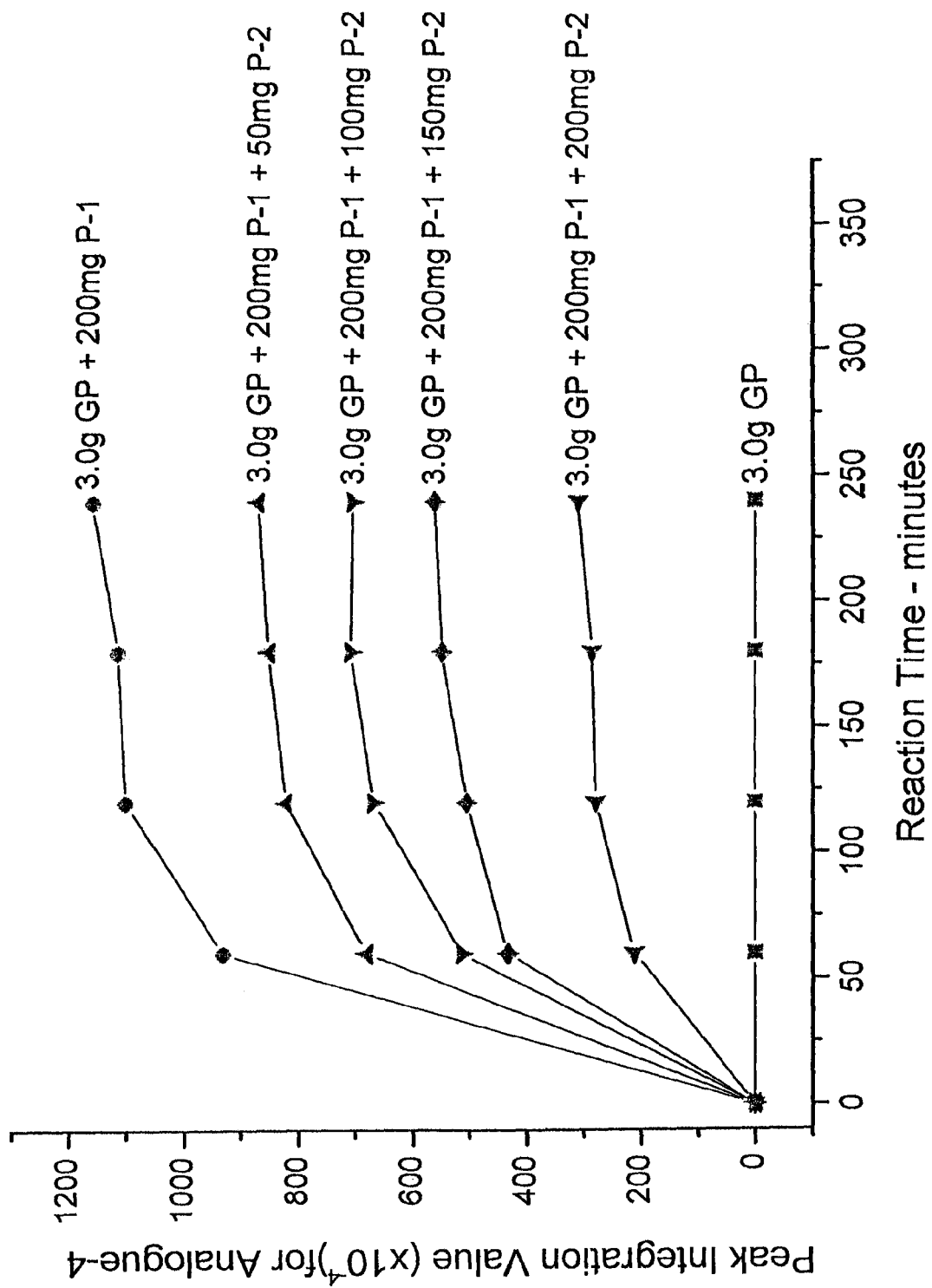

FIG. 23 shows the rate of production for Analogue-4 (retention time approx. 2.5 minutes) for various solutions contacted with 3.0 g GP, each of the ×6 aqueous solutions having different total concentrations of Precursor-1 (P-1) and Precursor-2 (P-2); rate of production of Analogue-4 (retention time approx. 2.5 min).

Figure 24:
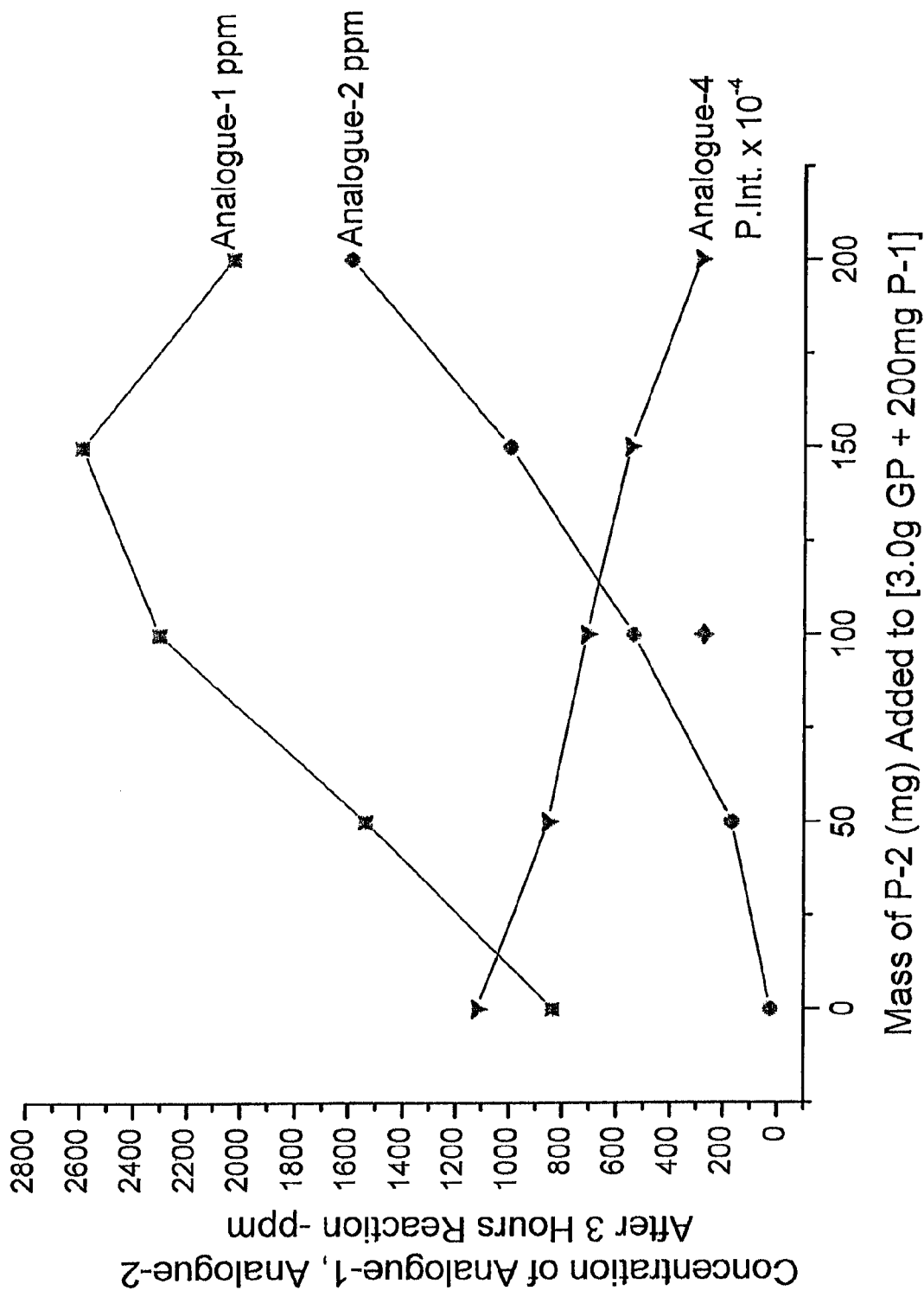

FIG. 24 shows the quantities of Analogue-1, Analogue-2 and Analogue-4 produced after 3 hours reaction time, which are now expressed as a function of the variable mass of Precursor-2 added to the reaction mixture; amount of Analogue-1 and Analogue-2 produced after 3 hours reaction time using different amounts of Precursor-2 added to 3.0 g GP+200 mg Precursor-1 mixed in 35 ml water. Integration data for Analogue-4 included.

Figure 25:
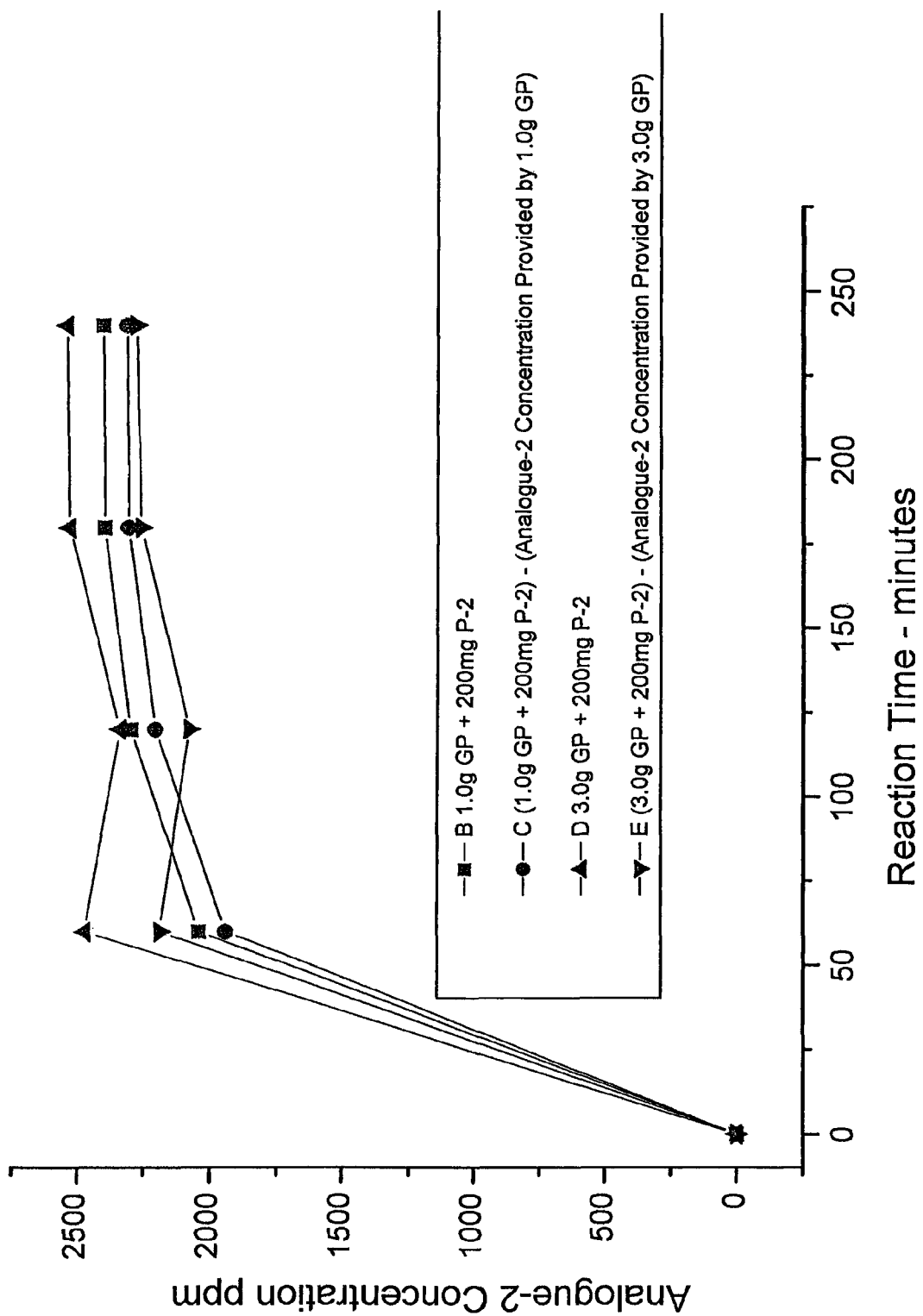

FIG. 25 shows the effect of the amount of GP (garlic powder) used on the rate of production of analogue-2 (allicin); effect of amount of GP used on rate of production of Analogue-2.

Figure 26:
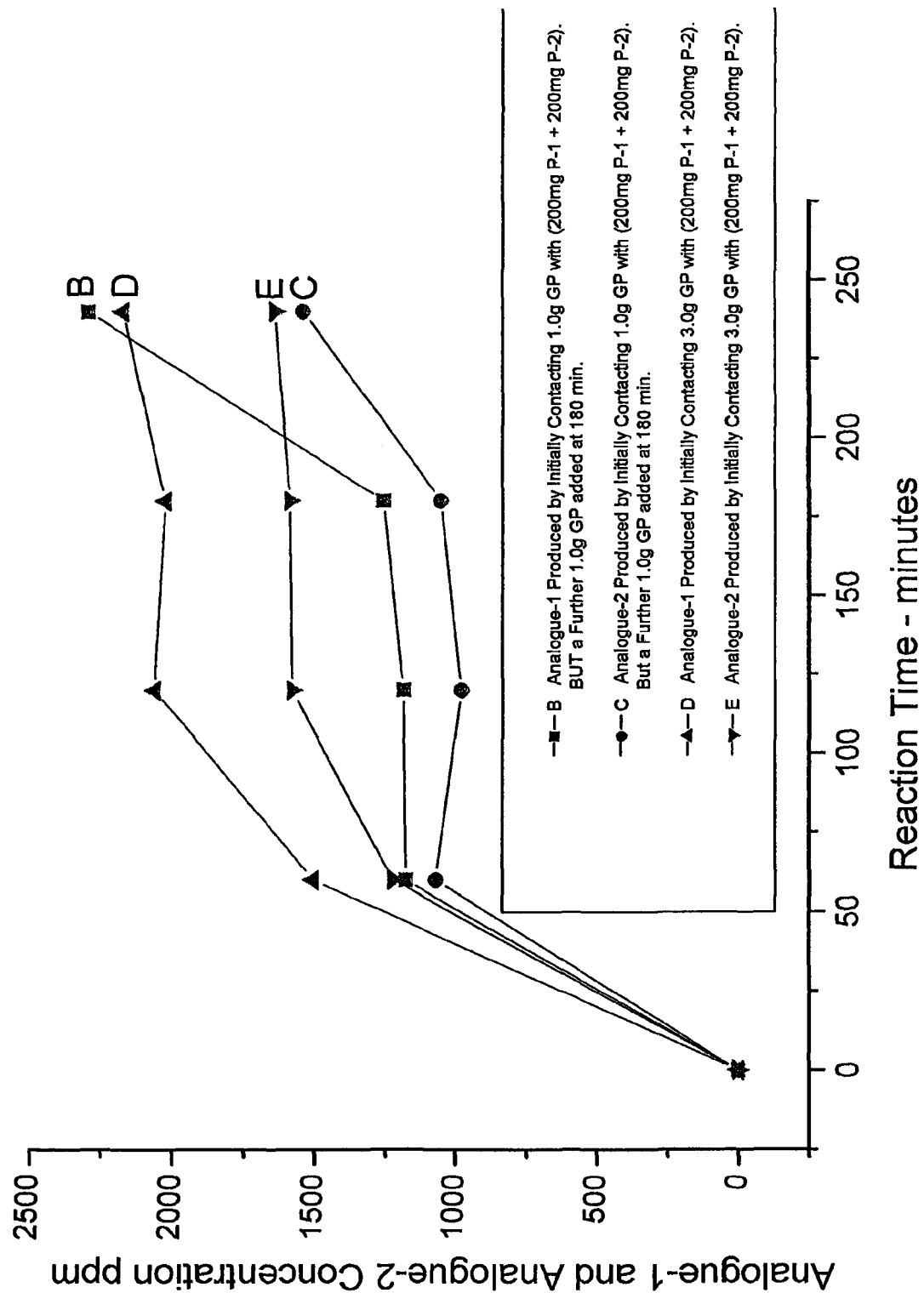

FIG. 26 shows the rate of production of Analogue-1 and Analogue-2 using different quantities of garlic powder. Rate of production of Analogue-1 and Analogue-2 using different quantities of garlic powder.

Figure 27:
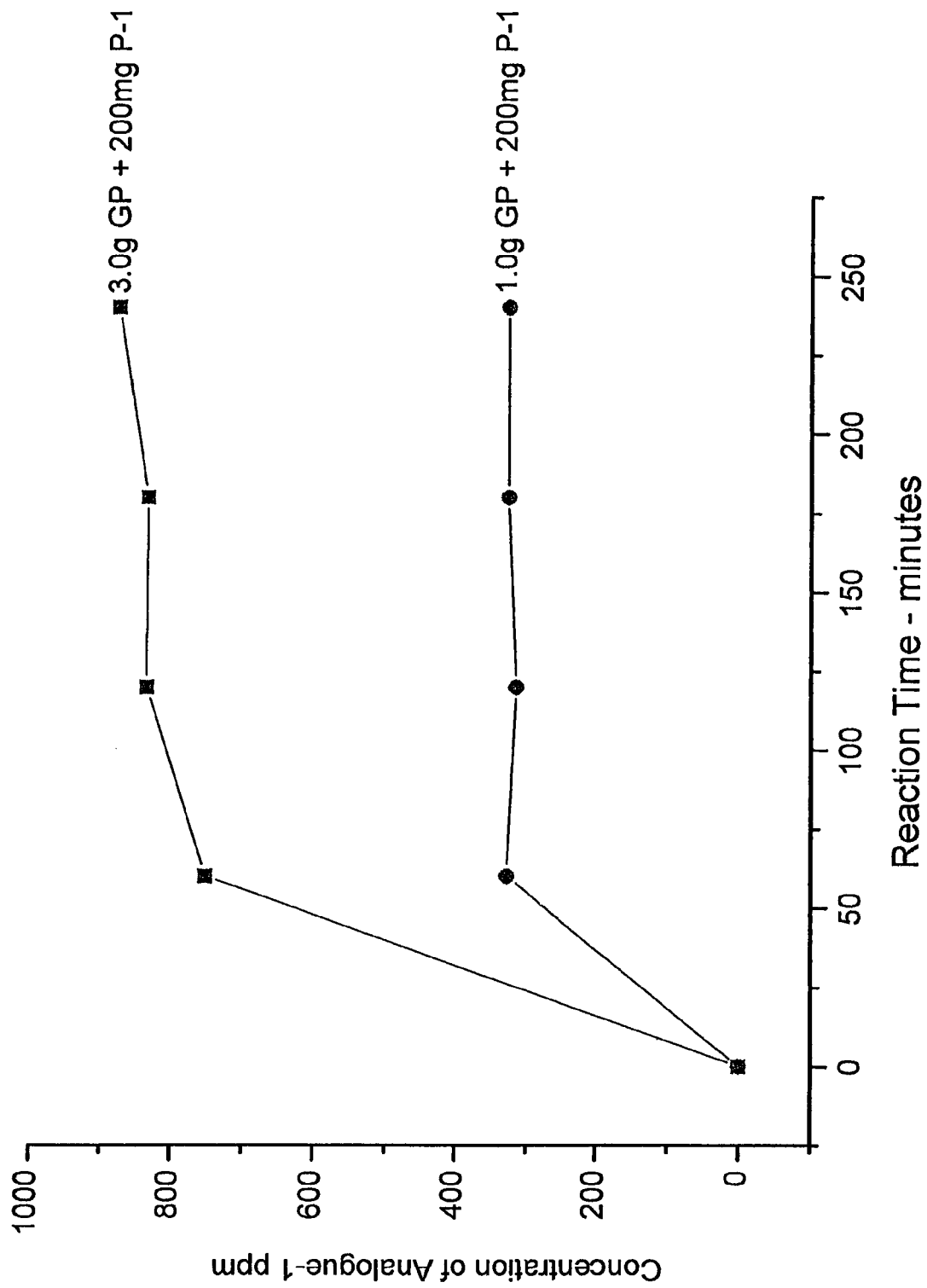

FIG. 27 shows the rate of production of Analogue-1 using different quantities of garlic powder. Rate of production of Analogue-1 using different quantities of garlic powder.

Figure 28:
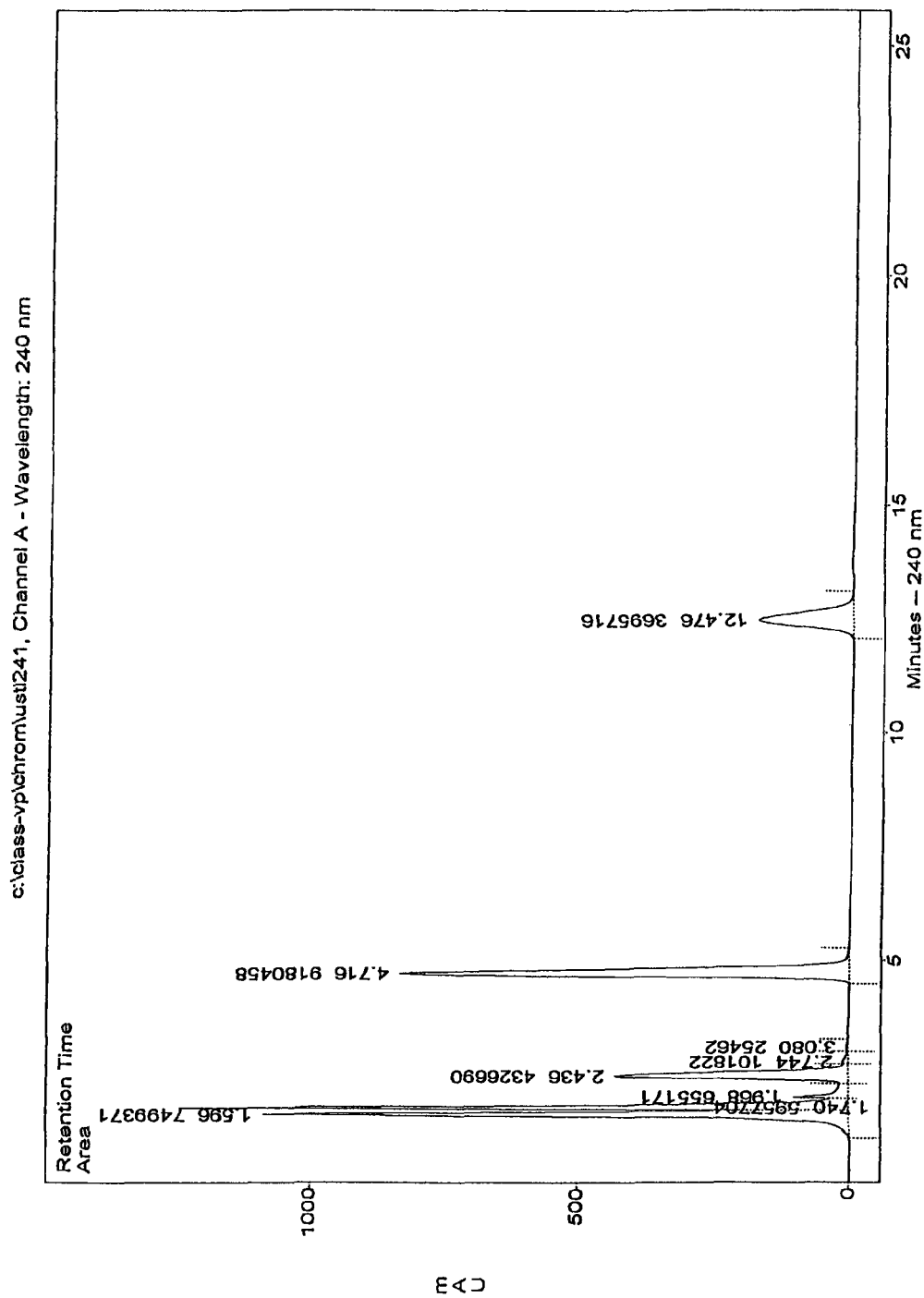
Figure 29:
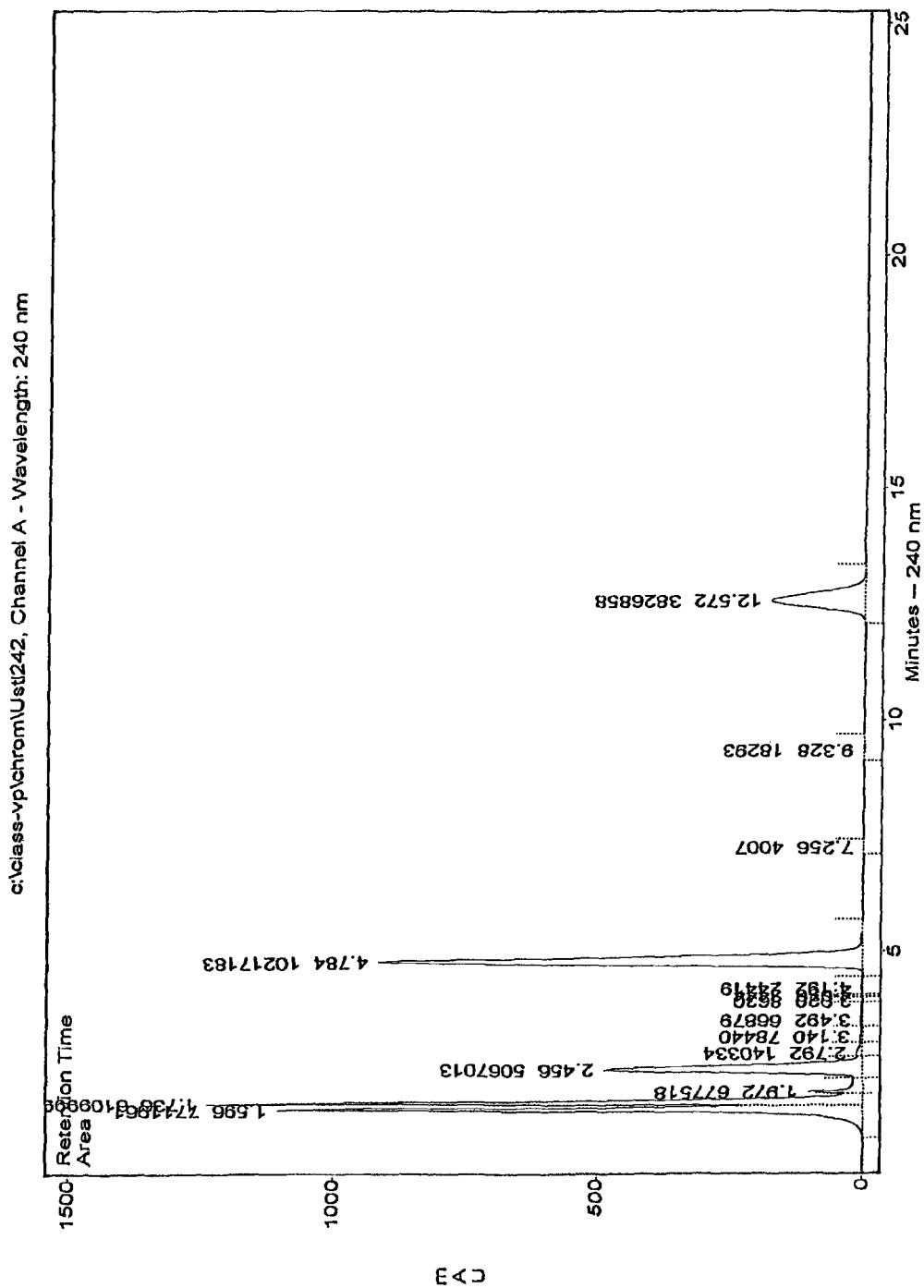
Figure 30:
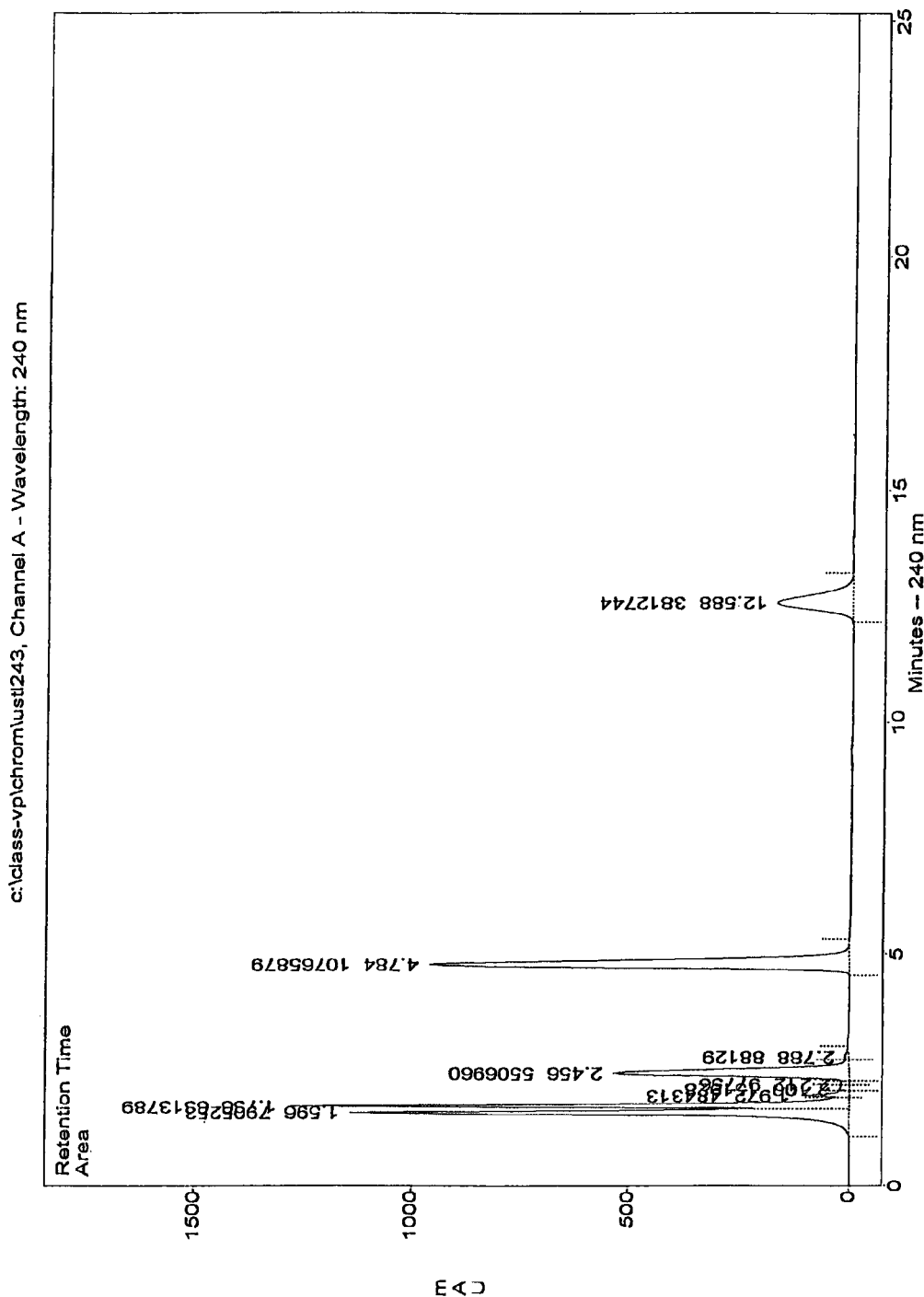
Figure 31:
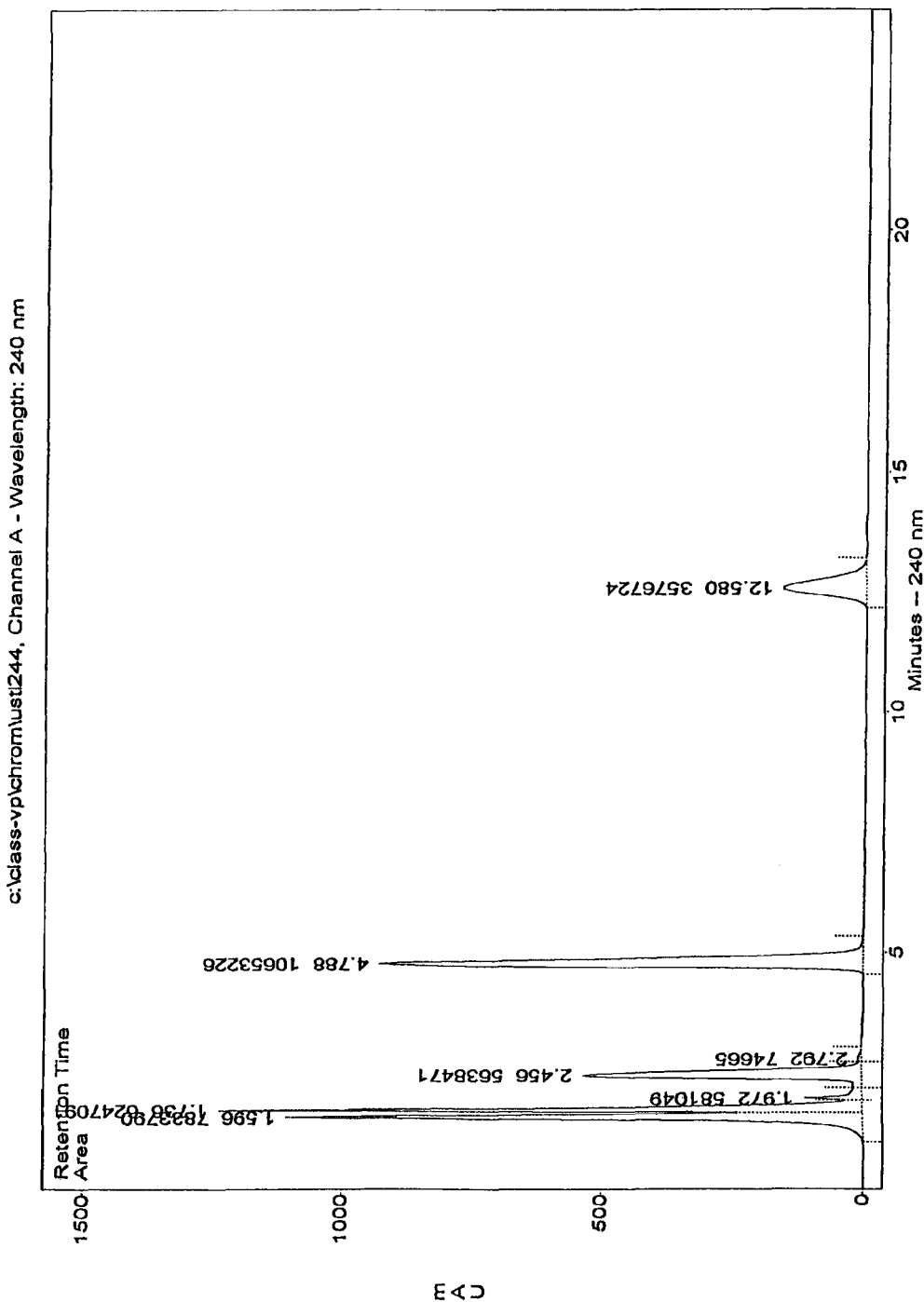
Figure 32:
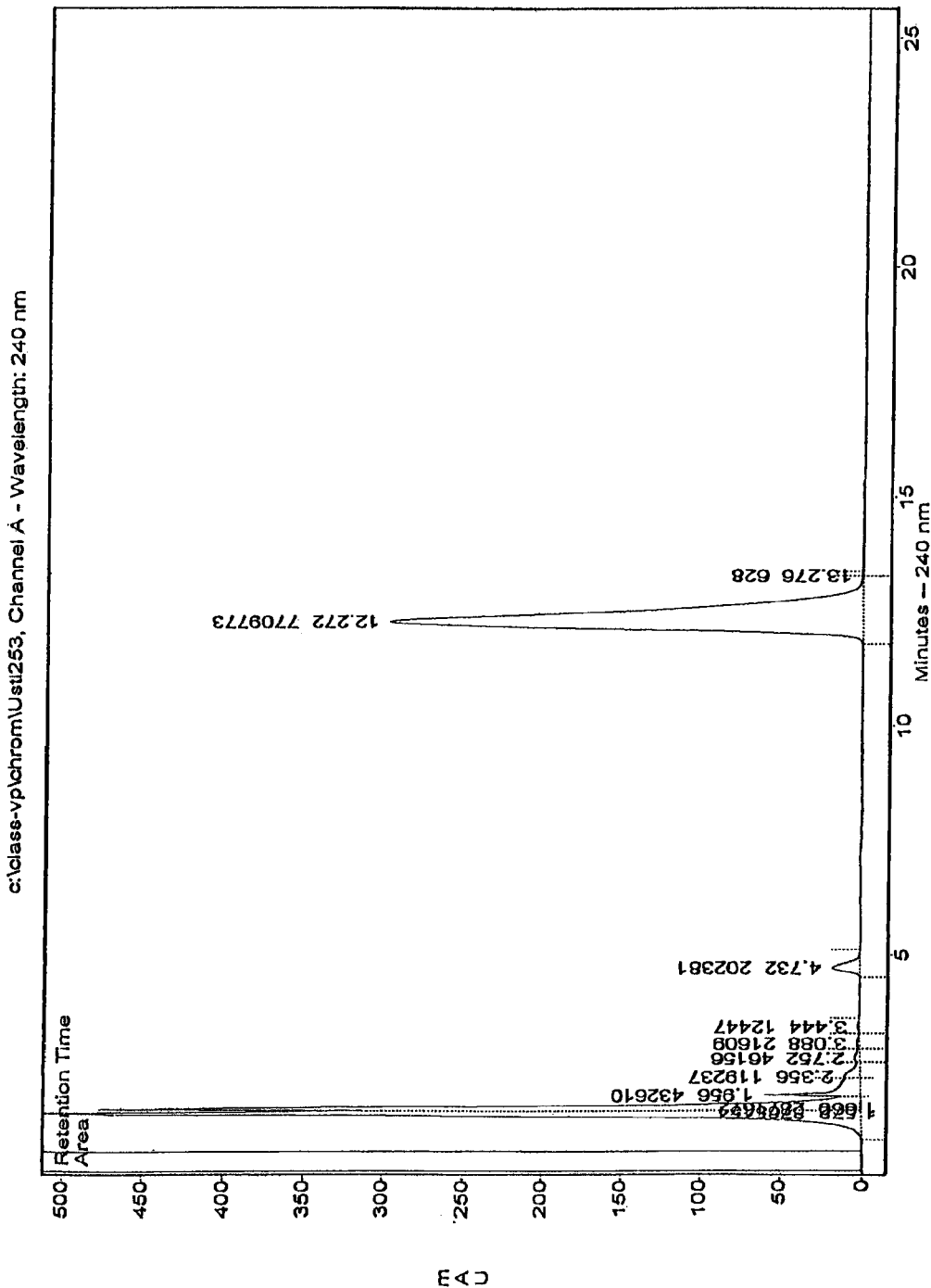
Figure 33:
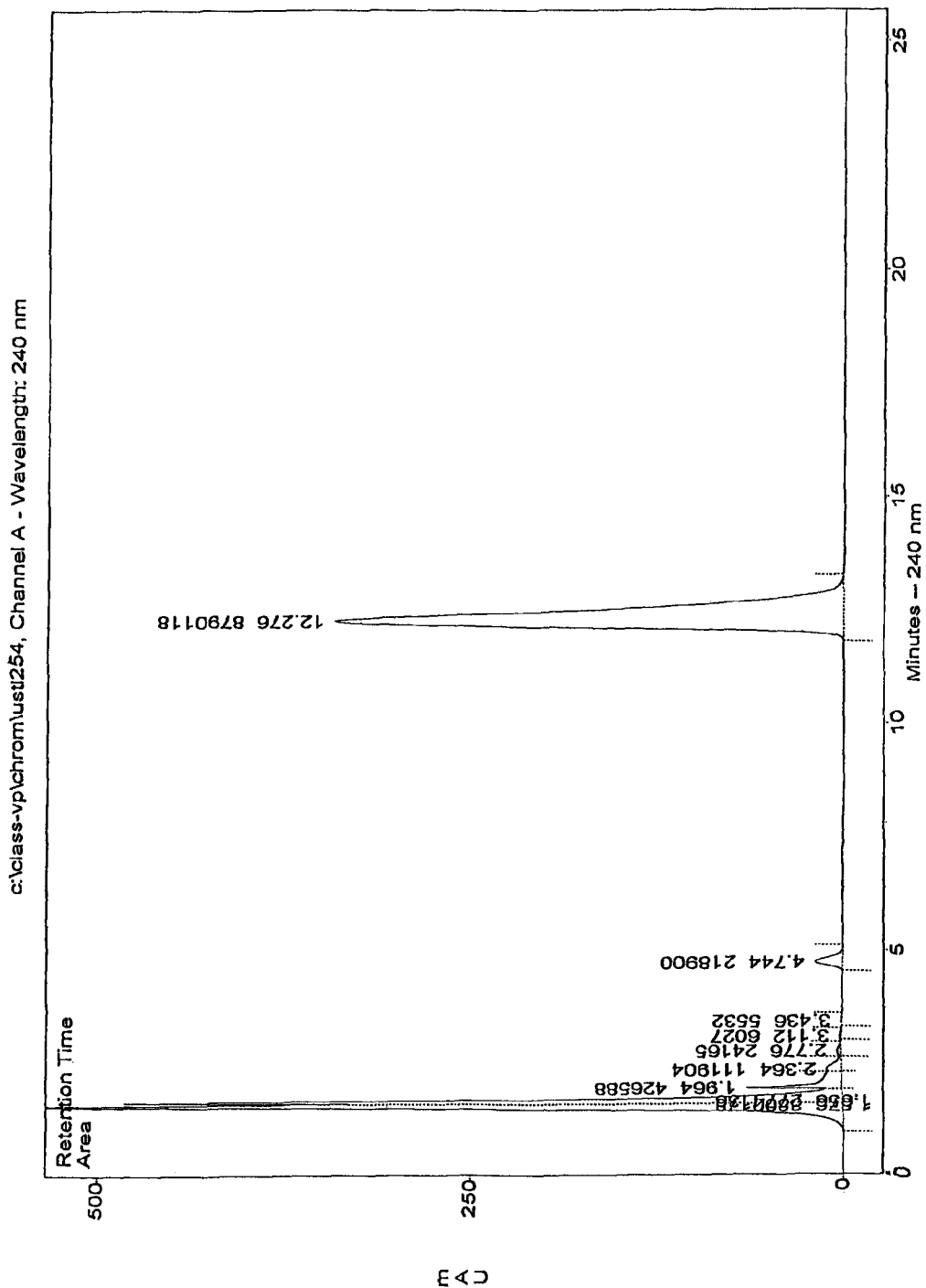
Figure 34:
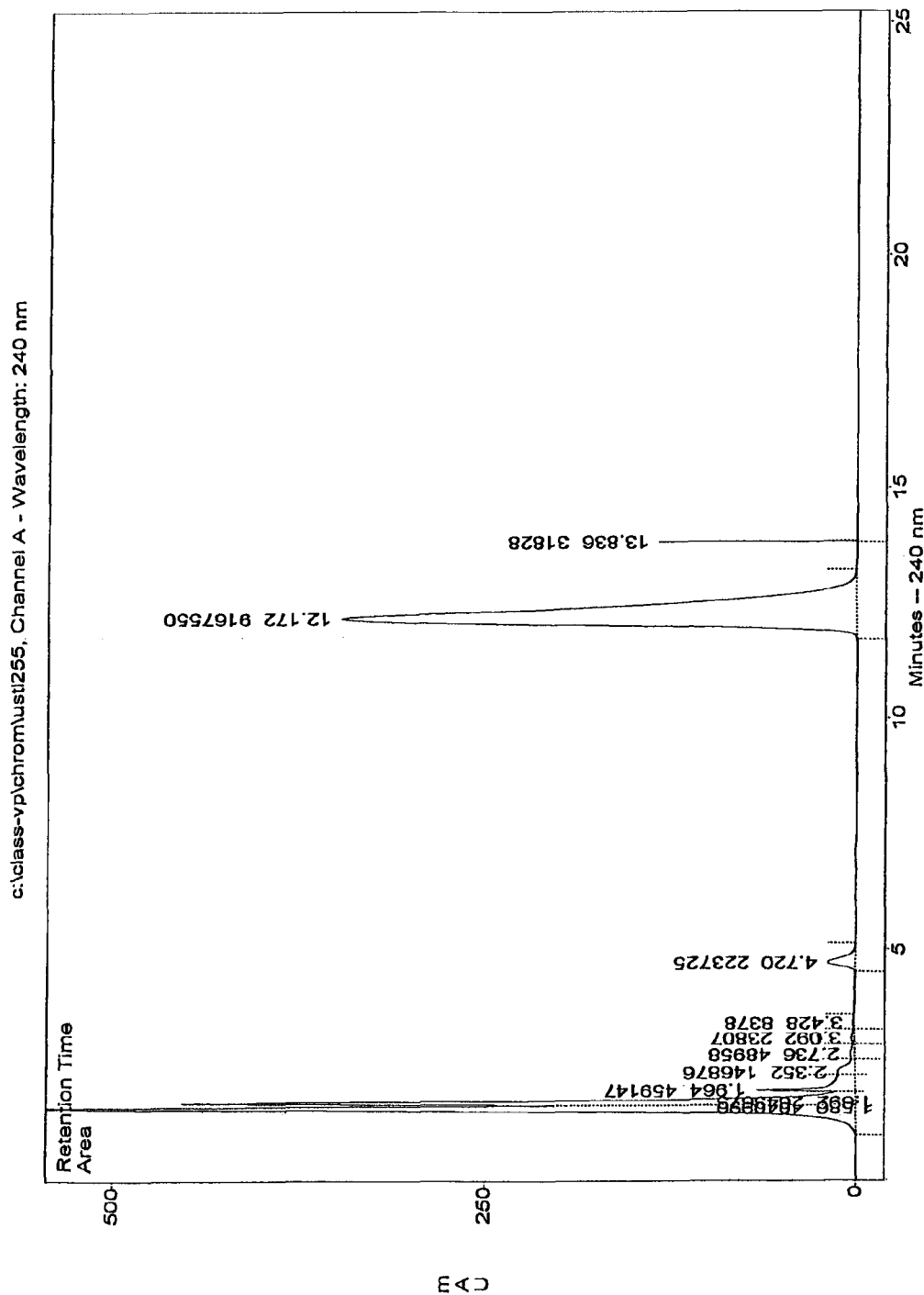
Figure 35:
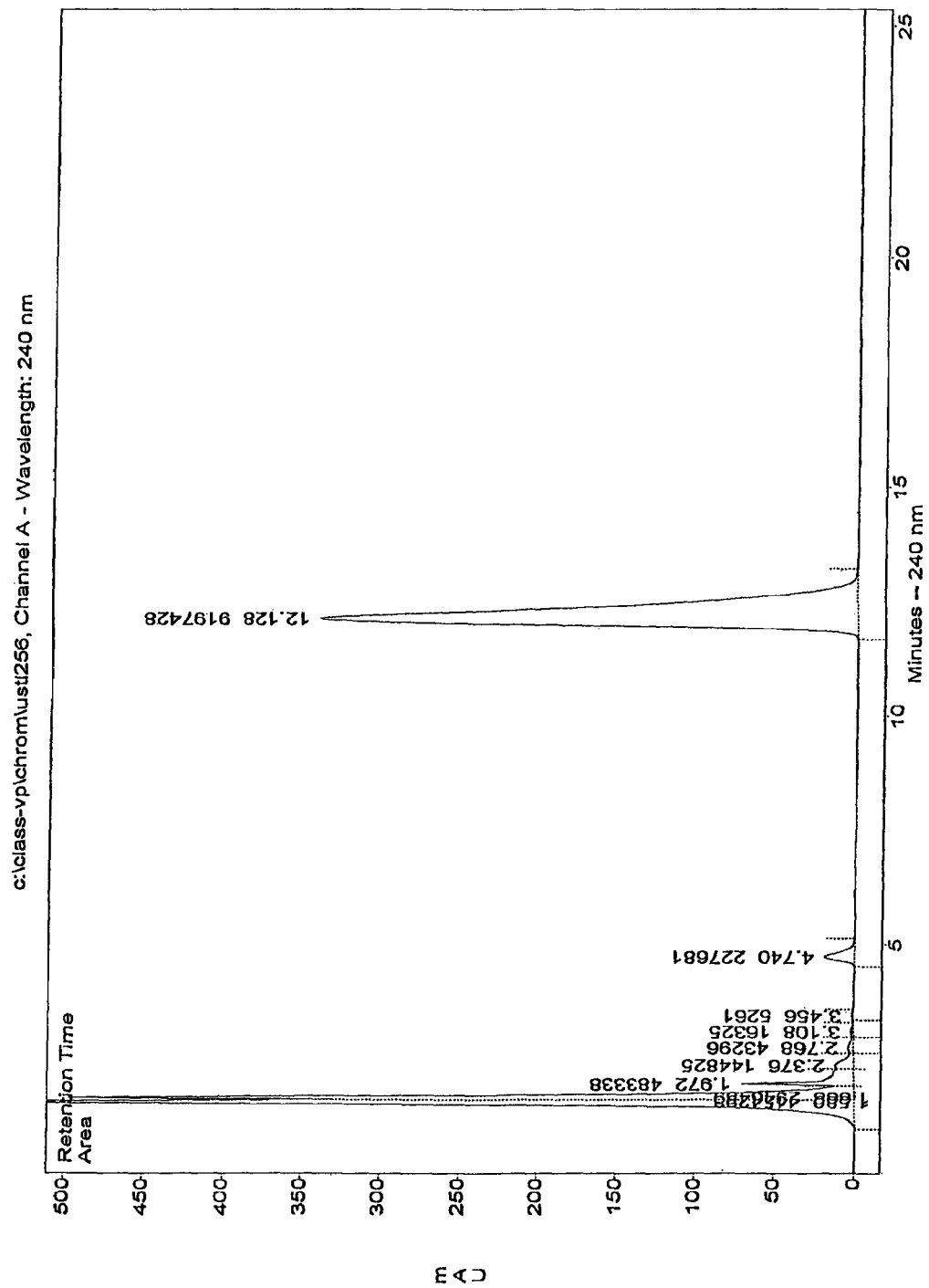
Figure 36:
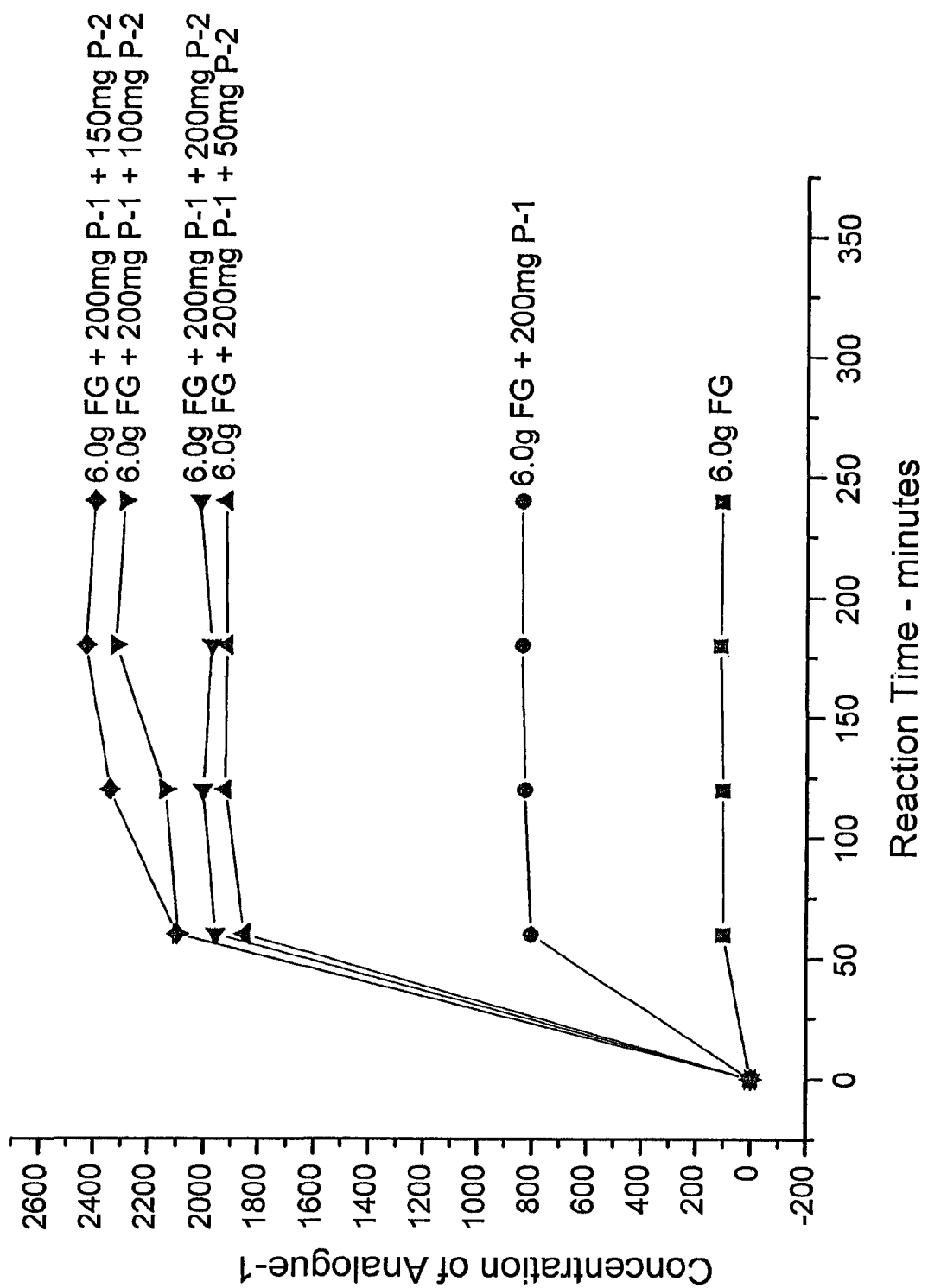

FIG. 28 shows a chromatogram obtained after 60 min reaction time for reaction mixture 3.0 g GP+200 mg P-1+150 mg P-2—mixed in 35 ml water (retention times: Analogue-1 at 4.716 min, Analogue-2 at 12.476 min, Analogue-4 at 2.436 min);

FIG. 29 shows a chromatogram obtained after 120 min reaction time for reaction mixture 3.0 g GP+200 mg P-1+150 mg P-2—mixed in 35 ml water (retention times: Analogue-1 at 4.784 min, Analogue-2 at 12.572 min, Analogue-4 at 2.456 min);

FIG. 30 shows a chromatogram obtained after 180 min reaction time for reaction mixture 3.0 g GP+200 mg P-1+150 mg P-2—mixed in 35 ml water (retention times: Analogue-1 at 4.784 min, Analogue-2 at 12.588 min, Analogue-4 at 2.456 min);

FIG. 31 shows a chromatogram obtained after 240 min reaction time for reaction mixture 3.0 g GP+200 mg P-1+150 mg P-2—mixed in 35 ml water (retention times: Analogue-1 at 4.788 min, Analogue-2 at 12.580 min, Analogue-4 at 2.456 min);

FIG. 32 shows a chromatogram obtained after 60 min reaction time for reaction mixture 1.0 g GP+200 mg P-2—mixed in 35 ml water (retention times: Analogue-1 at 4.732 min, Analogue-2 at 12.272 min; Analogue-4 effectively absent);

FIG. 33 shows a chromatogram obtained after 120 min reaction time for reaction mixture 1.0 g GP+200 mg P-2 mixed in 35 ml water (retention times: Analogue-1 at 4.744 min, Analogue-2 at 12.276 min; Analogue-4 effectively absent);

FIG. 34 shows a chromatogram obtained after 180 min reaction time for reaction mixture 1.0 g GP+200 mg P-2—mixed in 35 ml water (retention times: Analogue-1 at 4.720 min, Analogue-2 at 12.172 min; Analogue-4 effectively absent);

FIG. 35 shows a chromatogram obtained after 240 min reaction time for reaction mixture 1.0 g GP+200 mg P-2—mixed in 35 ml water (retention times: Analogue-1 at 4.740 min, Analogue-2 at 12.128 min; Analogue-4 effectively absent);

FIG. 36 shows the rate of production for Analogue-1; FG—rate of production of Analogue-1.

Figure 37:
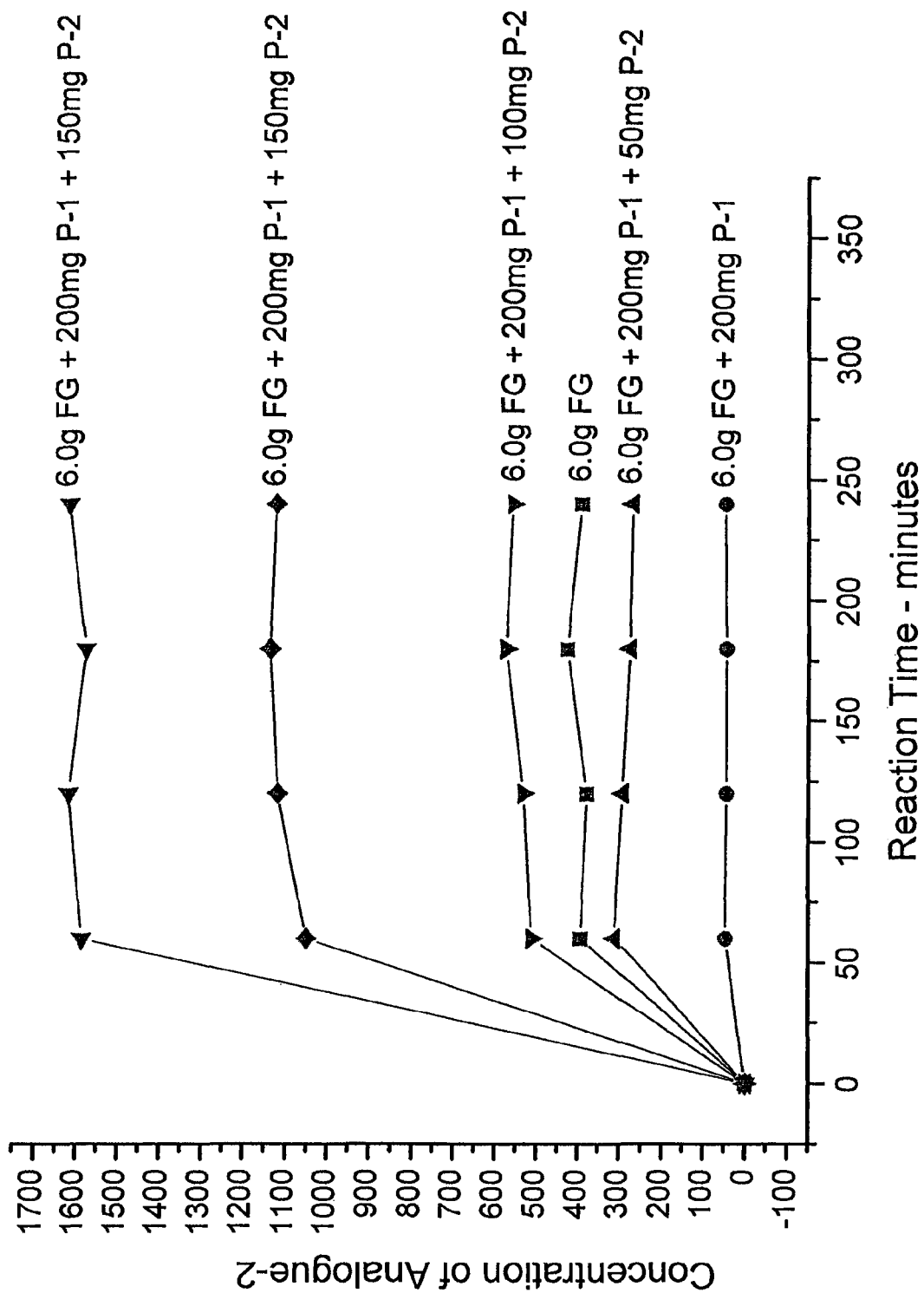

FIG. 37 shows the rate of production for Analogue-2; FG—rate of production of Analogue-2.

Figure 38:
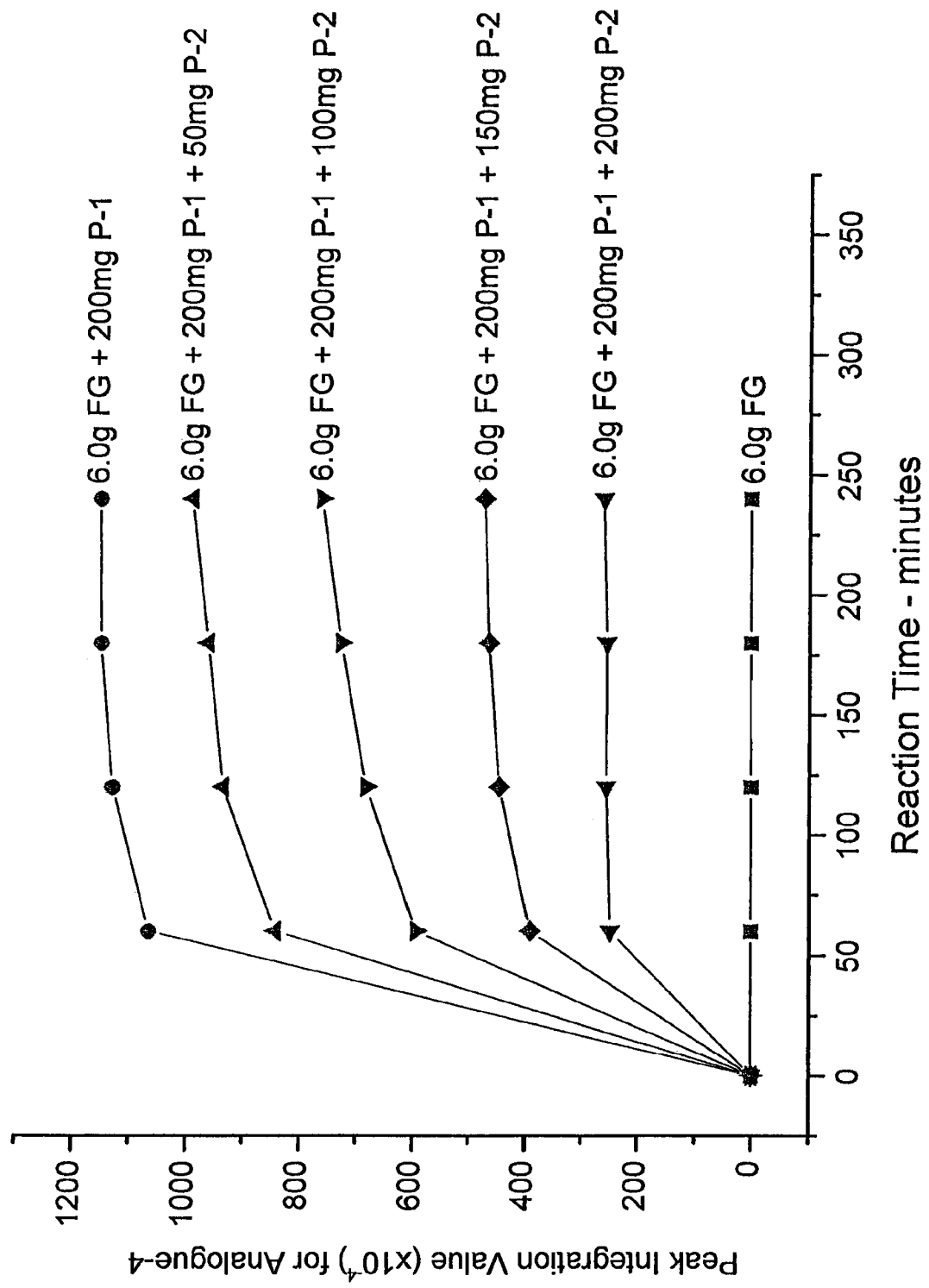

FIG. 38 shows the rate of production for Analogue-4 (retention time approx. 2.5 minutes); FG—rate of production of Analogue-4 (retention time approx. 2.5 min).

Figure 39:
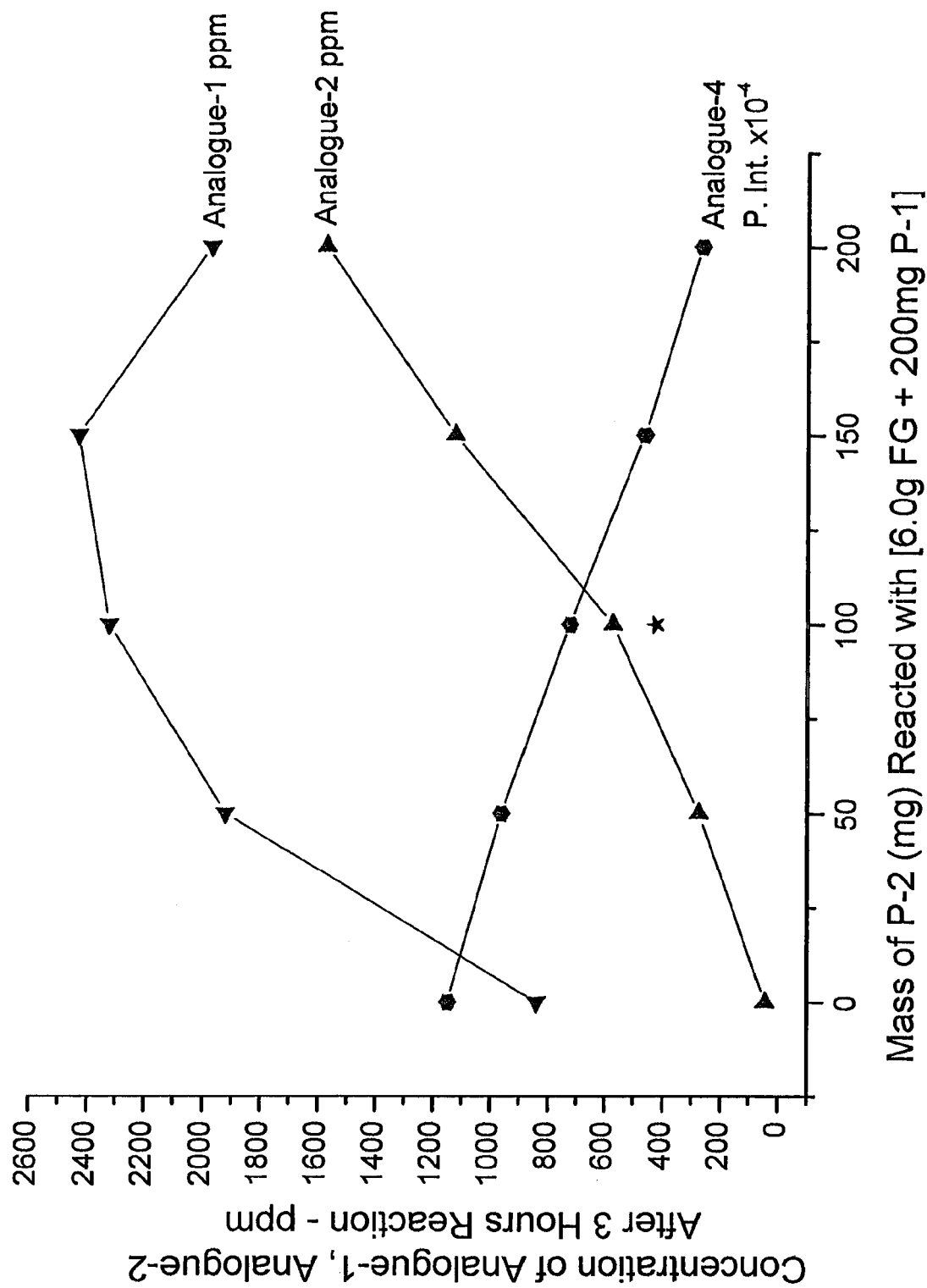

FIG. 39 shows identical characteristics to those previously shown and discussed for FIG. 24; amount of Analogue-1 and Analogue-2 produced after 3 hours reaction time using different amounts of Precursor-2 reacted with [6.0 g FG+200 mg P-1] mixed in equivalent of 35 ml water. Integration data for Analogue-4 included.

Figure 40:
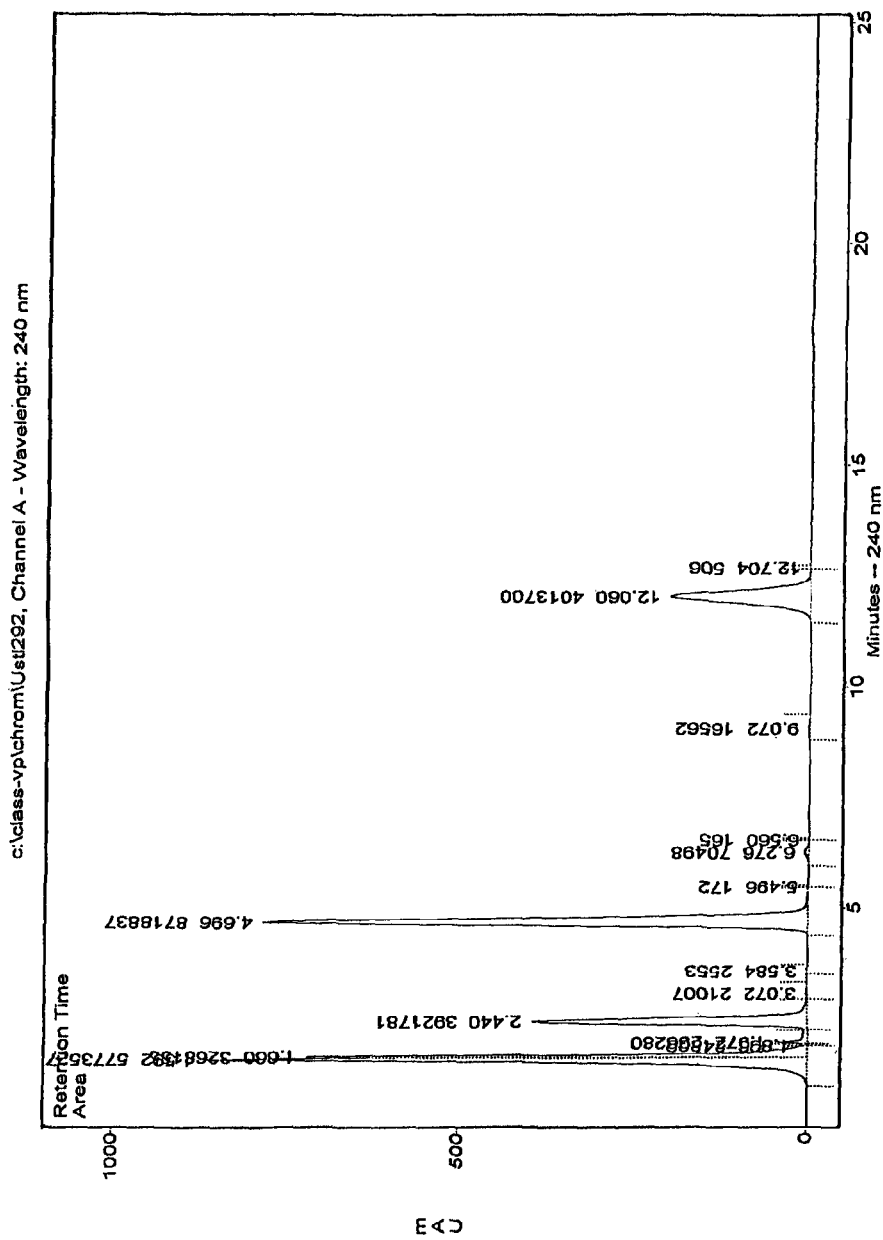
Figure 41:
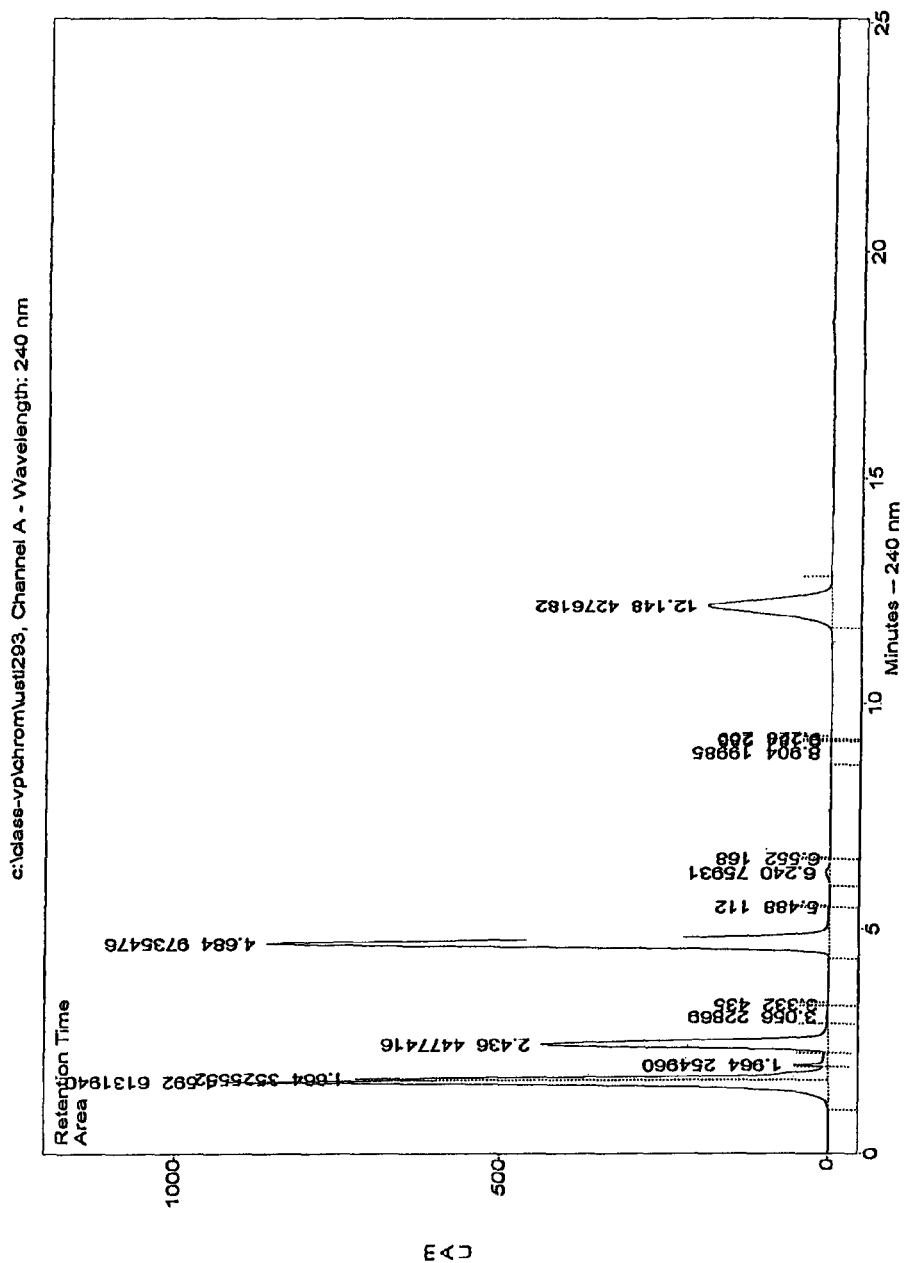
Figure 42:
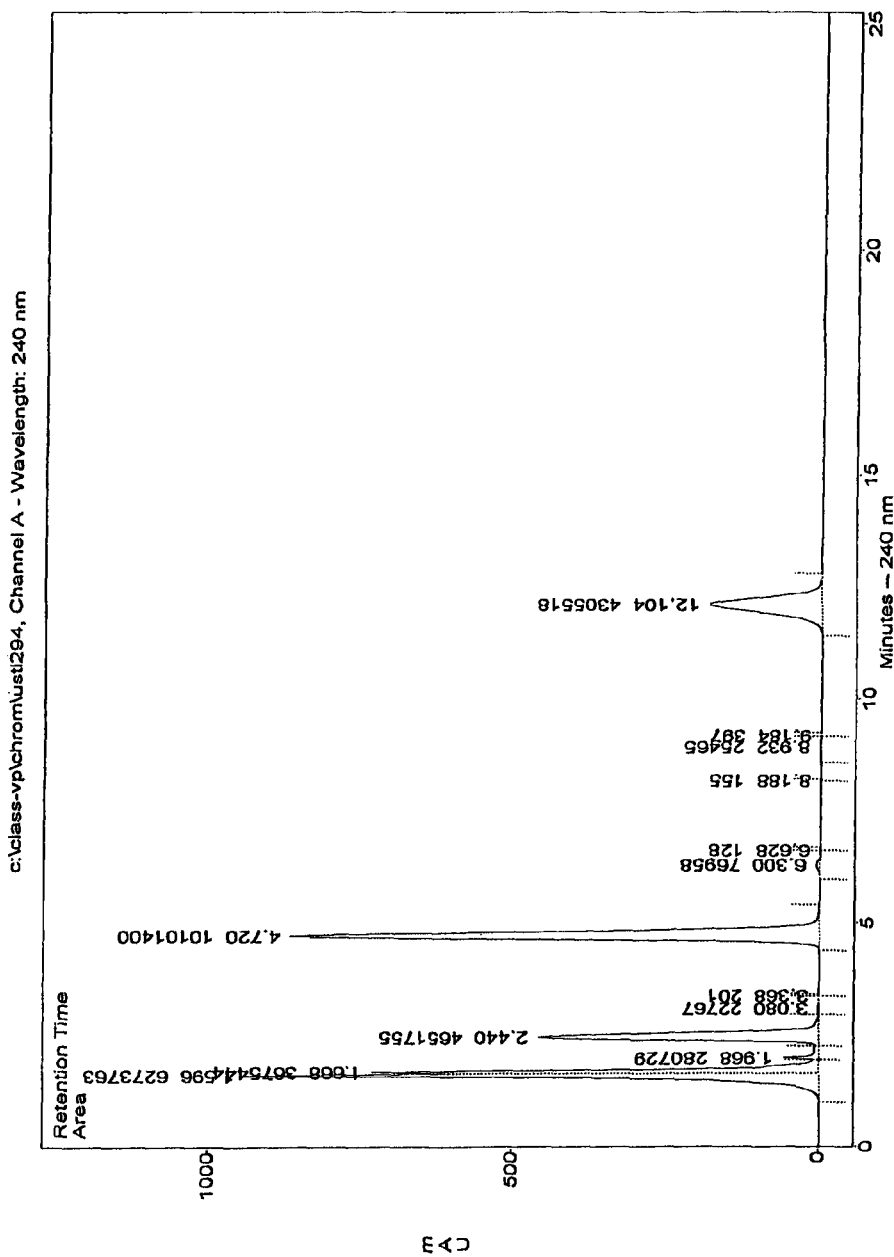
Figure 43:
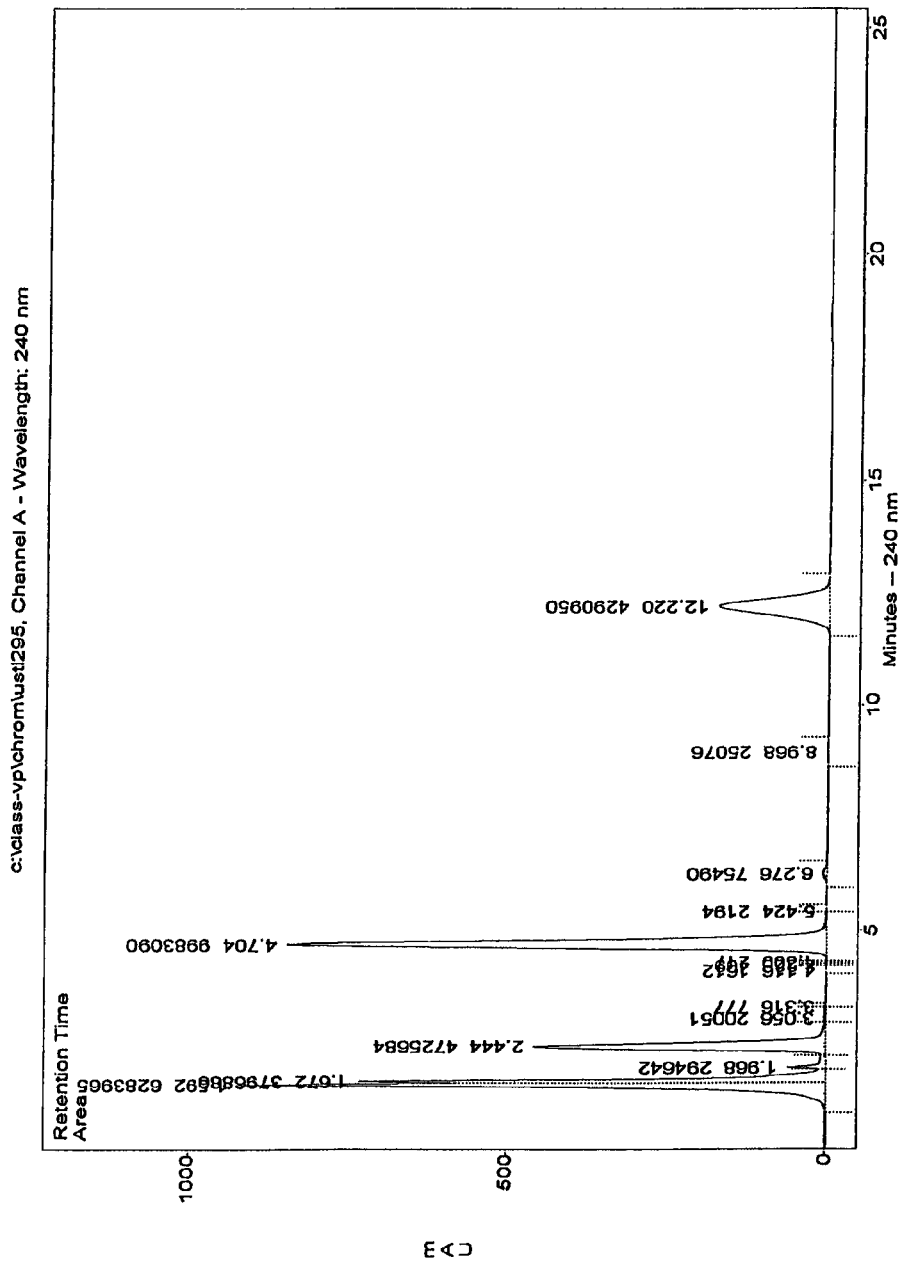
Figure 44:
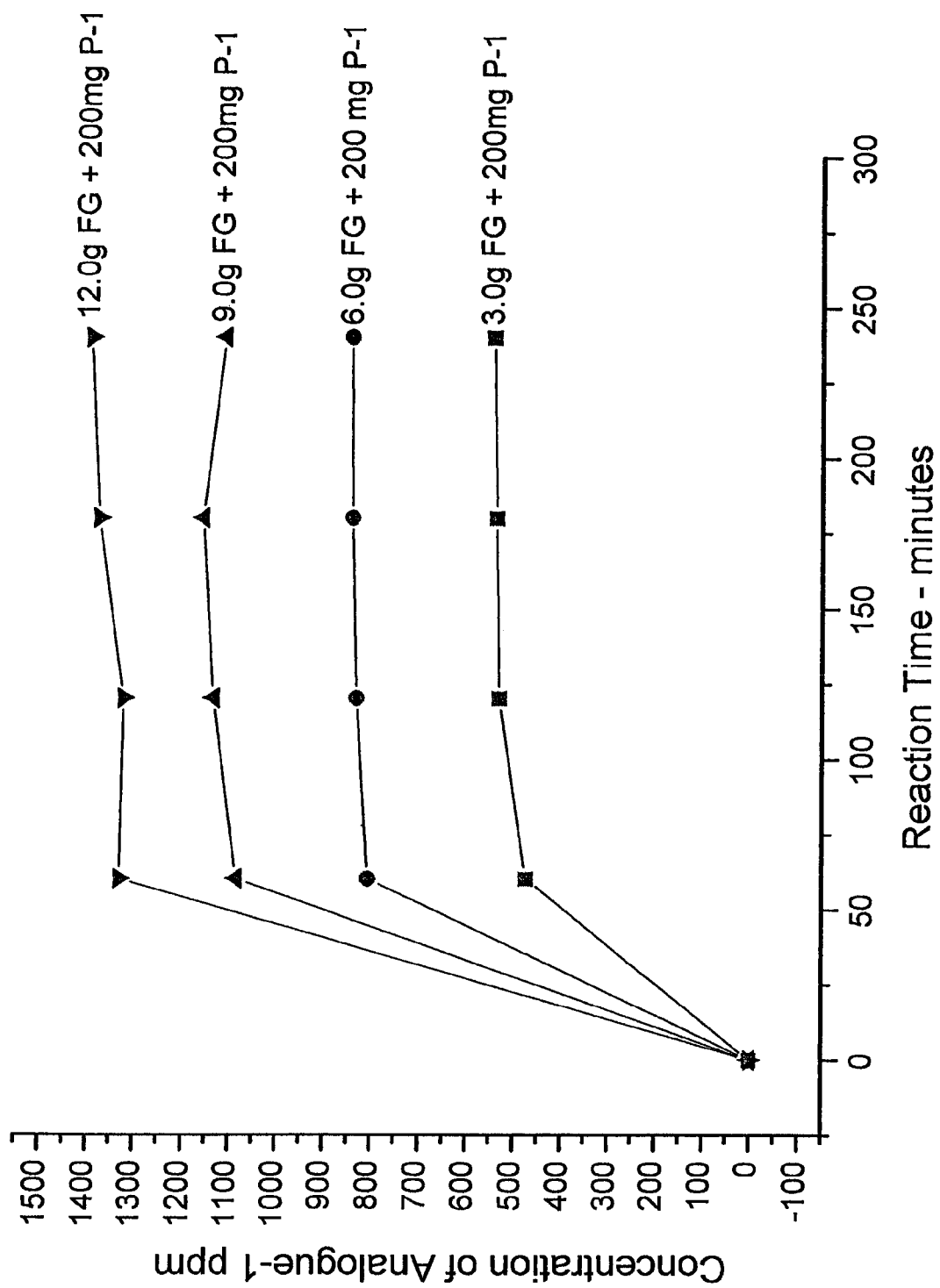

FIG. 40 shows a chromatogram obtained after 60 min reaction time for reaction mixture [12.0 g FG+400 mg P-1+300 mg P-2]—mixed in 70 ml water (retention times: Analogue-1 at 4.696 min, Analogue-2 at 12.060 min, Analogue-4 at 2.440 min);

FIG. 41 shows a chromatogram obtained after 120 min reaction time for reaction mixture [12.0 g FG+400 mg P-1+300 mg P-2]—mixed in 70 ml water (retention times: Analogue-1 at 4.684 min, Analogue-2 at 12.148 min, Analogue-4 at 2.436 min);

FIG. 42 shows a chromatogram obtained after 180 min reaction time for reaction mixture [12.0 g FG+400 mg P-1+300 mg P-2]—mixed in 70 ml water (retention times: Analogue-1 at 4.720 min, Analogue-2 at 12.104 min, Analogue-4 at 2.440 min);

FIG. 43 shows a chromatogram obtained after 240 min reaction time for reaction mixture [12.0 g FG+400 mg P-1+300 mg P-2]—mixed in 70 ml water (retention times: Analogue-1 at 4.704 min, Analogue-2 at 12.220 min, Analogue-4 at 2.444 min);

FIG. 44 shows the rate of production for Analogue-1 with various masses of FG acting as the source of P-2 and allinase; FG—rate of production of Analogue-1.

Figure 45:
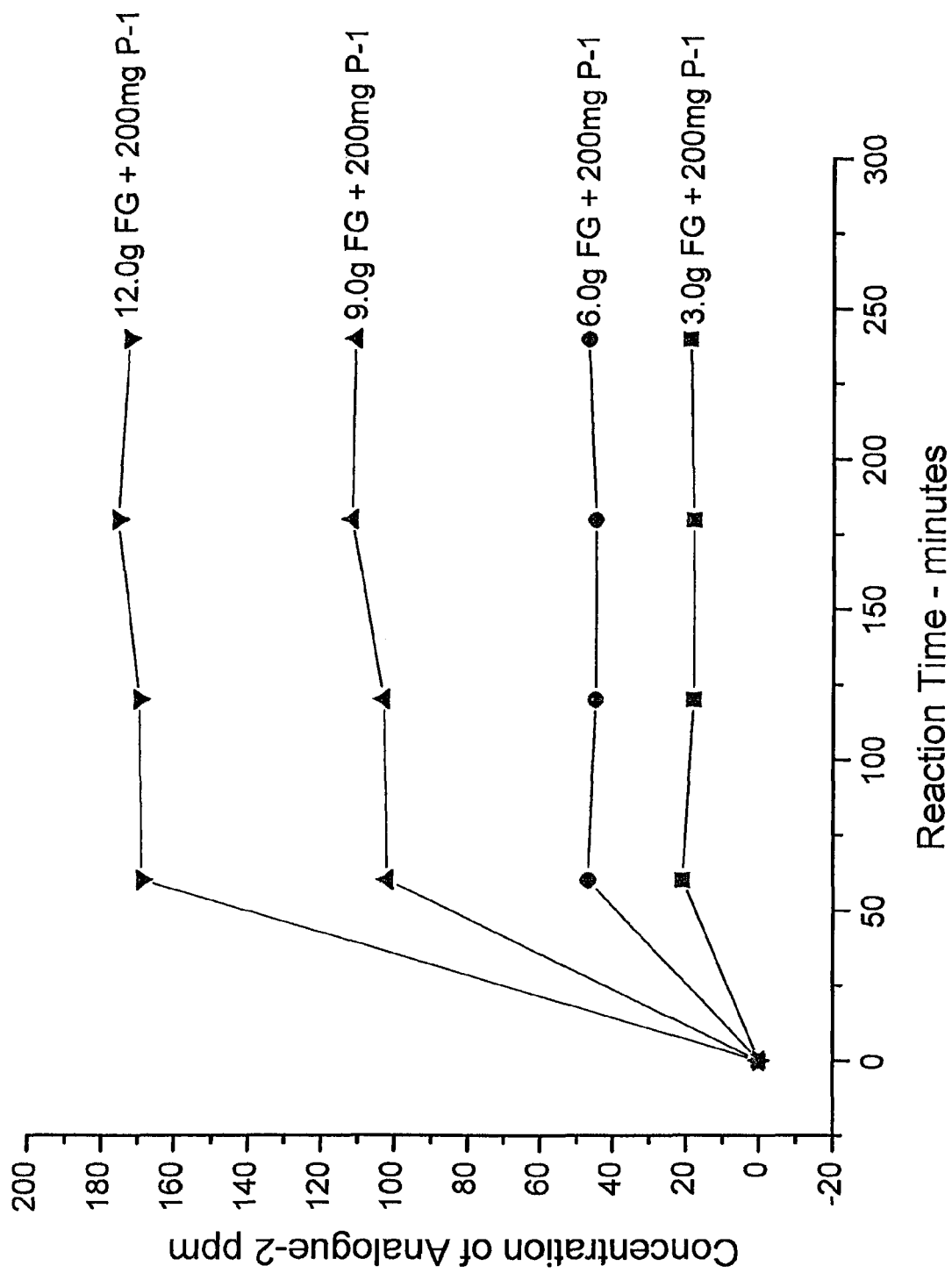

FIG. 45 shows the rate of production for Analogue-2; FG—rate of production of Analogue-2.

Figure 46:
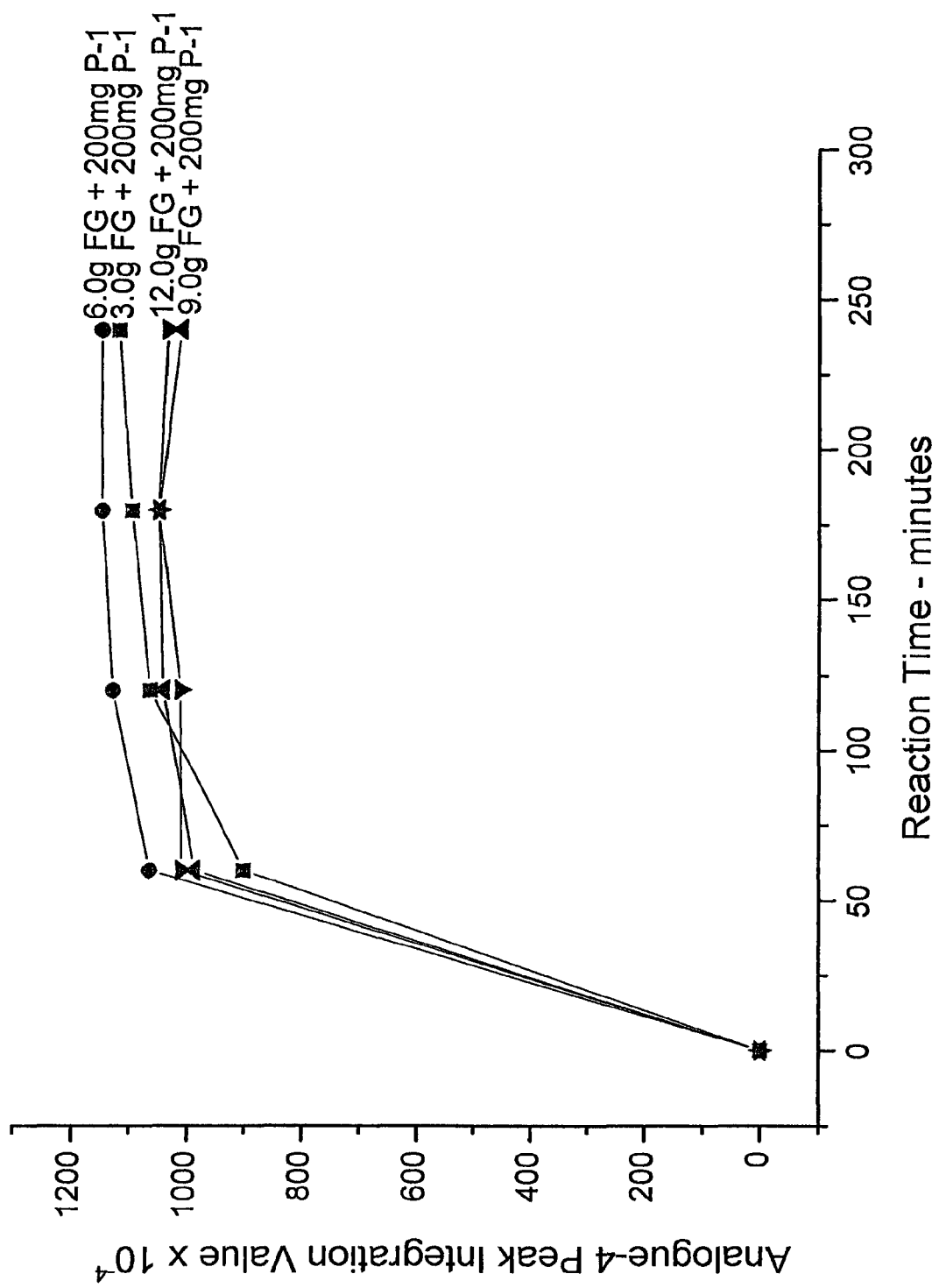

FIG. 46 shows the rate of production for Analogue-4 (retention time approx. 2.5 minutes; note there is only a relatively small variation in the quantity of Analogue-4 produced through the range of different masses of FG studied; this would tend to suggest some "buffering" type relationship with the 200 mg (equivalent amount in 35 ml water) P-1 used); FG—rate of Analogue-4 production.

Figure 47:
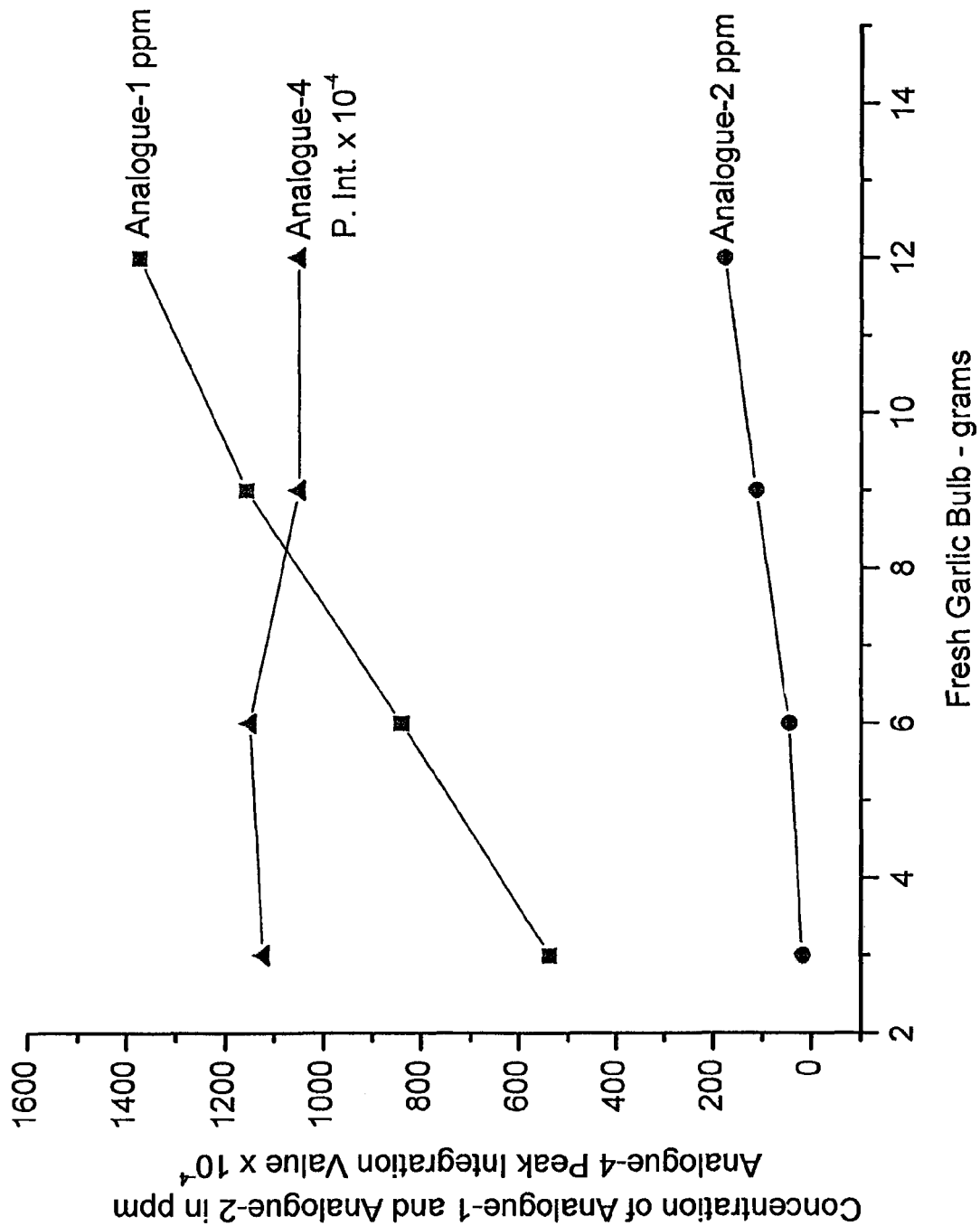

FIG. 47 can be constructed based on FIGS. 44-46 and shows the concentrations of Analogue-1 (Analogue-2 and Analogue-4 determined at 3 hours as a function of the mass of FG used); rate of production of Analogue-1, Analogue-2 and Analogue-4 after 3 hours reaction time. Varying quantities of fresh garlic in equivalent of [35 ml water+200 mg P-1].

Figure 48:
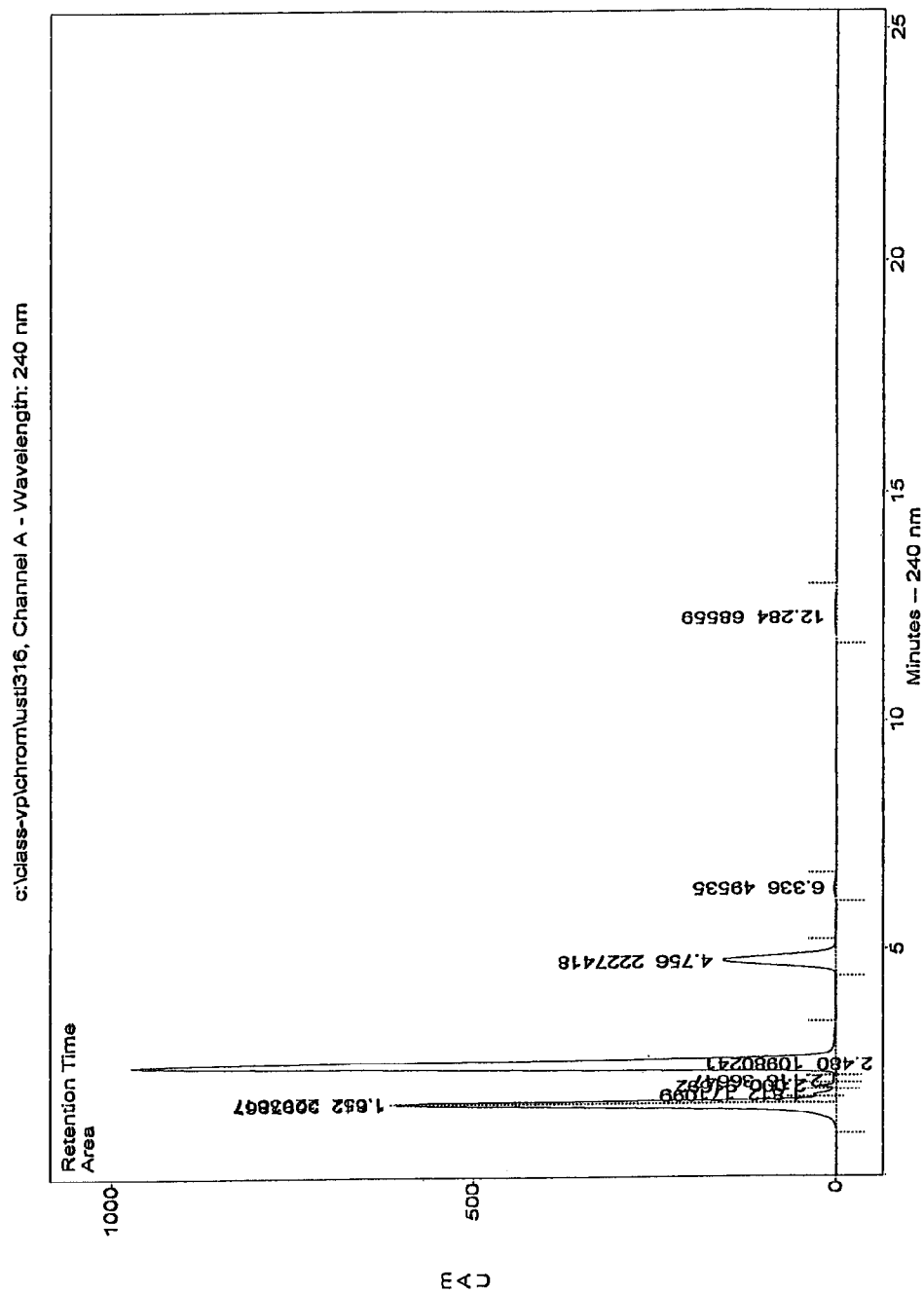
Figure 49:
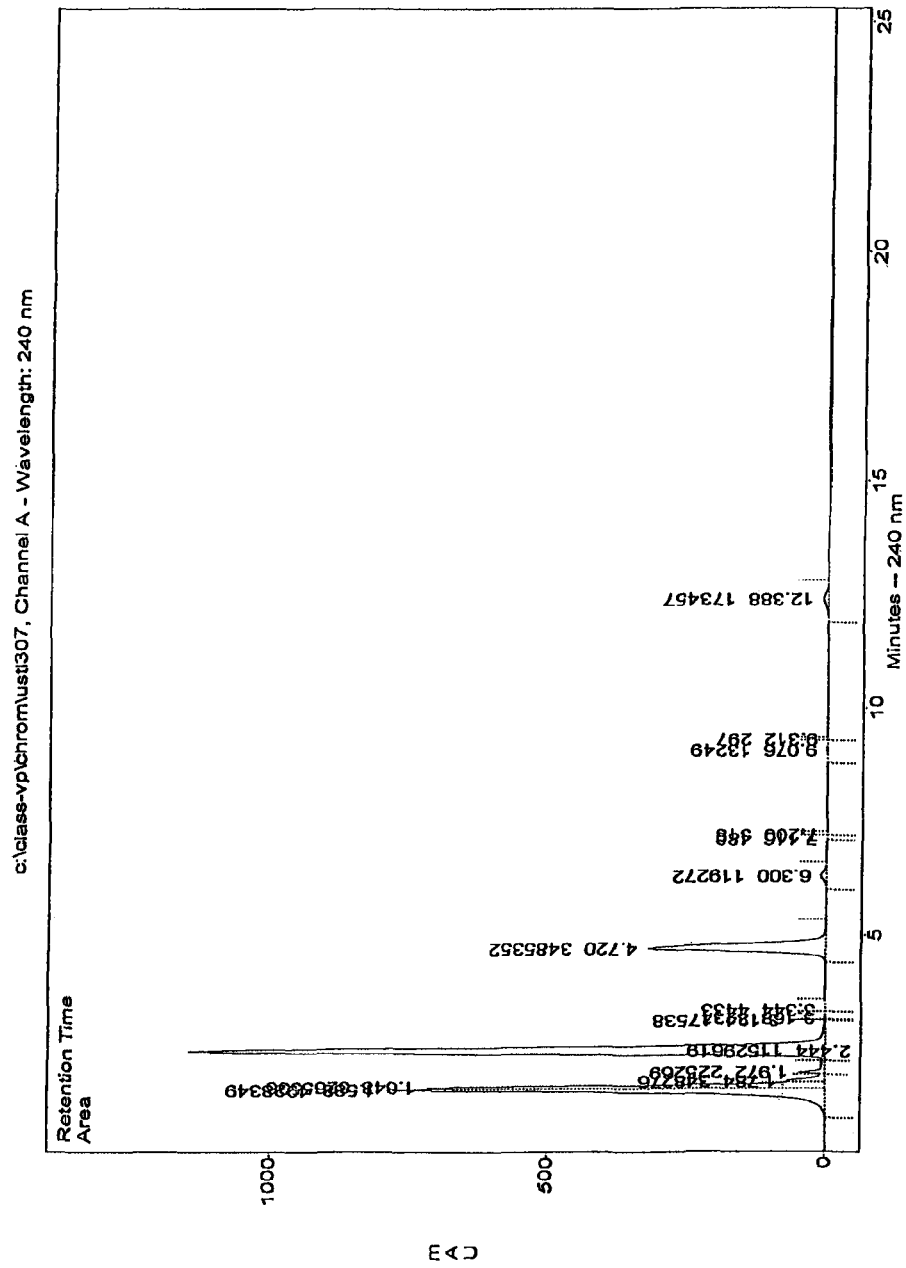
Figure 50:
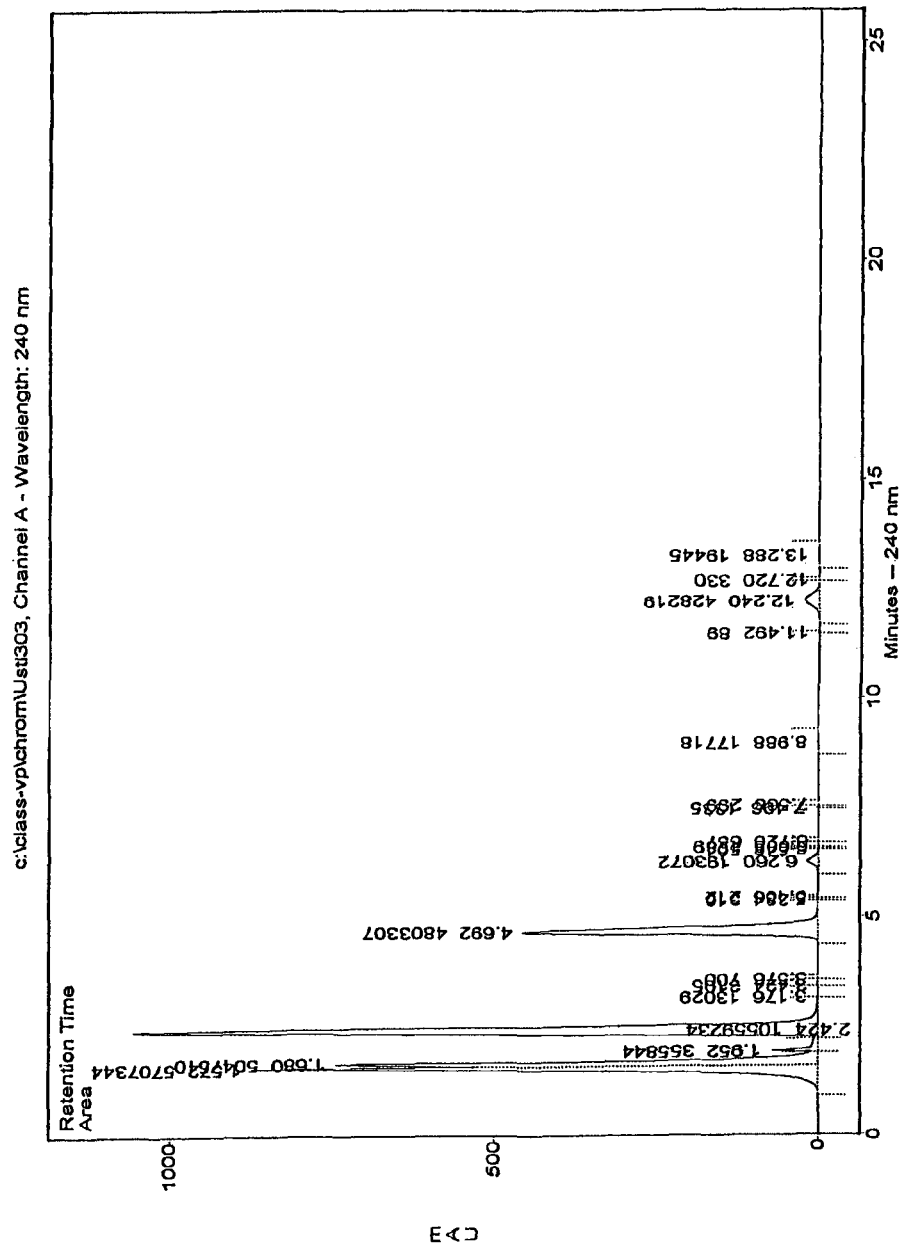
Figure 51:
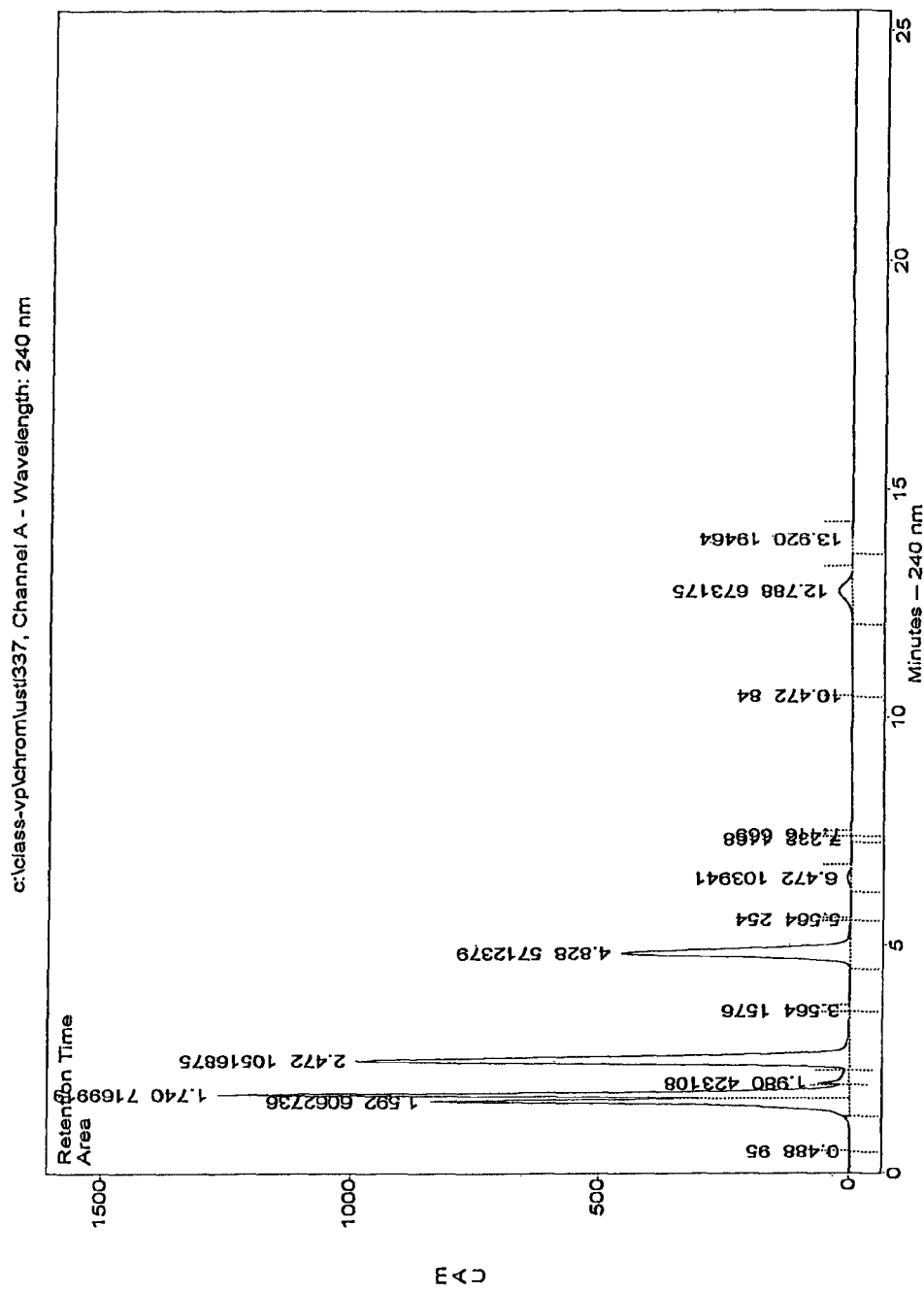

FIG. 48 shows a chromatogram obtained after 180 min reaction time for reaction mixture [6.0 g FG+400 mg P-1]—mixed in 70 ml water (retention times: Analogue-1 at 4.756 min, Analogue-2 at 12.284 min, Analogue-4 at 2.480 min);

FIG. 49 shows a chromatogram obtained after 180 min reaction time for reaction mixture [12.0 g FG+400 mg P-1]—mixed in 70 ml water (retention times: Analogue-1 at 4.720 min, Analogue-2 at 12.388 min, Analogue-4 at 2.444 min);

FIG. 50 shows a chromatogram obtained after 180 min reaction time for reaction mixture [18.0 g FG+400 mg P-1]—mixed in 70 ml water (retention times: Analogue-1 at 4.692 min, Analogue-2 at 12.240 min, Analogue-4 at 2.424 min);

FIG. 51 shows a chromatogram obtained after 180 min reaction time for reaction mixture [24.0 g FG+400 mg P-1]—mixed in 70 ml water (retention times: Analogue-1 at 4.828 min, Analogue-2 at 12.788 min, Analogue-4 at 2.472 min).

Figure 52:
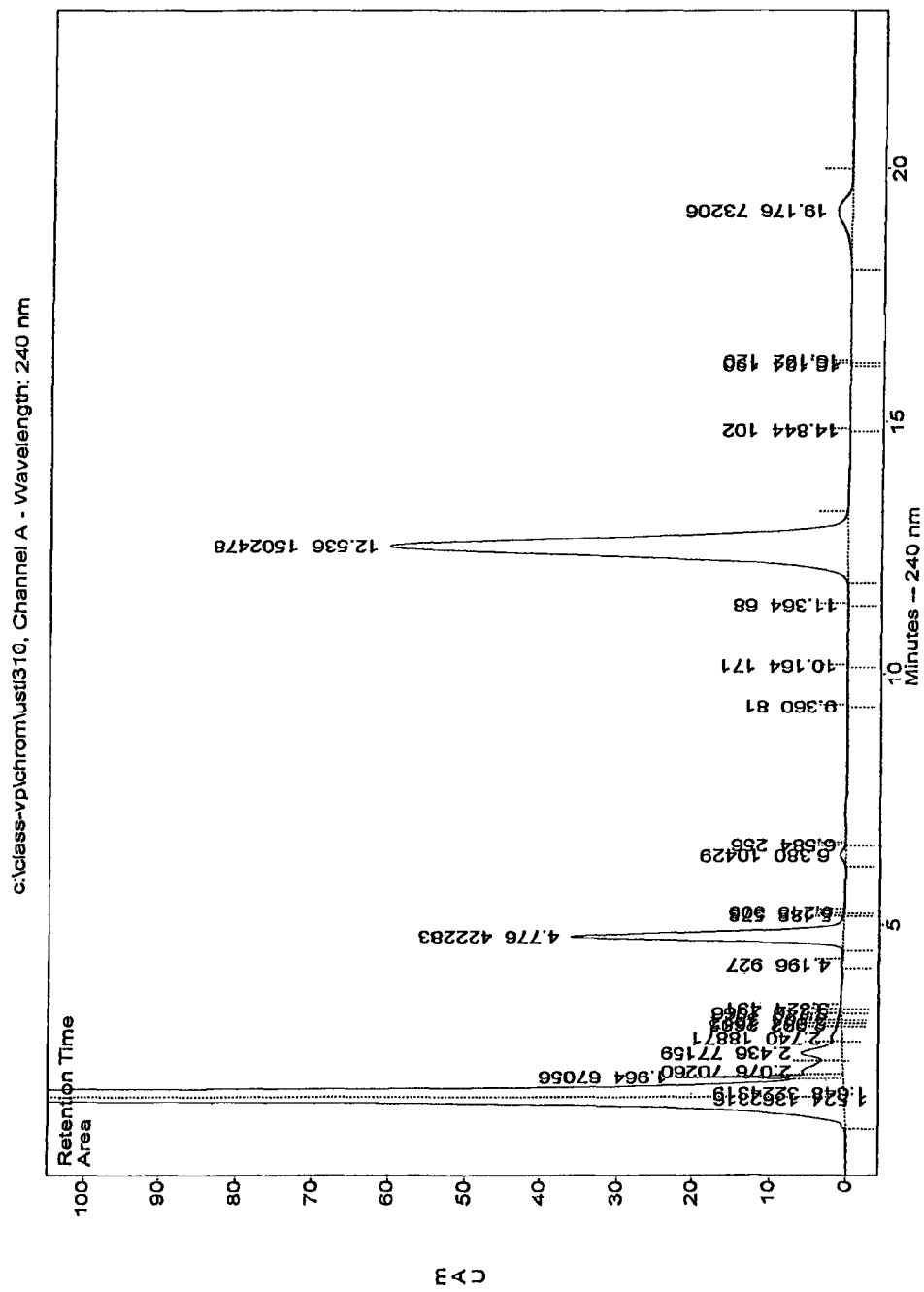

FIG. 52 shows the chromatogram obtained for 12.0 g FG mixed in 70 ml water that was obtained after 60 minutes mixing.

Figure 53:
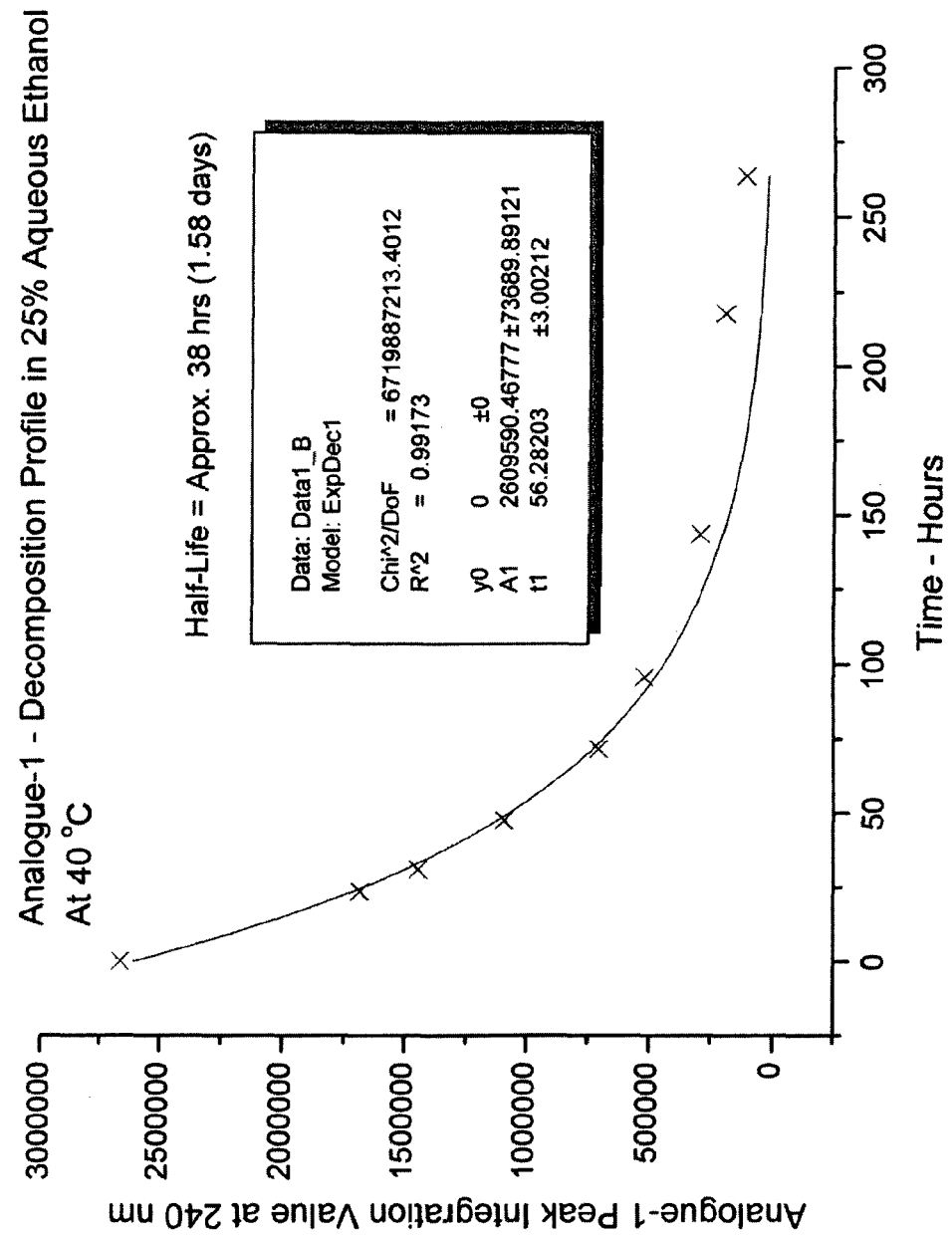
Figure 54:
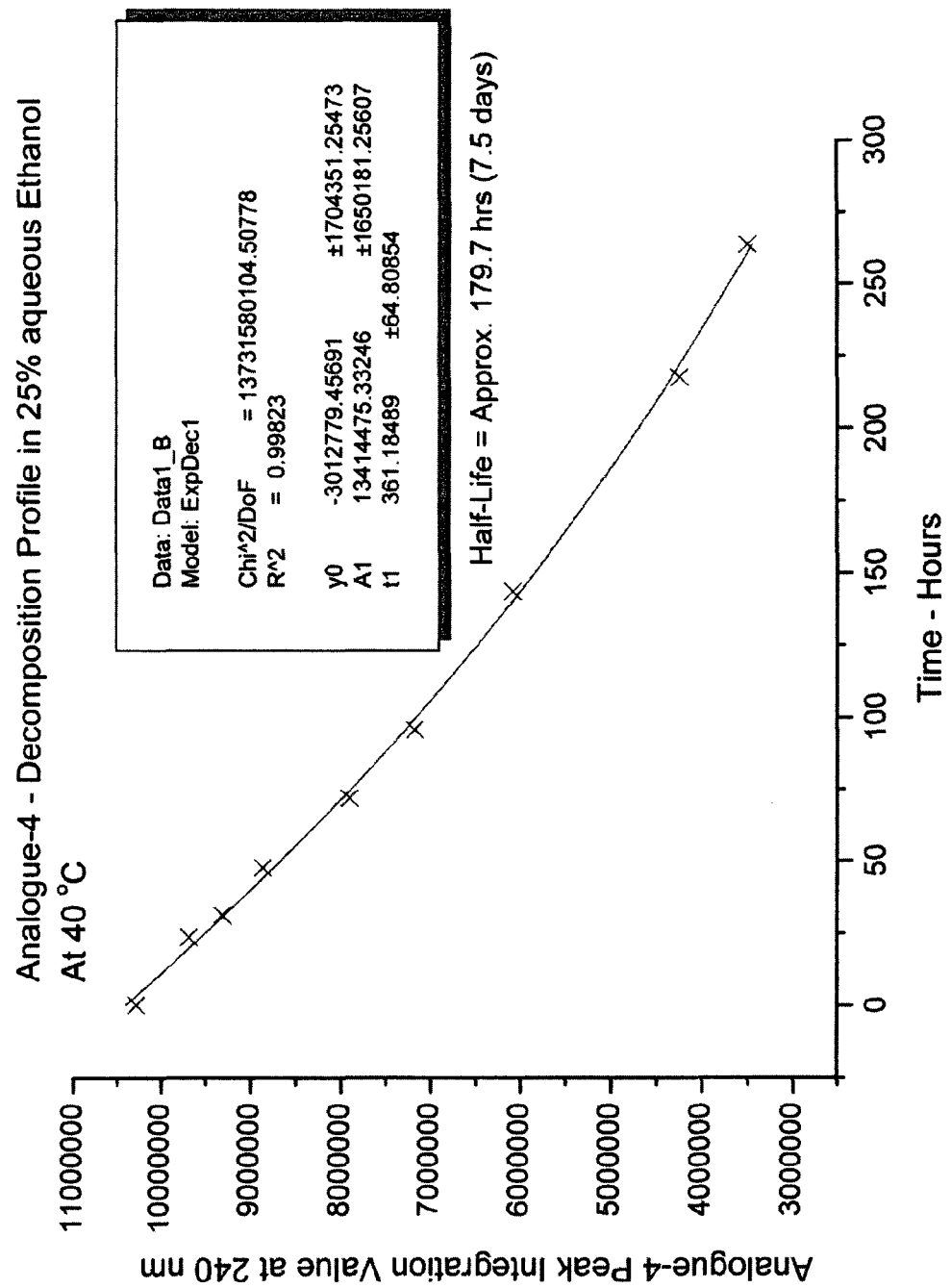
Figure 55:
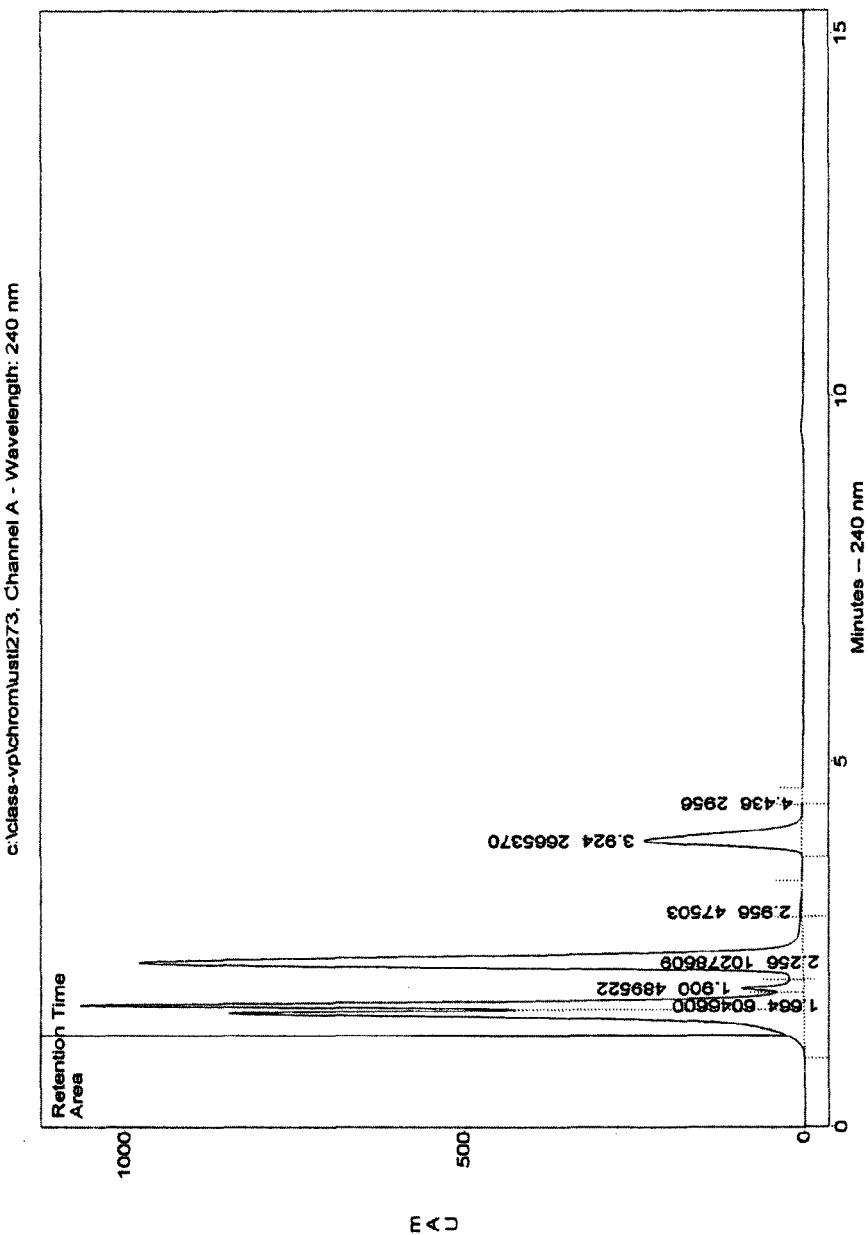

FIG. 53 shows a graph of the half-life of MAAM in 25% aqueous solution;

FIG. 54 shows a graph of the half-life of MMTSO in 25% aqueous solution;

FIG. 55 shows a chromatogram at time zero for: a reaction solution: [3.0 g GP+200 mg P-1+35 ml water] diluted to provide an ethanol content of 25% v/v. Chromatogram obtained immediately before sample stored at 40° C. Retention Times: Analogue-1 at 3.924 min, Analogue-4 at 2.256 min.

Figure 56:
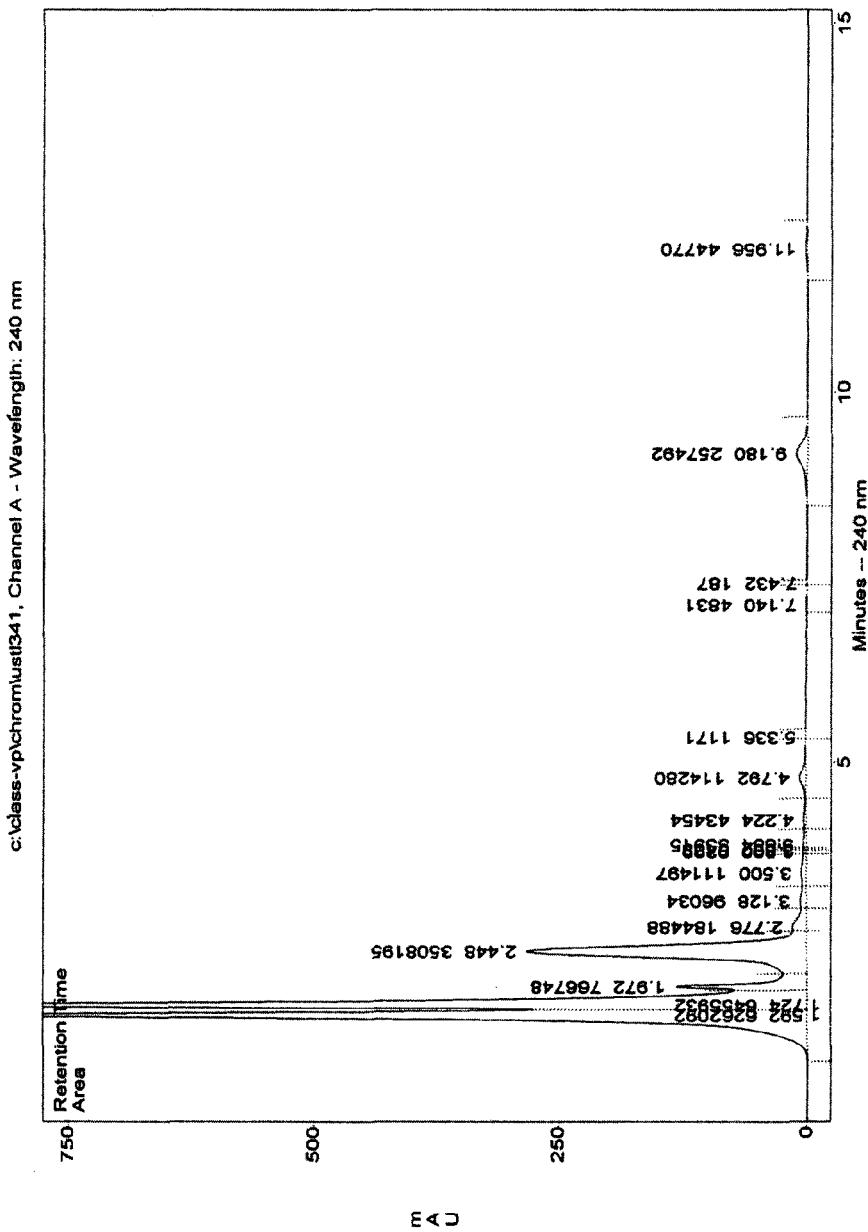

FIG. 56 shows a chromatogram for the same solution shown in FIG. 55: a reaction solution: [3.0 g GP+200 mg P-1+35 ml water] diluted to provide an ethanol content of 25% v/v. BUT Chromatogram now obtained after 263.5 hours sample stored at 40° C. Retention Times: Analogue-1 at 4.792 min, Analogue-4 at 2.448 min.

Figure 57:
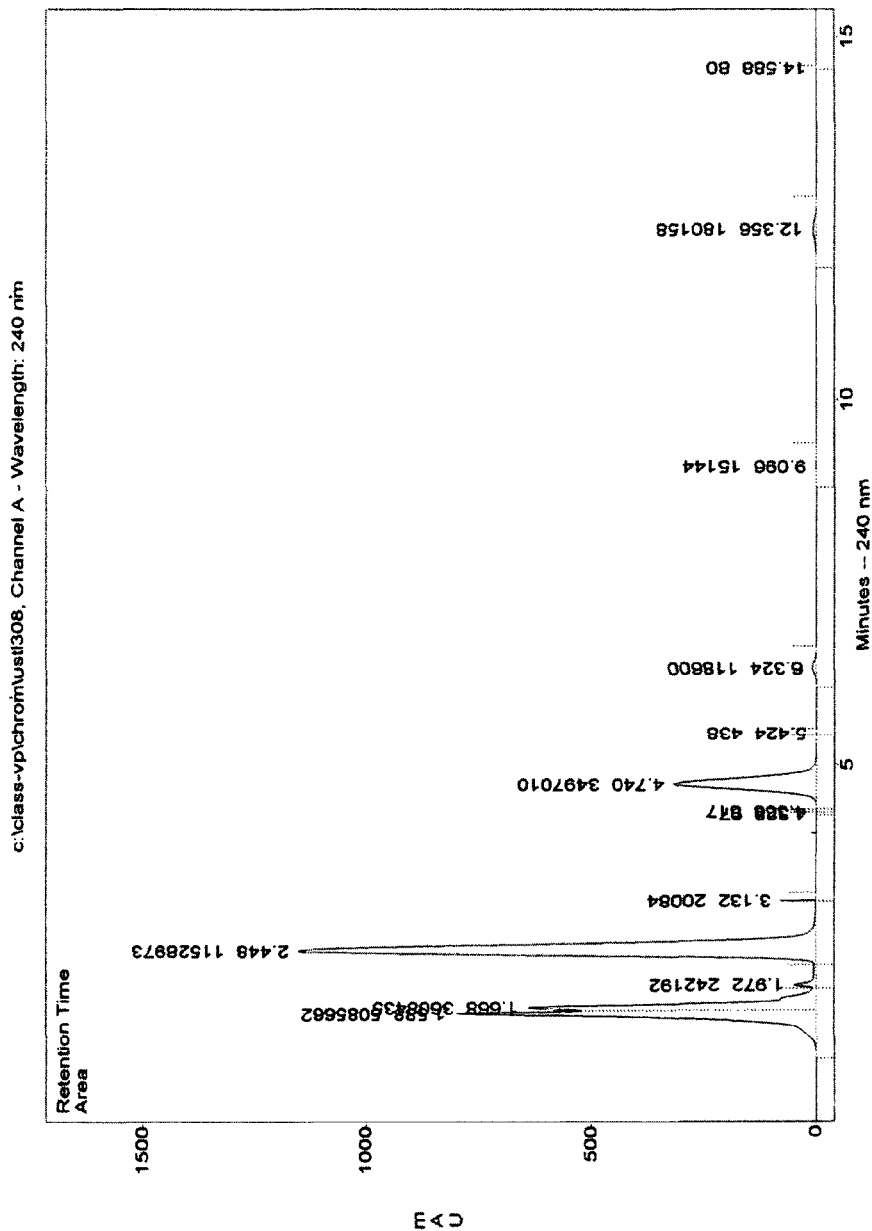

FIG. 57 shows a chromatogram obtained at time zero for a solution of 12.0 g FG (+400 mg P-1+70 ml water) before the solution was subjected to storage at 40° C.

Figure 58:
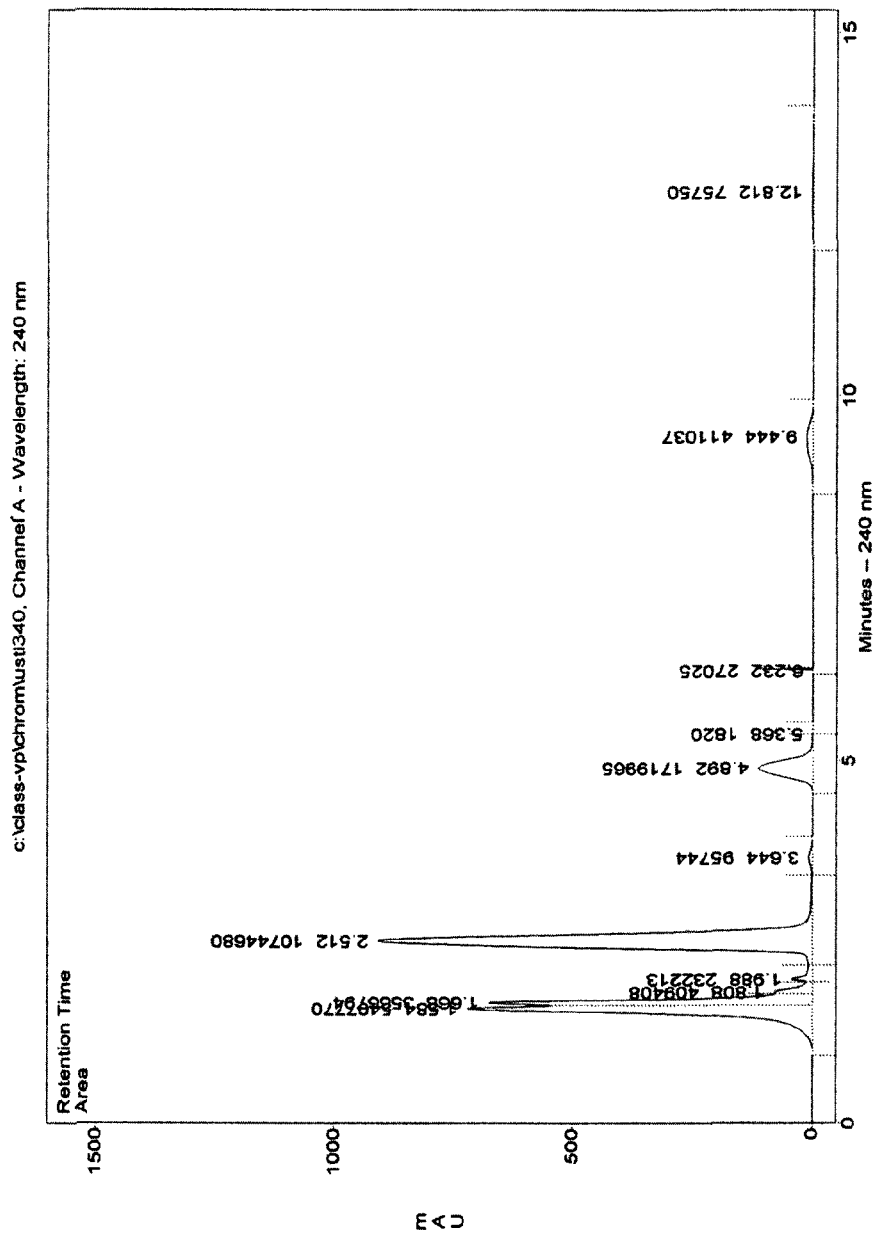
Figure 59:
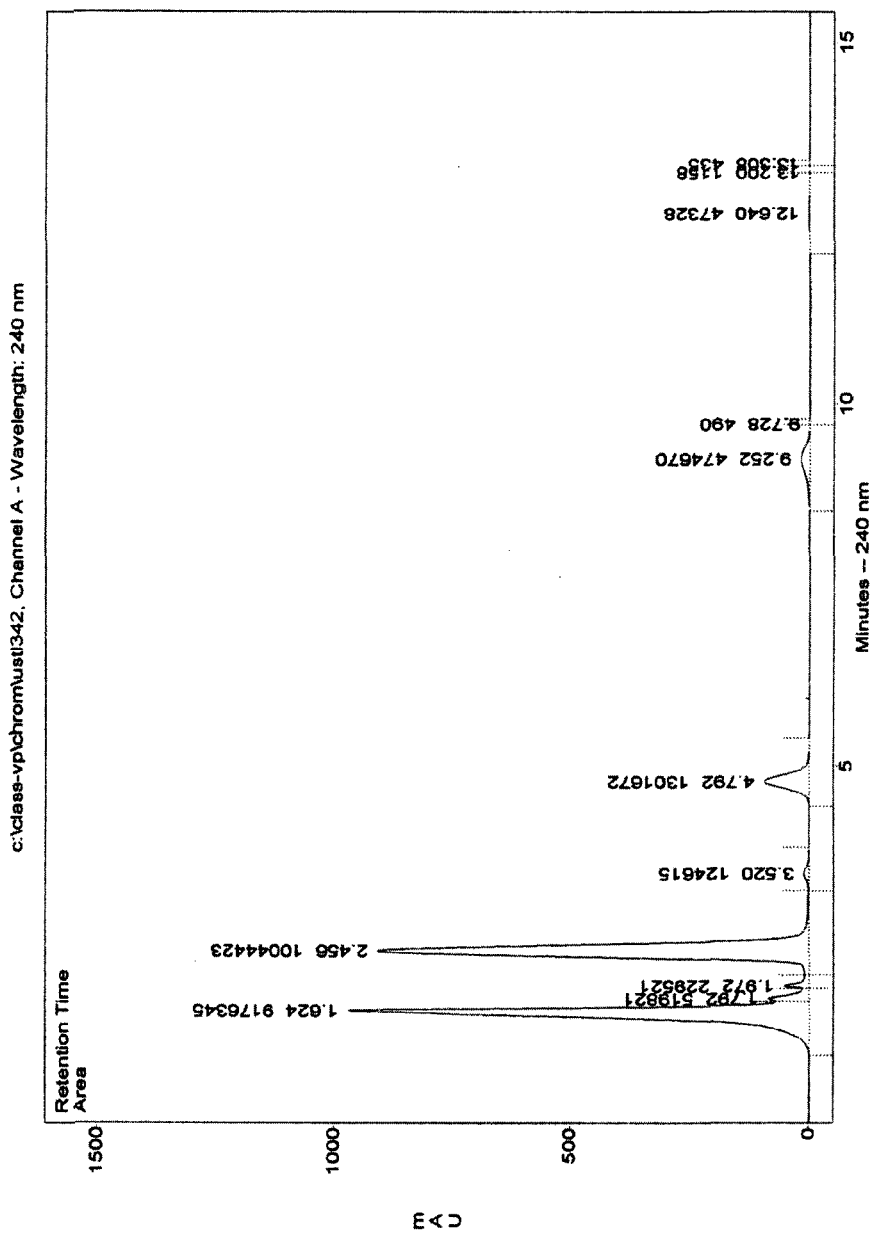
Figure 60:
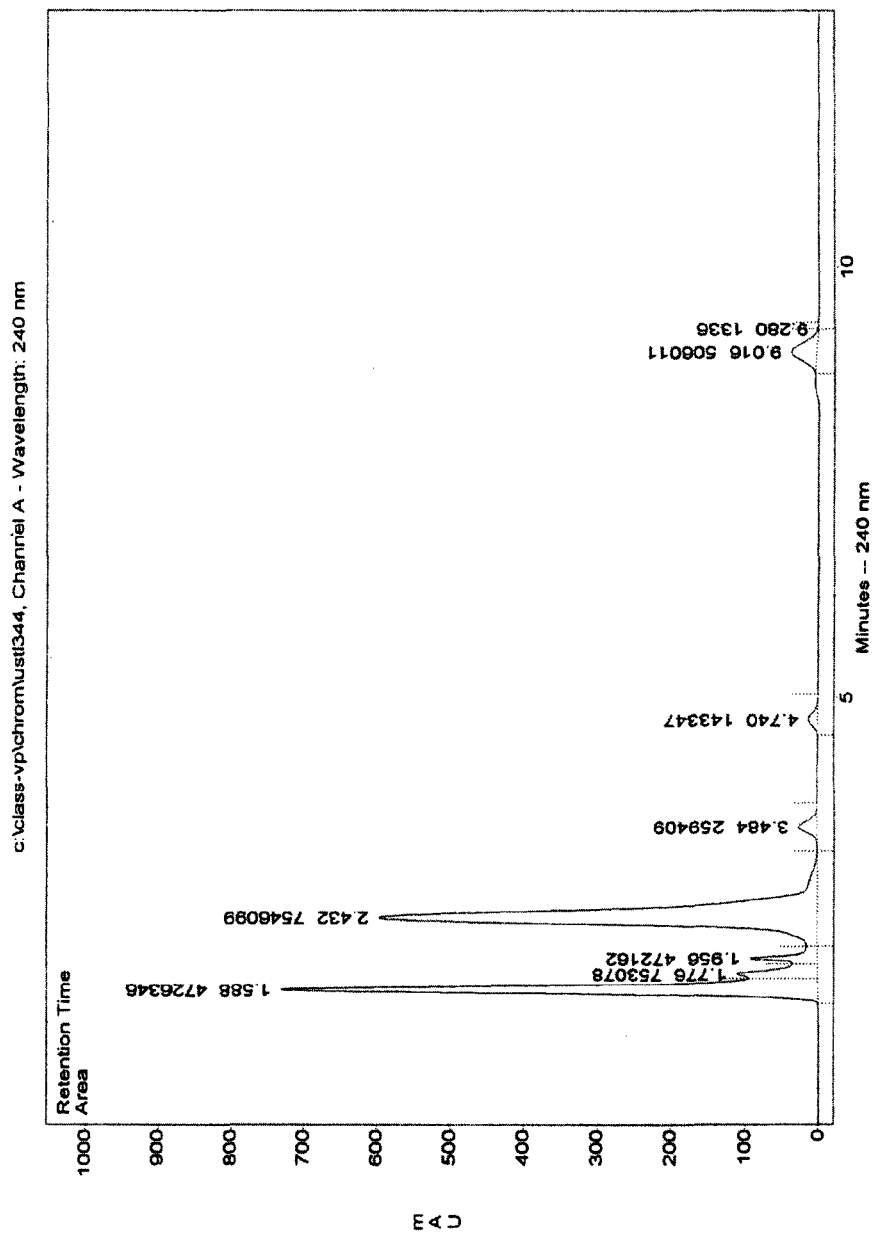
Figure 61:
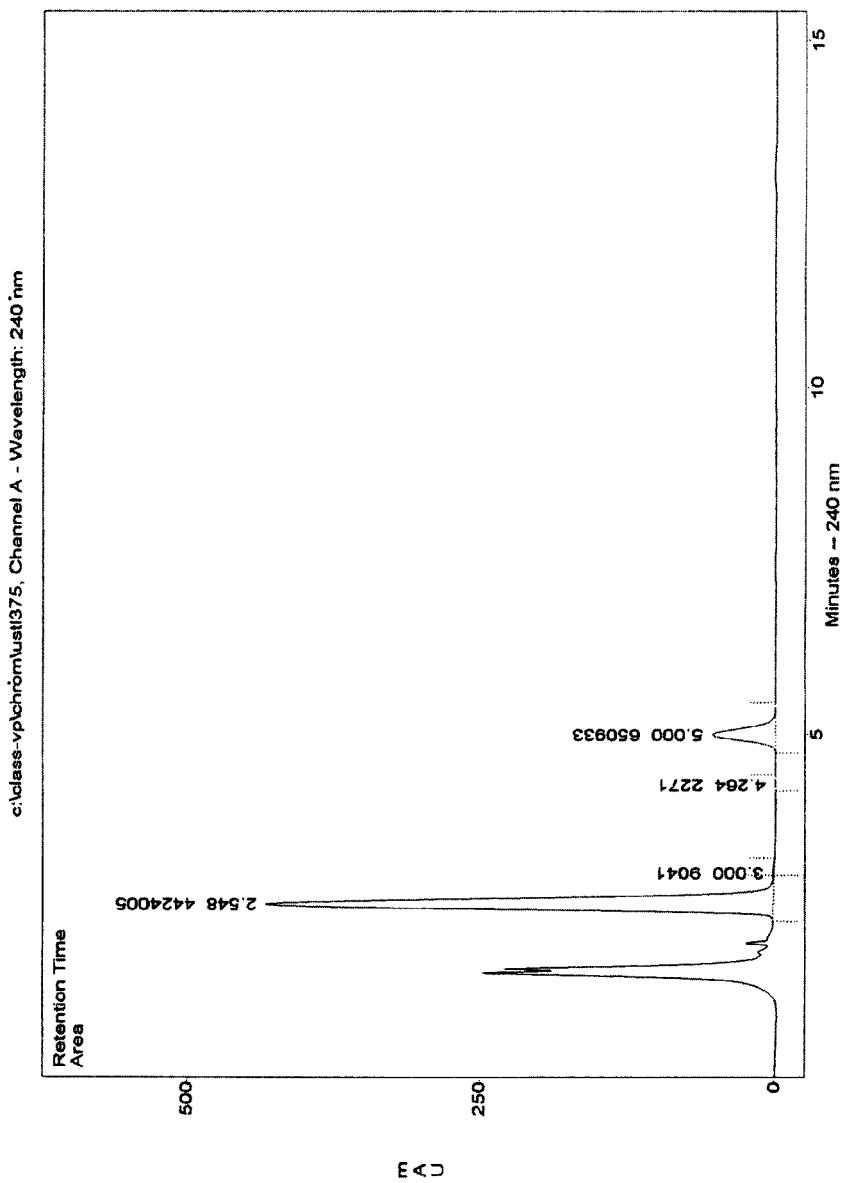
Figure 62:
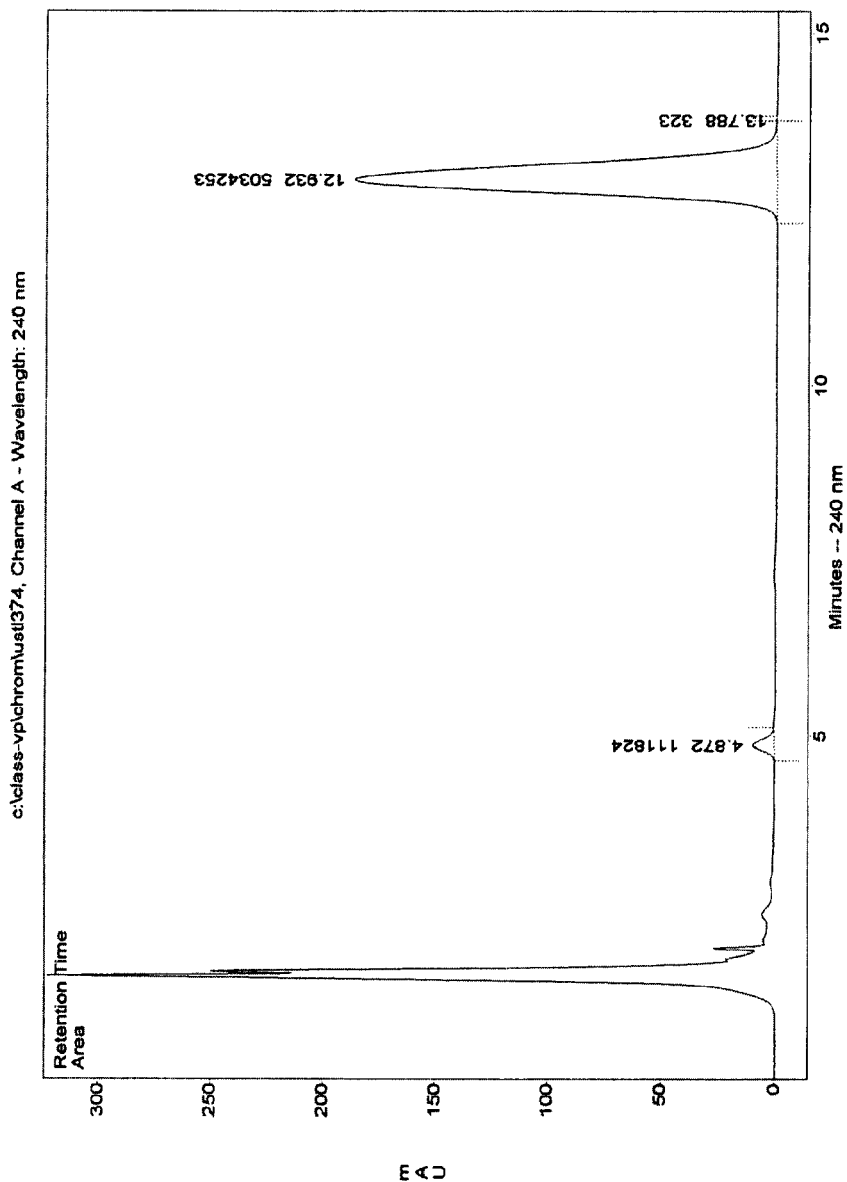
Figure 63:
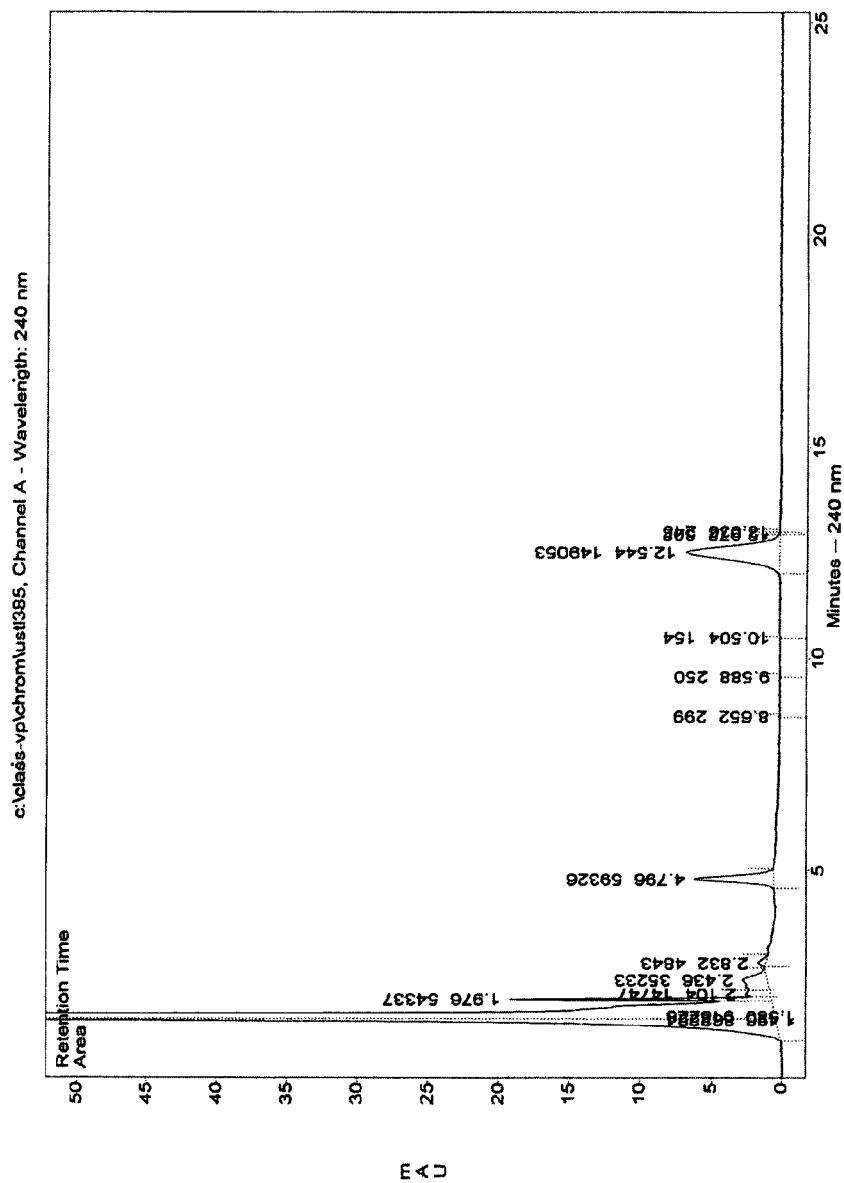
Figure 64:
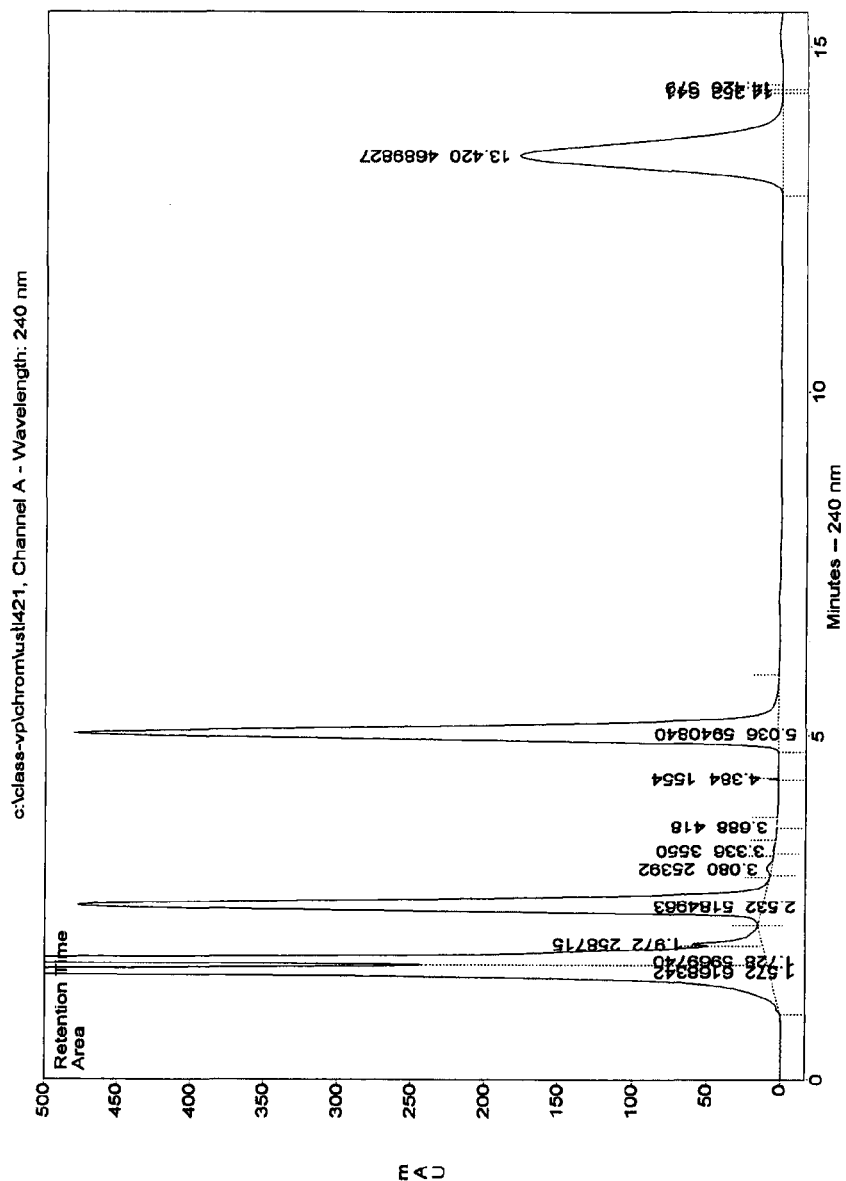
Figure 65:
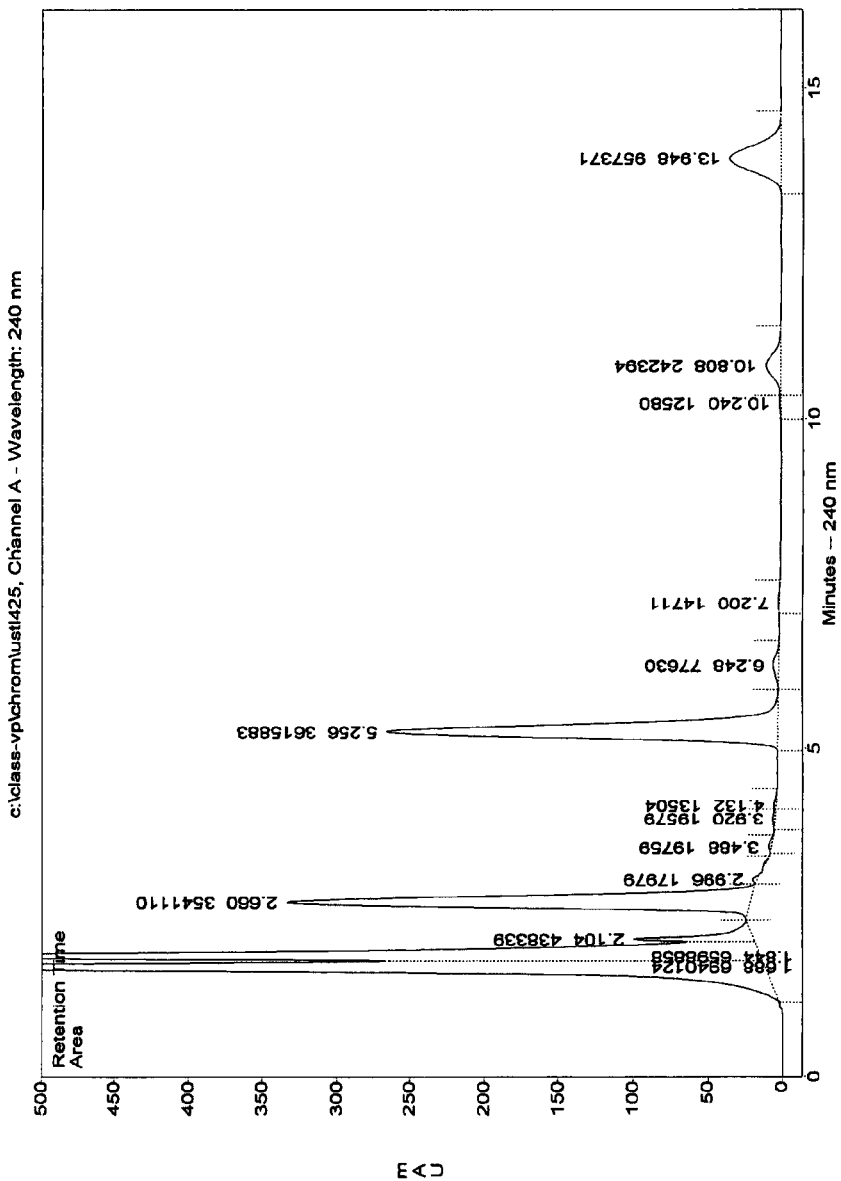
Figure 66:
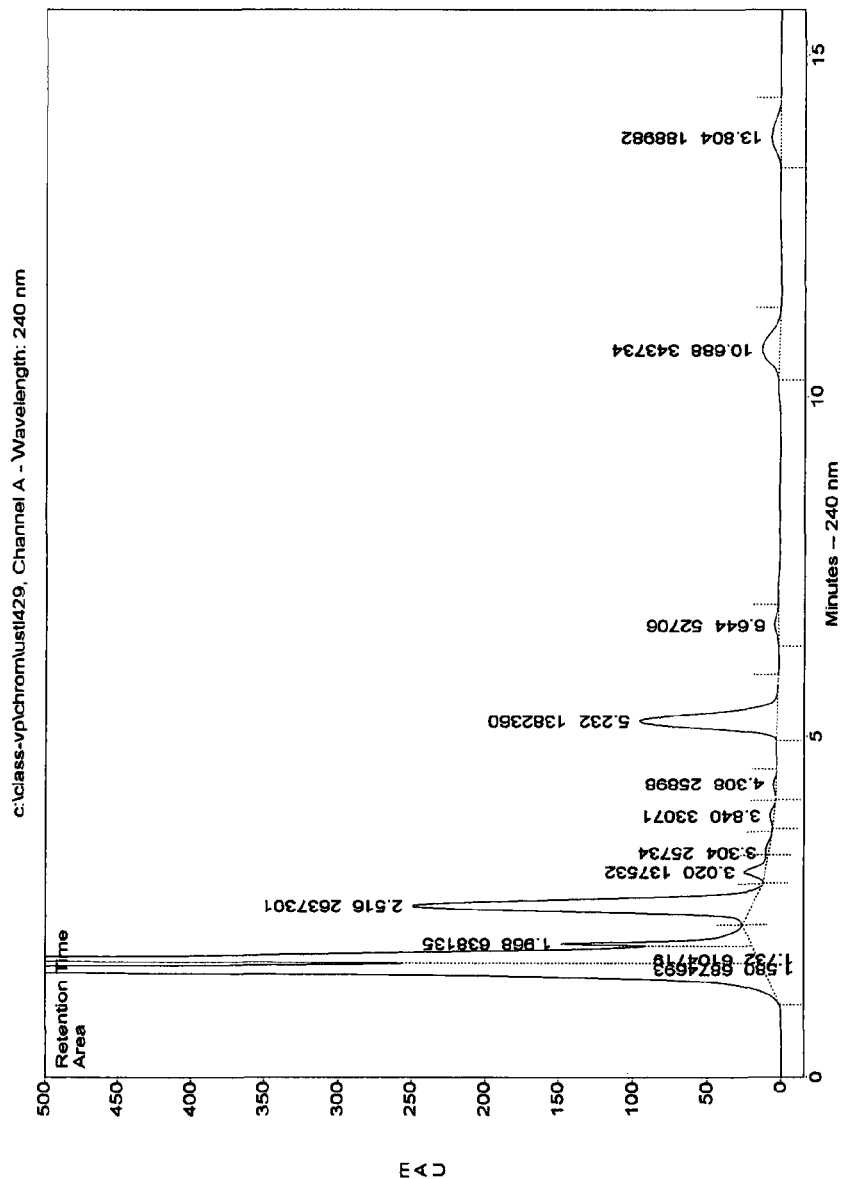
Figure 67:
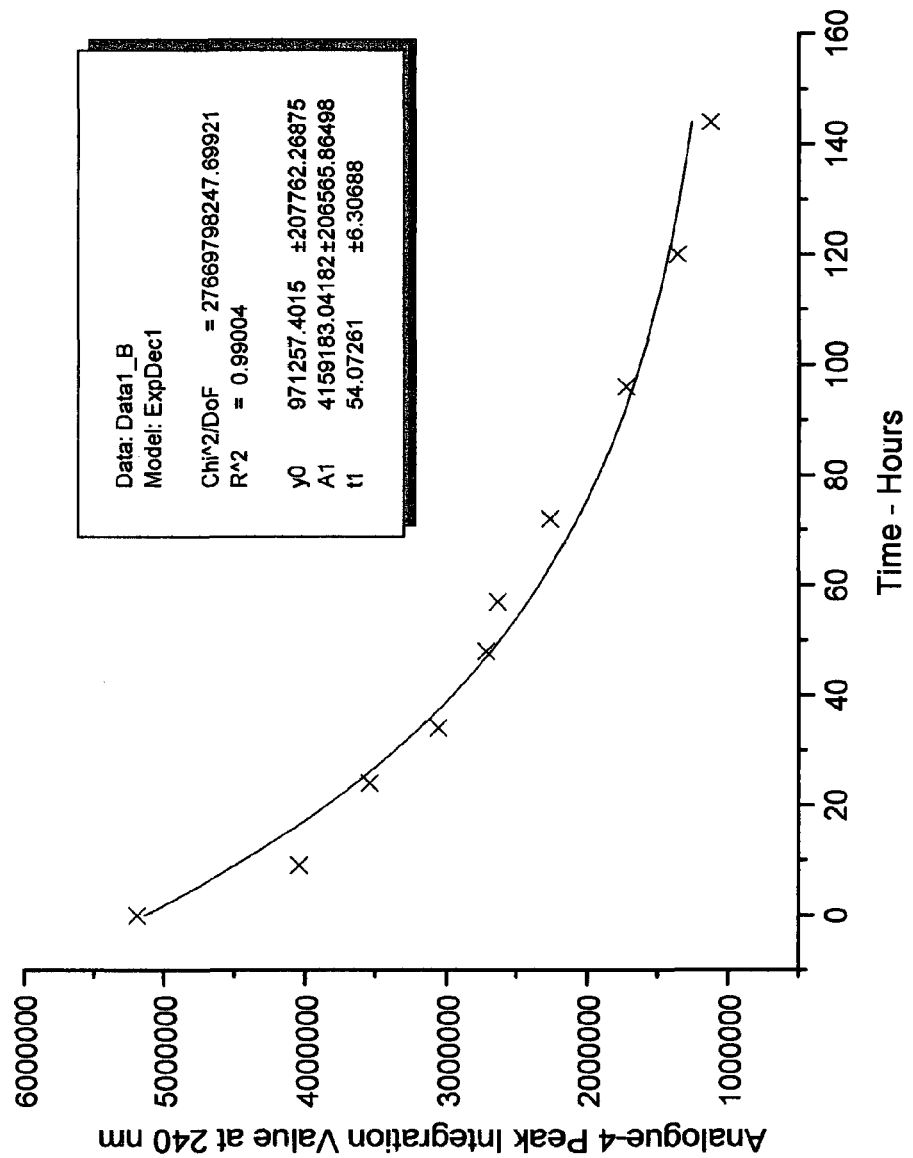

FIG. 58 shows a chromatogram obtained after 120 hours at 40° C. for the solution of FIG. 57;

FIG. 59 shows a chromatogram obtained after 168 hours at 40° C. for the solution of FIG. 57;

FIG. 60 shows a chromatogram obtained after 672 hours at 40° C. for the solution of FIG. 57;

FIG. 61 shows a chromatogram of a solution of MMTSO produced by dissolving 1.25 g of methiin in 400 ml of water then stirring in 5.7 g of garlic powder and continuing to stir for three hours;

FIG. 62 shows a chromatogram of a solution of Allicin produced by dissolving 1.25 g of alliin in 400 ml of water then stirring in 5.7 g of garlic powder and continuing to stir for three hours;

FIG. 63 shows a chromatogram of a solution produced by dissolving 5.7 g of garlic powder in water and stirring for three hours;

FIG. 64 shows a Chromatogram obtained at Time Zero (immediately prior to storage at 55° C.) for a Liquid Blend prepared from three Liquids in the following proportions [400 mg P-1+400 mg P-2+6 g GP+70 ml Water]—2 parts volume; [400 mg P-1+6 g GP+70 ml Water]—3 parts volume; [400 mg P-2+6 g GP+70 ml Water]—1 part volume;

FIG. 65 shows the chromatogram for the same blend as FIG. 64, after 24 hours storage at 55° C.;

FIG. 66 shows the chromatogram for the same blend as FIGS. 64 and 65 after 57 hours storage at 55° C.;

FIG. 67 shows a graph of the decomposition profile obtained for MMTSO in the 100% aqueous solution used to prepare the chromatograms of FIGS. 64-66 stored at 55° C.

Figure 68:
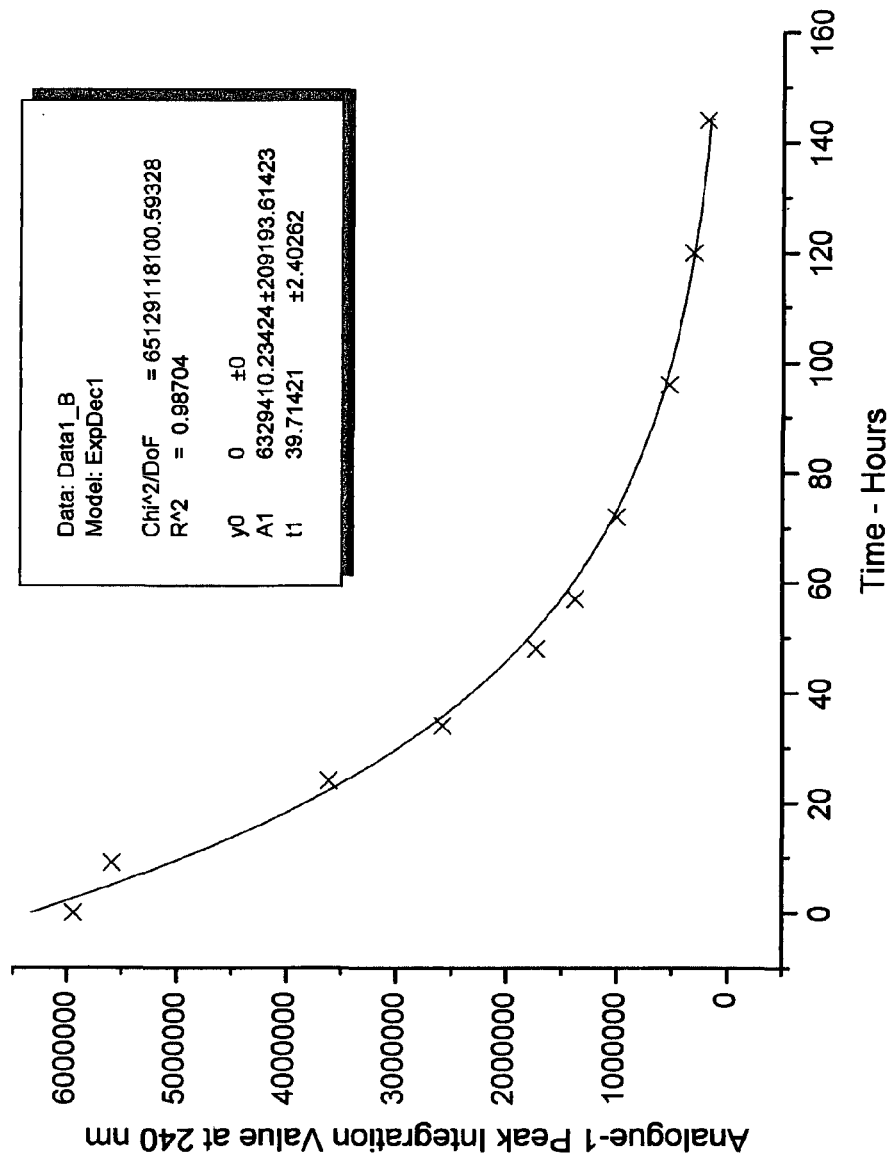

FIG. 68 shows a graph of the decomposition profile obtained for MAAM in the 100% aqueous solution used to prepare the chromatograms of FIGS. 64-66 stored at 55° C.

Figure 69:
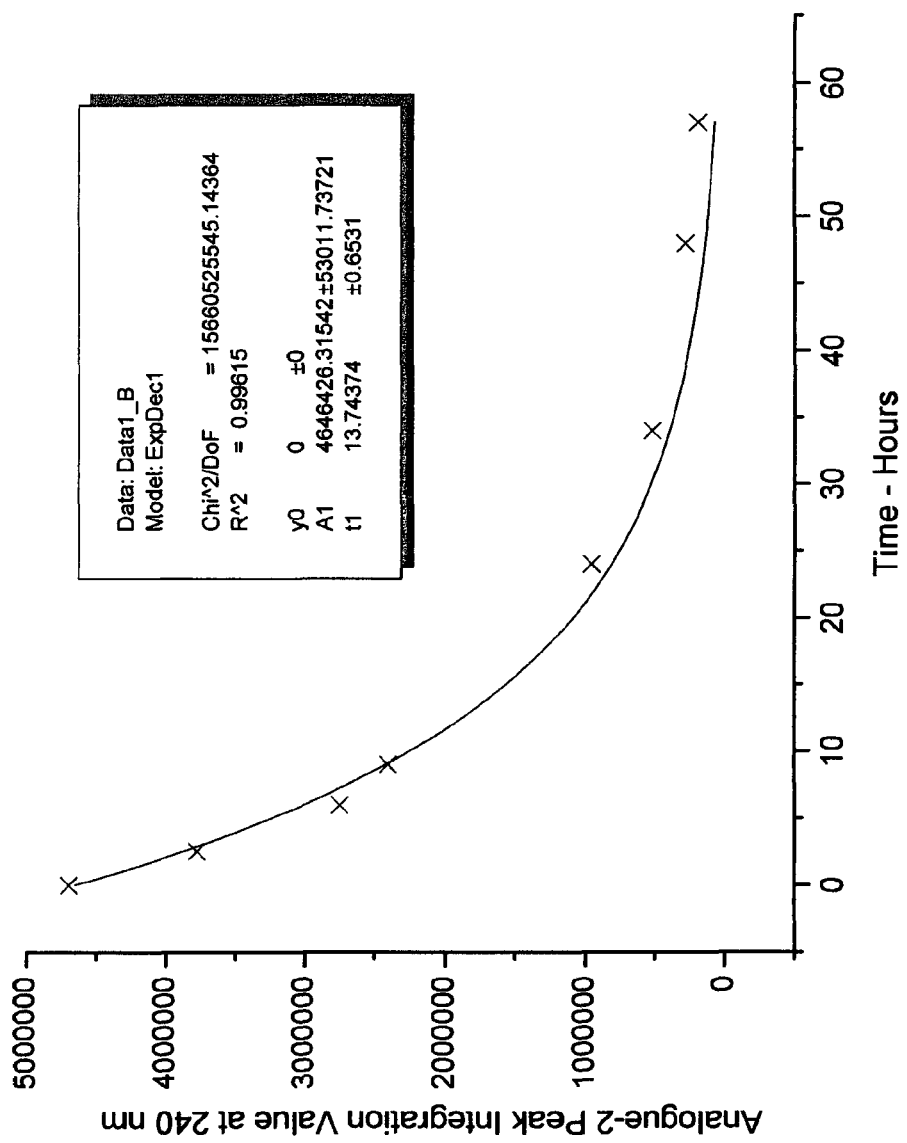

FIG. 69 shows a graph of the decomposition profile obtained for Allicin in the 100% aqueous solution used to prepare the chromatograms of FIGS. 64-66 stored at 55° C.

DETAILED DESCRIPTION OF THE INVENTION

In this specification, in discussions of chemical structures, "All" is used as a shorthand notation for an allyl moiety ($CH_2$=CH—$CH_2$—). For example, MeS(O)SAll is allyl methyl-thiosulfinate; and AllS(O)SMe is methyl allyl-thiosulfinate. In the HPLC analyses which follow, these two compounds elute substantially jointly. This mixture of compounds will also be described herein as a MA-AM mixture or Analogue-1, the MA and AM thiosulfinate structural isomers are analogues of allicin MA representing methyl allyl-thiosulfinate and AM representing allyl methyl-thiosulfinate.

The compound names methyl allyl thiosulfinate, allyl methyl thiosulfinate, allyl allyl thiosulfinate (which is allicin) and methyl methyl thiosulfinate can also alternatively be written as methyl allyl-thiosulfinate, allyl methyl-thiosulfinate, allyl allyl-thiosulfinate and methyl methyl-thiosulfinate, respectively.

Moreover, in this specification the compounds are sometimes referred to as analogues, in which:

Analogue-1 is a mixture of methyl allyl-thiosulfinate (MA) and its structural isomer allyl methyl-thiosulfinate (AM). These isomers are not separated by the reverse phase HPLC method that has provided all the chromatograms.

Analogue-2 is allyl allyl-thiosulfinate commonly known via its trivial name allicin.

Analogue-3 is 1-propenyl allyl-thiosulfinate and exists in E,Z geometric isomer forms.

Analogue-4 is methyl methyl-thiosulfinate, also known as methyl methanethiosulfinate and by the abbreviation MMTSO (whose structural formula is CH3-S(O)—S—CH3 and whose abbreviation is MeS(O)SMe).

Experimental

Method of Manufacturing an Allicin Containing Water Extracts Containing an Enhanced Relative Quantity of MeS(O)SAll and AllS(O)SMe Thiosulfinates.

Process 1

This method uses raw garlic and high purity water to provide an aqueous extract of garlic that will provide a 750-1650 ppm allicin content with a relatively significant MeS(O)SAll and AllS(O)SMe (MA-AM) content.

The outer skin of garlic bulbs was removed and the bulbs split into individual cloves, washed in water and coarsely chopped using a conventional food-processor. The chopped garlic was left at 20° C. for 5-20 minutes (typically 15 minutes); and then mixed with ultra-pure drinking water at a temperature of 4° C., with mixing for 5 minutes at a ratio of 0.6 kg garlic with 1 liter of water. The chopped garlic-water slurry was then rapidly frozen at −20° C. After 12-24 hours the frozen chopped garlic-water slurry was allowed to thaw at 10° C. Immediately after the slurry was completely thawed, it was coarsely filtered and the resultant aqueous garlic extract filtered through stacked sieves: top sieve with 250 micron mesh, lower sieve with 125 micron mesh.

The aqueous garlic extract was then placed into a settling vessel and allowed to stand for 24 hours at 0-4° C. during which period any unfiltered garlic tissue fines were allowed to settle. The supernatant liquid was then drawn away from the settling vessel such that the garlic fines were substantially separated. An aliquot of the settled liquid was then submitted for HPLC analysis.

Using the preceding steps, a garlic extract whose allicin concentration is in the range 750-1650 ppm was produced. The integrated peak area obtained for the MeS(O)SAll and AllS(O)SMe thiosulfinates (MA-AM mixture), separated as a single peak using the HPLC conditions below, should provide a value of between 15-50% of the integrated peak area obtained for allicin. Typically, this value will be 20-40% of the allicin peak area. The peak integration ratios quoted relate to a chromatogram obtained with detection at 240 nm.

If the allicin concentration is below 1000 ppm and/or the relative reverse phase HPLC peak area for the MeS(O)SAll and AllS(O)SMe (measured as a single peak) falls below a desired value in the range 15-50% relative peak area to that obtained for allicin, aqueous garlic extract that has been concentrated by fractional freezing may be added such that the desired allicin and MeS(O)SAll and AllS(O)SMe concentrations are obtained as measured by quantitative reverse phase HPLC assay.

Process 2

This step produces a concentrated aqueous extract of garlic and, typically provide an allicin concentration in the range 2000-4000 ppm. The typical associated range of the concentrated MA-AM thiosulfinates (collectively assayed) being in the range 400-2000 ppm.

Aqueous garlic extract solution was prepared according to Process 1 above up to and including separation of the garlic fines.

The liquid was then placed into a cylindrical container, open at one end, and in an upright position is frozen at −20° C. until ice formation was complete. The cylinder containing the frozen aqueous garlic extract solution was then inverted in a stand with a cold collection vessel placed below the open end of the container containing the frozen aqueous garlic extract.

Since allicin and MeS(O)SAll and AllS(O)SMe have lower freezing points than water, once the frozen aqueous garlic extract starts to thaw a viscous liquid (typically yellow-orange brown) enriched in thiosulfinate content starts to percolate through the main body of ice. The concentrated liquid is collected typically such that 25-40% of the original liquid sample volume that was frozen is isolated.

The collected liquid was periodically assayed for allicin and relative MeS(O)SAll and AllS(O)SMe concentration. The first stage concentrated thiosulfinate containing liquid can, in turn, be frozen at −20° C. and the process through the freezing and thawing stages can be repeated to bring about a second stage of thiosulfinate concentration by the process of fractional freezing.

The concentrated allicin liquid that is used to adjust the allicin and MeS(O)SAll and AllS(O)SMe is typically prepared in the range 2400-4000 ppm with respect to allicin content concentration with the collective MeS(O)SAll and AllS(O)SMe concentration typically in the range 550-2000 ppm.

Reverse Phase HPLC Conditions

HPLC column: 150×4.6 mm Agilent C-18 column fitted with 10×2 mm C-18 precolumn.
HPLC mobile phase: 34:66 methanol:water by % volume.
Detection: diode-array detection.

Figure 1:
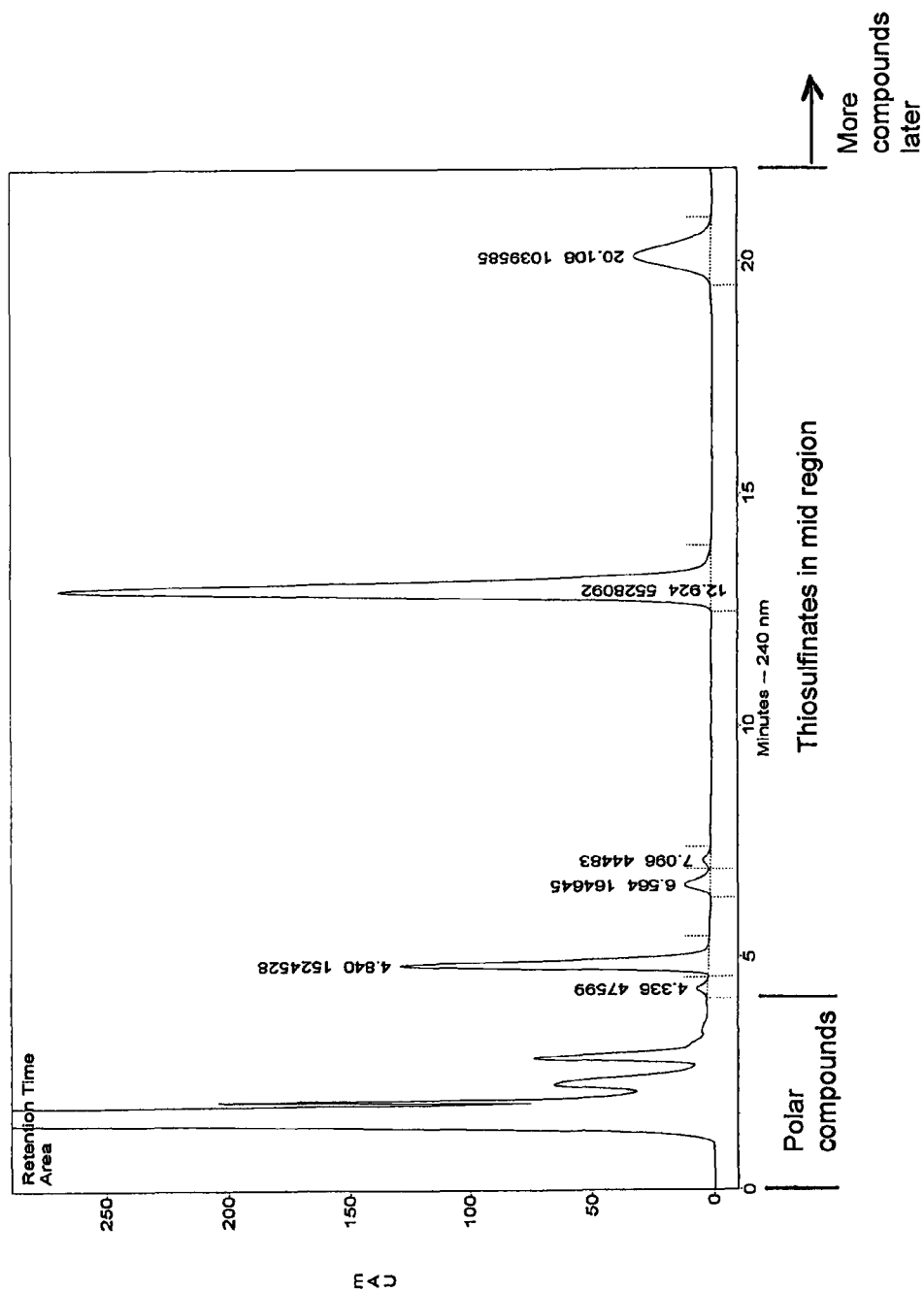
FIG. 1 is a HPLC profile of an aqueous garlic extract manufactured according to Process 1. Peak at retention time 4.840 minutes is MeS(O)SAll and AllS(O)SMe (collectively, the structural isomers are referred to as Analogue-1), peak at retention time 12.924 minutes is allicin (Analogue-2). The peak at retention time 20.108 minutes is 1-propenyl-(E,Z) allyl-thiosulfinate, [whose structural formula is: $CH_2=CH-CH_2-S(O)-S-CH=CH-CH_3$ whose abbreviation is AllS(O)SPn-(E,Z) and whose geometric isomers are collectively referred to as Analogue-3]. HPLC profile of an aqueous garlic extract manufactured according to Method 1. Peak at retention time 4.840 minutes is MeS(O)SAll and AllS(O)SMe (collectively referred to as Analogue-1), peak at retention time 12.924 minutes is allicin (Analogue-2) and peak at retention time 20.108 minutes is AllS(O)SPn-(E,Z) (Analogue-3).

A typical chromatogram obtained for reverse phase HPLC analysis of an aqueous garlic extract prepared according to Process 1 is given in FIG. 1. The species that are partially or fully separated in the chromatogram fall into three categories: (1) predominantly polar species such as water soluble pigments and amino acids in the retention time window 0-4 minutes; (2) thiosulfinates, predominantly present in the retention time window 4-25 minutes; and (3) breakdown products of thiosulfinates such as ajoenes (detected at retention times greater than 25 minutes). Using diode-array HPLC procedures and LC-MS procedures it was found that an aqueous garlic extract prepared according to Process 1 produces an extract relatively rich in: methyl allyl-thiosulfinate [whose structural formula is $CH_2=CH-CH_2-S(O)-S-CH_3$ also represented as AllS(O)SMe], allyl methyl-thiosulfinate [whose structural formula is $CH_3-S(O)-S-CH_2-CH=CH_2$ also represented as MeS(O)SAll], allicin [whose structural formula is $CH_2=CH-CH_2-S(O)-S-CH_2-CH=CH_2$ also represented as AllS(O)SAll] and 1-propenyl allyl-thiosulfinate [whose structural formula is $CH_2=CH-CH_2-S(O)-S-CH=CH-CH_3$ also represented as AllS(O)SPn-(E,Z) with the 1-propenyl group resulting in the possibility of E,Z geometric isomers] whose peaks are not resolved by reverse phase HPLC. The two structural thiosulfinate isomers MeS(O)SAll and AllS(O)SMe are unresolved using reverse phase HPLC and produce a single peak at retention 4.840 minutes in FIG. 1. The peak detected at 12.924 minutes in FIG. 1 is allicin [AllS(O)SAll]. The peak detected at retention time 20.106 minutes in FIG. 1 is 1-propenyl allyl-thiosulfinate possibly being composed by either one of the E,Z isomers or a mixture of the E,Z geometric isomers.

Although the half-life of allicin in aqueous solution has been reported no such measurements have been previously reported for the following thiosulfinates: MeS(O)SAll, AllS(O)SMe and AllS(O)SPn-(E,Z).

The half-lives for MeS(O)All and AllS(O)SMe (jointly measured), AllS(O)SAll and AllS(O)SPn-(E,Z), determined by quantitative reverse phase HPLC, are now revealed in this patent application and have been measured for aqueous garlic extracts diluted with ethanol to provide water:ethanol solutions with ethanol content ranging from 25%, 50% and 75% by percentage volume. The solutions were prepared from a single stock aqueous garlic extract solution that was diluted with the appropriate volume of ethanol to produce the 25%, 50% and 75% ethanol garlic aqueous extract solutions. The aqueous stock solution of garlic extract assayed by HPLC was determined to have an allicin content of 1600 ppm (1600 mg allicin in 1000 ml water) and each of the 25%, 50% and 75% ethanol:aqueous dilutions prepared from the aqueous garlic extract stock solution were prepared to provide an initial allicin concentration of 400 ppm. In order to gather statistical data relevant to determining the precision of the mean half-life measurements of the thiosulfinate Analogues, each 25%, 50% or 75% ethanol content sample was prepared in triplicate and separately aged at the specified temperature and separately analysed at appropriate time intervals after the samples had commenced storage at a specific accurately controlled temperature.

The decomposition profiles of MeS(O)SAll and AllS(O)SMe (the MA-AM mixture collectively referred to as Analogue-1), AllS(O)SAll (Allicin, Analogue-2) and AllS(O)SPn-(E,Z) (Analogue-3) thiosulfinates were then determined by quantitative reverse phase HPLC. The quantitative HPLC procedure involved determining the relative concentrations of each thiosulfinate in the various solutions at the various ageing temperatures as a function of the time that each solution was stored at a carefully controlled temperature. The initial measurement of the concentration value for each thiosulfinate determined immediately after freshly prepared solutions were prepared provides the 100% thiosulfinate concentration value for the start time (time zero) at which the time-lapse thermal decomposition measurements started to commence.

Figure 2:
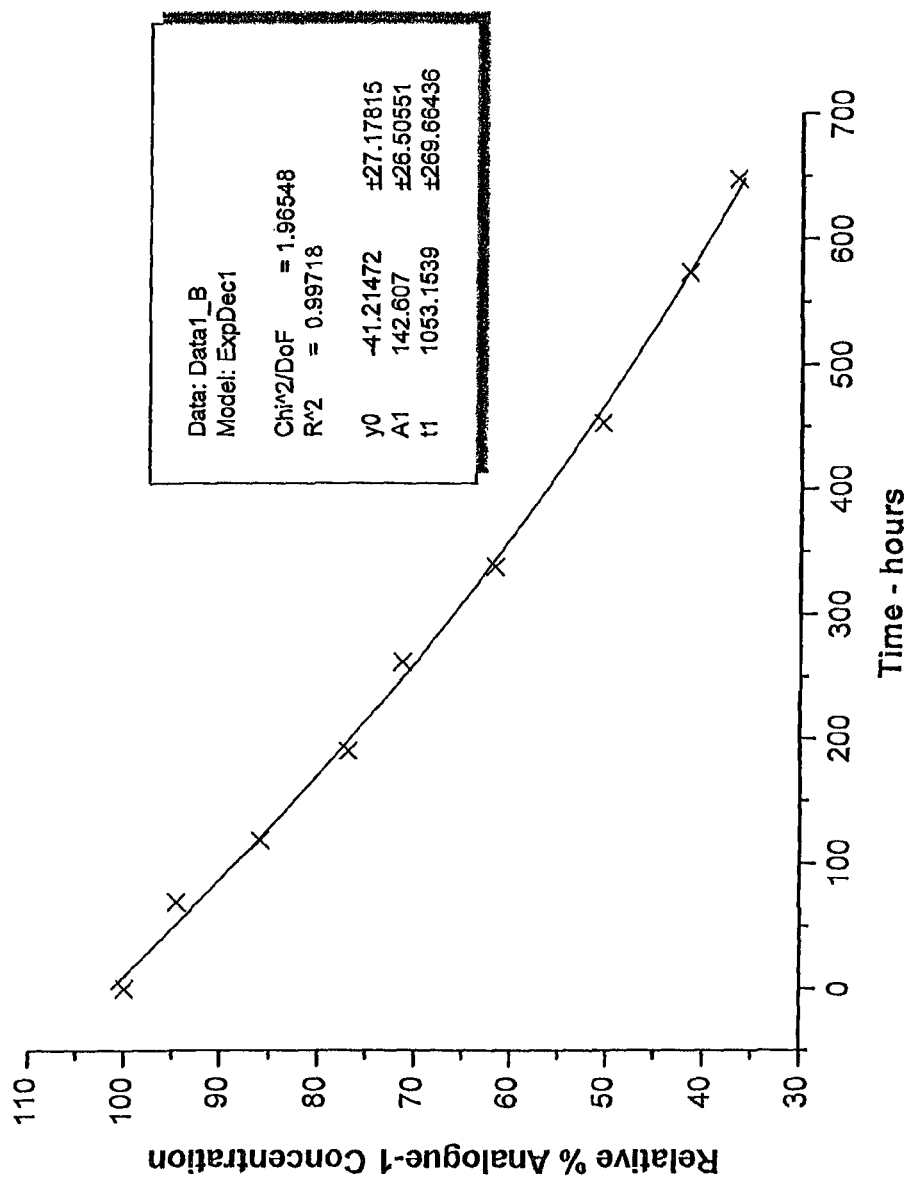
FIG. 2 is an exponential first order decay profile obtained for MeS(O)SAll and AllS(O)SMe. Data obtained by quantitative reverse phase HPLC analysis method. Best fit graph calculated using ORIGIN® version 6.1 software. Analogue-1 decomposition profile in 25% ethanol at 20° C. Example of exponential first order decay profile obtained for MeS(O)SAll and AllS(O)SMe (collectively referred to as Analogue-1). Data obtained by quantitative HPLC and is derived from one of three triplicate samples made up with 25% ethanol and stored at 20° C. Best fit graph calculated using ORIGIN® version 6.1 software (OriginLab Corporation).
Figure 3:
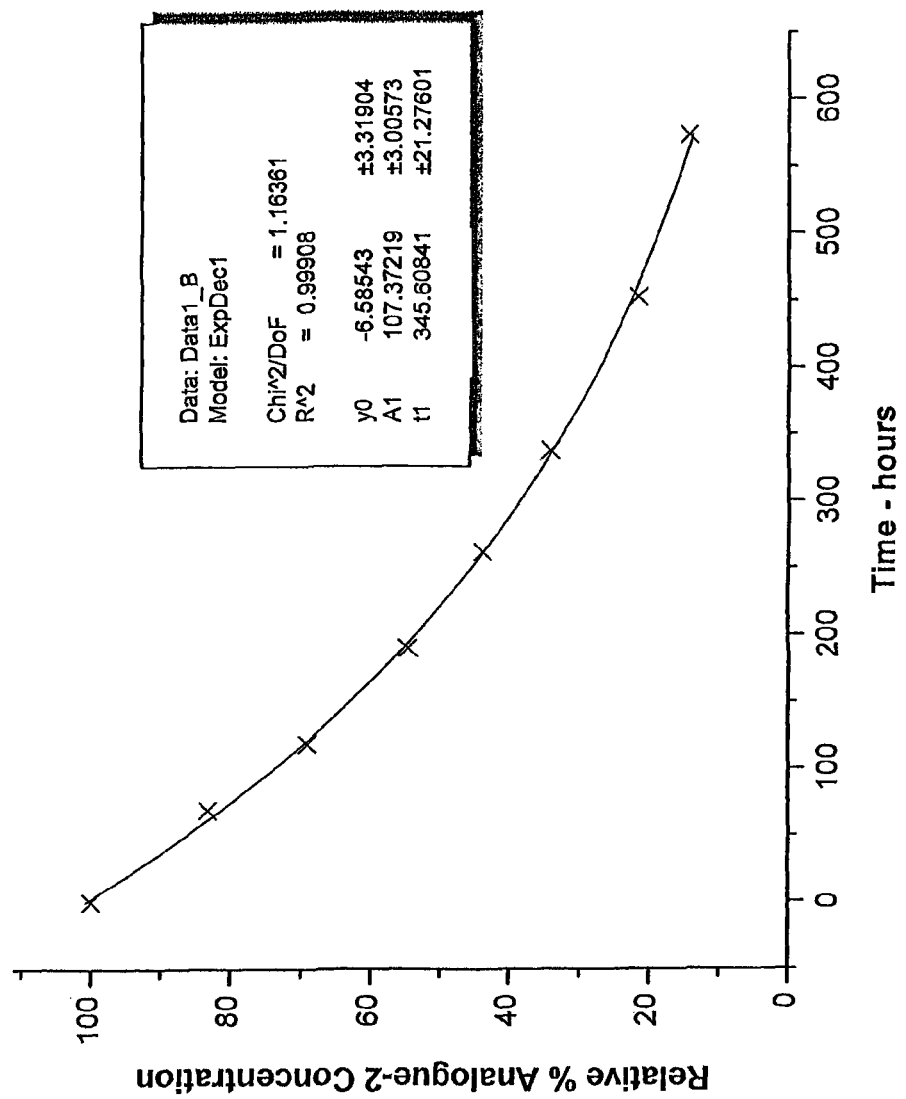
FIG. 3 is an exponential first order decay profile obtained for allicin. Data obtained by quantitative reverse phase HPLC analysis method. Best graphical fit calculated using ORIGIN® version 6.1 software. Analogue-2 decomposition profile in 25% ethanol at 20° C. Example of exponential first order decay profile obtained for AllS(O)SAll (allicin also referred to as Analogue-2). Data obtained by quantitative HPLC and is derived from one of three triplicate samples made up with 25% ethanol and stored at 20° C. Best fit graph calculated using ORIGIN® version 6.1 software (OriginLab Corporation).
Figure 4:
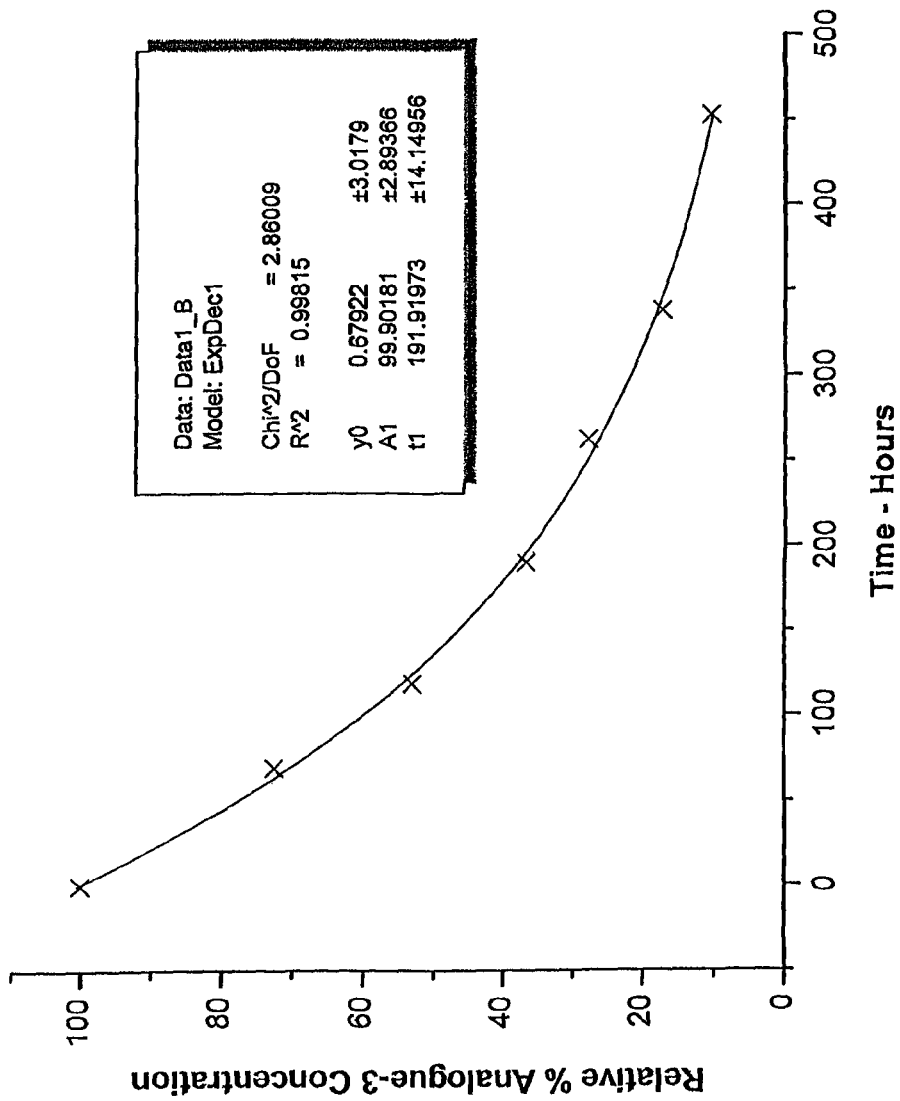
FIG. 4 is an exponential first order decay profile obtained for AllS(O)SPn-(E,Z). Data obtained by quantitative reverse phase HPLC analysis method. Best graphical fit calculated using ORIGIN® version 6.1 software. Analogue-3 decomposition profile in 25% ethanol at 20° C. Example of exponential first order decay profile obtained for AllS(O)SPn-(E,Z) (the E and Z geometric isomers are collectively referred to as Analogue-3). Data obtained by quantitative HPLC and is derived from one of three triplicate samples made up with 25% ethanol and stored at 20° C. Best fit graph calculated using ORIGIN® version 6.1 software (OriginLab Corporation).

The quantitative HPLC data recorded for the MA-AM mixture (Analogue-1), allicin (Analogue-2) and AllS(O)SPn-(E,Z) (Analogue-3) established that each thiosulfinate was subject to a first-order exponential decay process when the 25%, 50% and 75% aqueous:ethanol garlic extract solutions were stored (aged) through the temperature range 40-20° C. FIGS. 2-4 show exponential decay profiles obtained for MA-AM (Analogue-1), allicin (Analogue-2) and AllS(O)SPn-(E,Z) (Analogue-3)—FIGS. 2-4 produced from data obtained from the HPLC analyses of the same single sample whose solvent composition was ethanol:water (25:75% by volume) with an initial allicin concentration of 400 ppm. The decay profiles were obtained using ORIGIN version 6.1 software (Origin is a registered trade mark of OriginLab Corporation) software that determined the best fit for decomposition profiles as being first-order exponential decay. From the decomposition profiles shown in FIGS. 2-4 it is possible to interpolate to determine the time required for each thiosulfinate to decompose to 50% of its initial concentration level that had been initially measured at the outset when controlled temperature storage started. Thus, FIGS. 2-4 can be used to calculate half-life values for the thiosulfinates defined as being Analogues 1-3 for one of the 3 samples containing 25% ethanol that had been stored accurately at 20° C.

Table 3 provides the half-life data recorded for MeS(O)SAll and AllS(O)SMe (Analogue-1), allicin (Analogue-2) and AllS(O)SPn-(E,Z) (Analogue-3).

AllS(O)SPn-(E,Z). The results are shown in Table 4 that also includes half-life data for the thiosulfinates determined in a 100% aqueous garlic extract solution aged at 20° C. with an initial allicin concentration equivalent to 1500 ppm.

TABLE 4

Thiosulfinate half-lives in 100% aqueous solution prepared from garlic according to Method 1. The 375 ppm allicin concentration solution was prepared by diluting the garlic extract solution that provided 1500 ppm allicin concentration.

| Initial Allicin (A-2) Concentration | Half-Life (hours) at 20° C. |
|---|---|
| 375 ppm | A-1 = 487.4 (13.5) |
|  | A-2 = 228.2 (13.7) |
|  | A-3 = 140.4 (4.5) |
| 1500 ppm | A-1 = 300.9 (10.1) |
|  | A-2 = 133.5 (2.3) |
|  | A-3 = 77.2 (1.6) |

Identities of A-1, A-2 and A-3 previously specified in Table 3 caption. Mean half-life values and standard deviation values in parentheses determined from analyses of three separate samples prepared at each initial allicin concentration level. Standard deviation values calculated using (n − 1) degrees of freedom.

Tables 3 and 4 demonstrate that both MeS(O)SAll and AllS(O)SMe possess significantly longer half-lives than allicin in aqueous ethanol and aqueous garlic extracts such that *Allium* species formulations specifically designed to

TABLE 3

Half-life data* (all values given in hours) at various temperatures determined for thiosulfinates in aqueous ethanol solutions. Initial aqueous garlic stock extract prepared by Process 1. Then, stock aqueous extract (1600 ppm with respect to allicin concentration) diluted to provide solutions containing 25%, 50% and 75% ethanol - each solution with initial allicin concentration at 400 ppm. Where A-I refers to MeS(O)SAll and AllS(O)SMe (collectively referred to Analogue-I), A-2 is allicin (referred to as Analogue-2) and A-3 refers to AllS(O)SPn-(E,Z) with both geometric isomers being collectively referred to as Analogue-3.

| Liquid Medium | 40° C. | 35° C. | 30° C. | 25° C. | 20° C. |
|---|---|---|---|---|---|
| 75% EtOH | A-1 = 15.4 (1.3) | A-1 = 30.9 (1.0) | A-1 = 43.6 (1.0) | A-1 = 76.9 (3.8) | A-1 = 150 (2.7) |
|  | A-2 = 8.4 (0.3) | A-2 = 16.3 (0.2) | A-2 = 23.3 (0.5) | A-2 = 41.2 (1.8) | A-2 = 82.3 (2.7) |
|  | A-3 = 17.6 (1.0) | A-3 = 30.3 (0.8) | A-3 = 46.9 (1.5) | A-3 = 73.4 (3.3) | A-3 = 160.7 (5.1) |
| 50% EtOH | A-1 = 27.7 (0.5) | A-1 = 49.8 (1.1) | A-1 = 102.5 (4.8) | A-1 = 175.5 (6.8) | A-1 = 349.3 (12.1) |
|  | A-2 = 14.8 (0.9) | A-2 = 28.1 (0.8) | A-2 = 57.1 (2.2) | A-2 = 101.9 (5.0) | A-2 = 181.6 (8.1) |
|  | A-3 = 17.3 (0.6) | A-3 = 28.8 (0.2) | A-3 = 65.6 (3.4) | A-3 = 121.3 (5.9) | A-3 = 203 (8.6) |
| 25% EtOH | A-1 = 50.3 (1.6) | A-1 = 90.3 (1.9) | A-1 = 135.1 (6.7) | A-1 = 247.4 (5.9) | A-1 = 472.2 (18.4) |
|  | A-2 = 24.1 (0.2) | A-2 = 41.8 (0.4) | A-2 = 62.1 (1.7) | A-2 = 115.4 (7.4) | A-2 = 218.5 (9.6) |
|  | A-3 = 15.3 (1.2) | A-3 = 25 (1.3) | A-3 = 39.5 (1.2) | A-3 = 66.1 (3.4) | A-3 = 134 (8.1) |

N.B. Values given relate to all garlic extract solutions each with an initial Analogue-2 concentration at 400 ppm.
*Mean half-life values shown with standard deviation values given in parentheses, For each temperature, a set of three separate samples were prepared for each aqueous ethanol composition and separately analyzed. Standard deviation values calculated using (n − 1) degrees of freedom applied to each triplicate sample data set.

The data in Table 3 reveals that for each aqueous garlic extract solution made up to provide a 25%, 50% and 75% ethanol concentration, throughout the temperature range measured MeS(O)SAll and AllS(O)SMe have significantly longer half-lives than allicin.

With aqueous solutions containing 25% and 50% ethanol MeS(O)SAll and AllS(O)SMe also have significantly longer half-lives than that determined for AllS(O)SPn-(E,Z) throughout the temperature range measured. However, with an aqueous solution containing 75% ethanol the half-lives determined for MeS(O)SAll and AllS(O)SMe are similar to AllS(O)SPn-(E,Z) throughout the temperature range measured.

When the same quantitative HPLC procedure is used to determine the half-lives of the thiosulfinates in a stock solution diluted with water to prepare an initial concentration of allicin equivalent to 375 ppm—again the half-lives of MeS(O)SAll and AllS(O)SMe measured at 20° C. are significantly greater than the half-lives for either allicin or incorporate these thiosulfinates will thereby provide longer shelf-lives and longer periods of therapeutic activity after the formulation has been administered.

Figure 5:
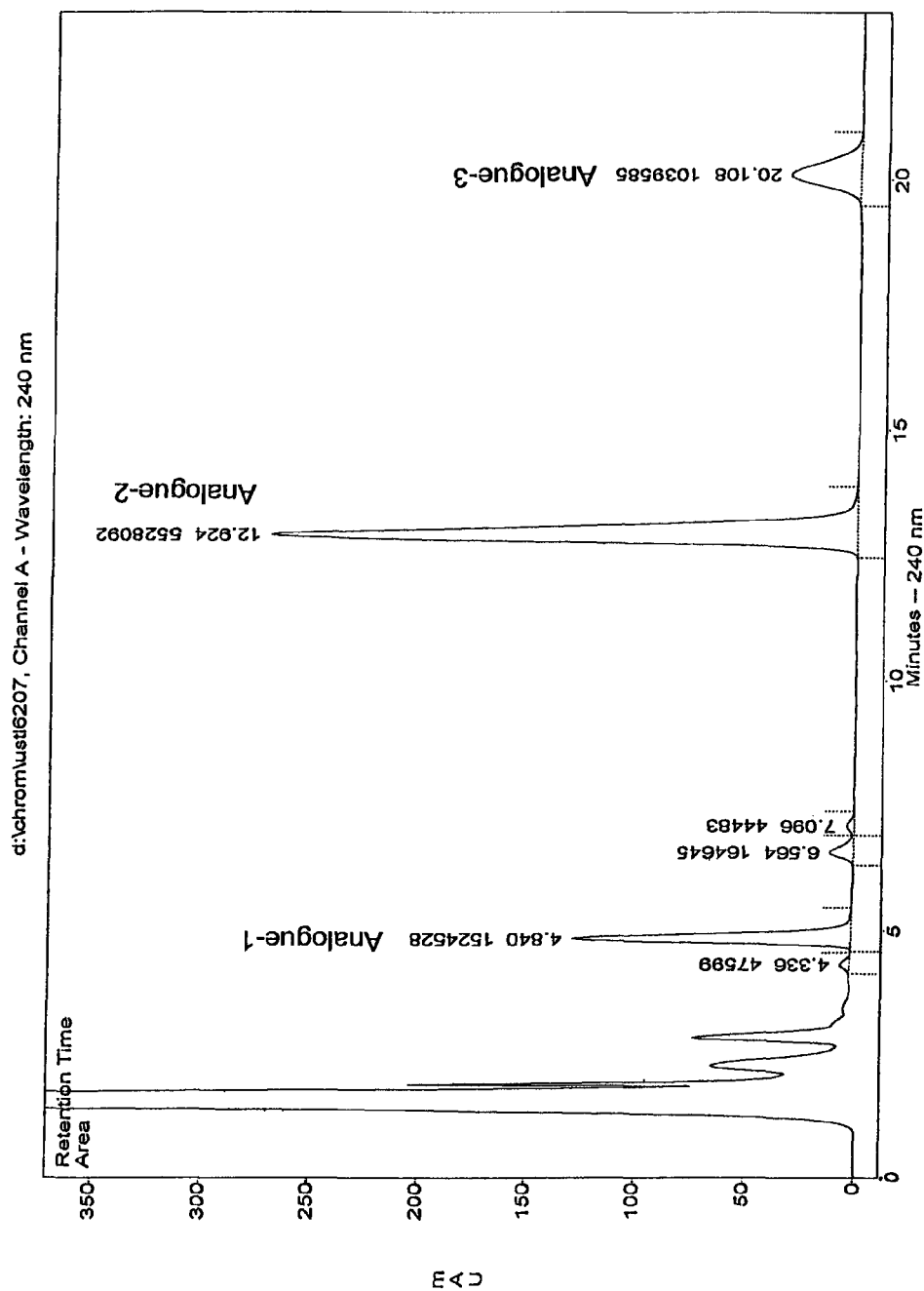
FIG. 5 is a reverse phase HPLC chromatogram obtained for aqueous garlic extract solution diluted to provide 25% percentage volume ethanol with initial allicin concentration of 400 ppm. Chromatogram obtained for freshly prepared solution Before being stored at 20° C.; reverse phase HPLC chromatogram obtained for an aqueous garlic extract solution diluted to provide 25% percentage volume ethanol providing an initial allicin concentration of 400 ppm. Chromatogram obtained for a freshly prepared extract before being stored at 20° C. Analogue-1 is MeS(O)SAll and AllS(O)SMe; Analogue-2 is allicin and Analogue-3 is AllS(O)SPn-(E,Z).
Figure 6:
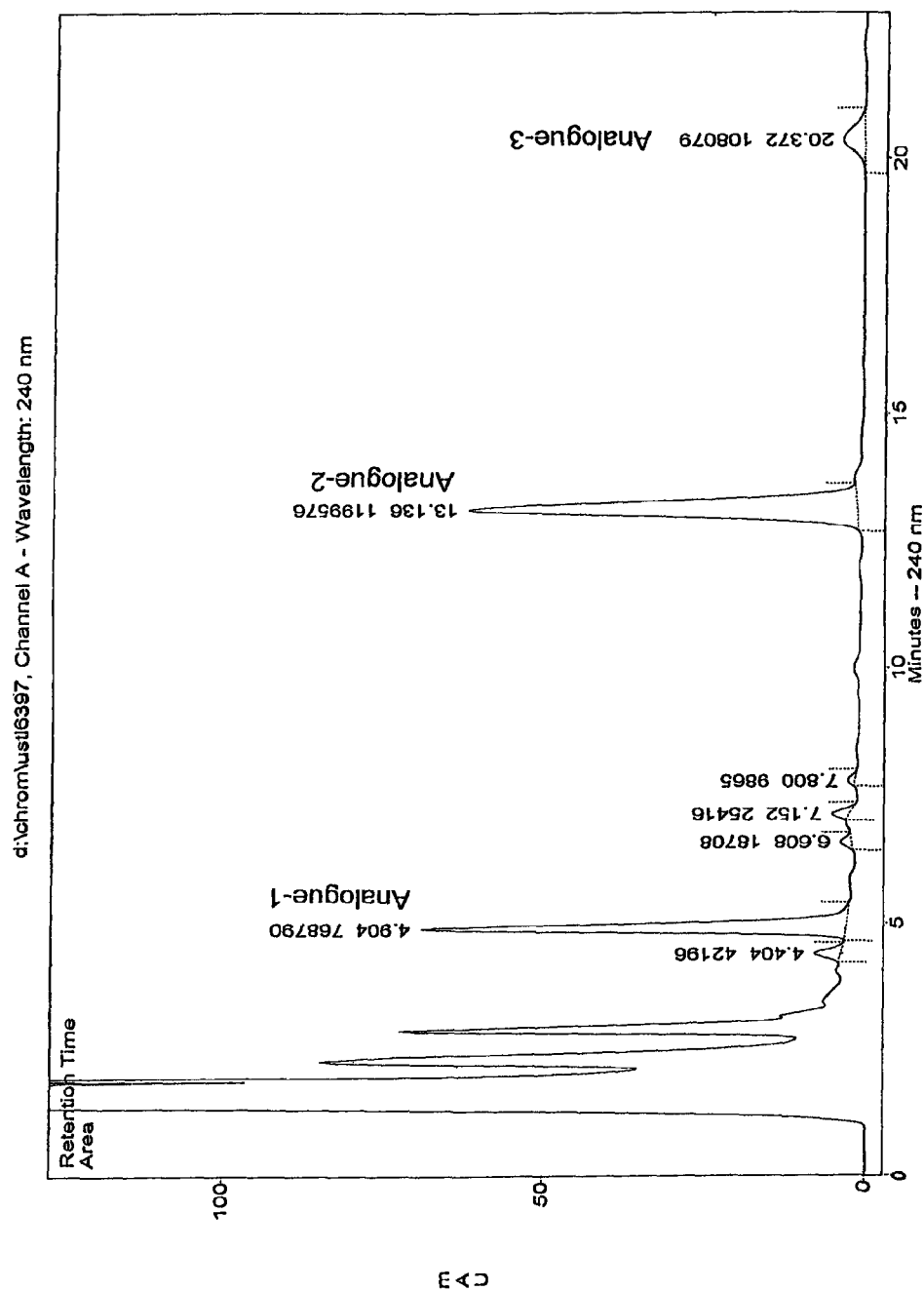
FIG. 6 is a reverse phase HPLC profile of same solution shown in FIG. 5 BUT after being stored at 20° C. for 452.75 hours.

Formulations containing both allicin and significant relative quantities of MeS(O)SAll and AllS(O)SMe therefore offer significant advantages compared to those formulations predominantly containing only allicin as the principle bioactive thiosulfinate. Both MeS(O)SAll and AllS(O)SMe support and compliment the bioactivity of allicin. As allicin concentrations start to diminish due to thermal degradation, the relative contribution of MeS(O)SAll and AllS(O)SMe to provide and support extended therapeutic biological activity progressively becomes more important. This is illustrated by comparison of the chromatograms shown in FIG. 5 and FIG. 6 that show the results of HPLC analyses obtained for the same aqueous garlic extract solution that had been diluted to initially provide 400 ppm allicin in a 25% ethanol preparation. As shown in FIG. 5 allicin initially provides a peak of higher amplitude (peak maxima measured on the mAU scale) compared with the peak obtained for the MeS(O)SAll and AllS(O)SMe thiosulfinate products. However, as shown in FIG. 6 after 452.75 hours storage at 20° C., due to its more rapid rate of decay the allicin peak is of lower amplitude than the peak obtained for the more stable MeS(O)SAll and AllS(O)SMe thiosulfinate isomers. This result indicates that allicin formulations supported by the incorporation of the MeS(O)SAll and AllS(O)SMe thiosulfinates would be more suitable for applications that require the therapeutic actions of thiosulfinates to be maintained for longer periods.

Aqueous garlic extracts produced according to Process 1 typically provide allicin concentrations in the range 750-1650 ppm. However, the relative concentration of MeS(O)SAll and AllS(O)SMe independently varies and is not directly related to initially manufactured allicin concentration. A typical range measured by comparing the integrated reverse phase HPLC peak area for MeS(O)SAll and AllS(O)SMe compared to the peak area obtained for allicin indicates that Process 1 provides an aqueous solution of garlic extract whose relative concentration of MeS(O)SAll and AllS(O)SMe is typically such that the reverse phase HPLC peak area integration value obtained (chromatogram at 240 nm) for the MeS(O)SAll and AllS(O)SMe thiosulfinates (Analogue-1) is 20-40% of the relative peak area obtained for allicin (Analogue-2) in a freshly manufactured, non-aged aqueous garlic extract.

In contrast to the procedure disclosed in Process 1—the Block et al report referred to previously provides data that establishes that some *Allium* species including garlic obtained from different geographical locations produce very low relative yields of MeS(O)SAll and AllS(O)SMe compared to allicin yield.

Process 1 described above provides a "semi-natural" process by which the MeS(O)SAll and AllS(O)SMe thiosulfinate content is enhanced. The natural processes whereby MeS(O)SAll and AllS(O)SMe are produced using damaged garlic tissue as the primary source of the essential precursor S-methyl-L-cysteine sulfoxide (methiin) are provided in Schemes 2-3. The processes given in Scheme 2 show the possibility of two condensation reactions between methyl-sulfenic acid and allyl-sulfenic acid to produce MeS(O)SAll and AllS(O)SMe.

Scheme 2. Showing the condensation reation between molecules of allyl-sulfenic acid and methyl-sulfenic acid to produce the asymmetric thiosulfinates MeS(O)SAll and AllS(O)SMe. Allyl-sulfenic acid is rapidly produced by the action of allinase on alliin whereas methyl-sulfenic acid is more slowly produced by the action of allinase on methiin. The allyl-sulfenic acid shown in the above reaction is provided by on-going reation between alliin and allinase.

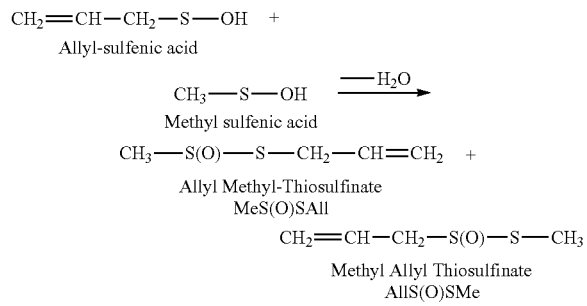

Scheme 3. Examples of the reactions of allyl-sulfenic acid and methyl-sulfenic acid that also bring about the formation of the MeS(O)SAll and AllS(O)SMe thiosulfinates.

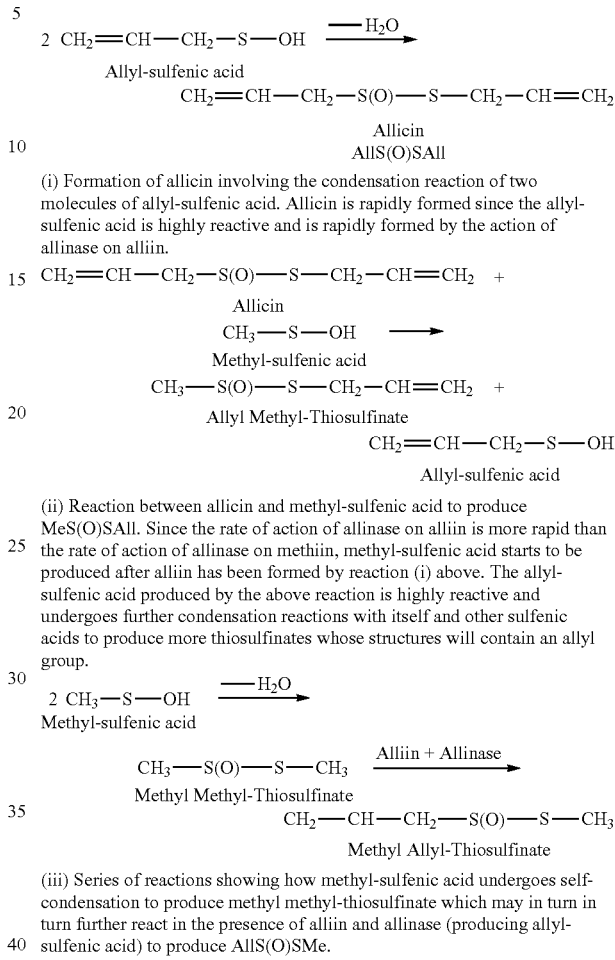

(i) Formation of allicin involving the condensation reaction of two molecules of allyl-sulfenic acid. Allicin is rapidly formed since the allyl-sulfenic acid is highly reactive and is rapidly formed by the action of allinase on alliin.

(ii) Reaction between allicin and methyl-sulfenic acid to produce MeS(O)SAll. Since the rate of action of allinase on alliin is more rapid than the rate of action of allinase on methiin, methyl-sulfenic acid starts to be produced after alliin has been formed by reaction (i) above. The allyl-sulfenic acid produced by the above reaction is highly reactive and undergoes further condensation reactions with itself and other sulfenic acids to produce more thiosulfinates whose structures will contain an allyl group.

(iii) Series of reactions showing how methyl-sulfenic acid undergoes self-condensation to produce methyl methyl-thiosulfinate which may in turn in turn further react in the presence of alliin and allinase (producing allyl-sulfenic acid) to produce AllS(O)SMe.

However, the natural chemical processes leading to MeS(O)SAll and AllS(O)SMe formation are more complex than Scheme 2 depicts.

S-allyl-L-cysteine sulfoxide (alliin) is a SACS species that undergoes rapid hydrolysis by the action of allinase—hence, allyl-sulfenic acid ($CH_2$=CH—$CH_2$—SOH) is rapidly formed when *Allium* species tissue is damaged. Allyl-sulfenic acid is highly reactive and once formed can rapidly undergo self-condensation such that two molecules of allyl-sulfenic acid bring about the formation of one molecule of allicin as represented in Scheme 3.

In comparison, S-methyl-L-cysteine sulfoxide (methiin) is a SACS species that undergoes relatively slow hydrolysis by the action of allinase. As a consequence of the relative rates of SACSs hydrolyses mediated by the action of allinase, during the time period required to bring about the formation of methyl-sulfenic acid ($CH_3$—SOH), the thiosulfinate allicin has already been produced. This fact provides the basis for the complex manner in which other reactions bring about the formation of the MeS(O)SAll and AllS(O)SMe thiosulfinates. As illustrated in Scheme 3, methyl-sulfenic acid can react with pre-formed allicin to produce AllS(O)SMe. This specific reaction liberates fresh allyl-sulfenic acid which will then very rapidly undergo further reactions—self-condensation producing allicin or reaction with other sulfenic acids to produce asymmetrical thiosulfinates e.g. reaction with methyl-sulfenic acid to produce further MeS(O)SAll and AllS(O)SMe as shown in Scheme 2. Alternatively, as is also shown in Scheme 3, methyl-sulfenic acid may undergo self-condensation to produce methyl methyl-thiosulfinate (MeS(O)SMe) that may then react with alliin in the presence of allinase to produce AllS(O)SMe.

Accordingly, in order to promote and control the amount of MeS(O)SAll and AllS(O)SMe manufactured in a formulation derived from *Allium* species independent of the age and geographical source of the *Allium* species, there is a need to regulate the processes that bring about the formation of thiosulfinates due to the action of allinase on the SACSs.

A study was then carried out to determine whether MeS(O)SAll and AllS(O)SMe yield could be boosted via the addition of methiin to a garlic tissue aqueous homogenate.

Figure 7:
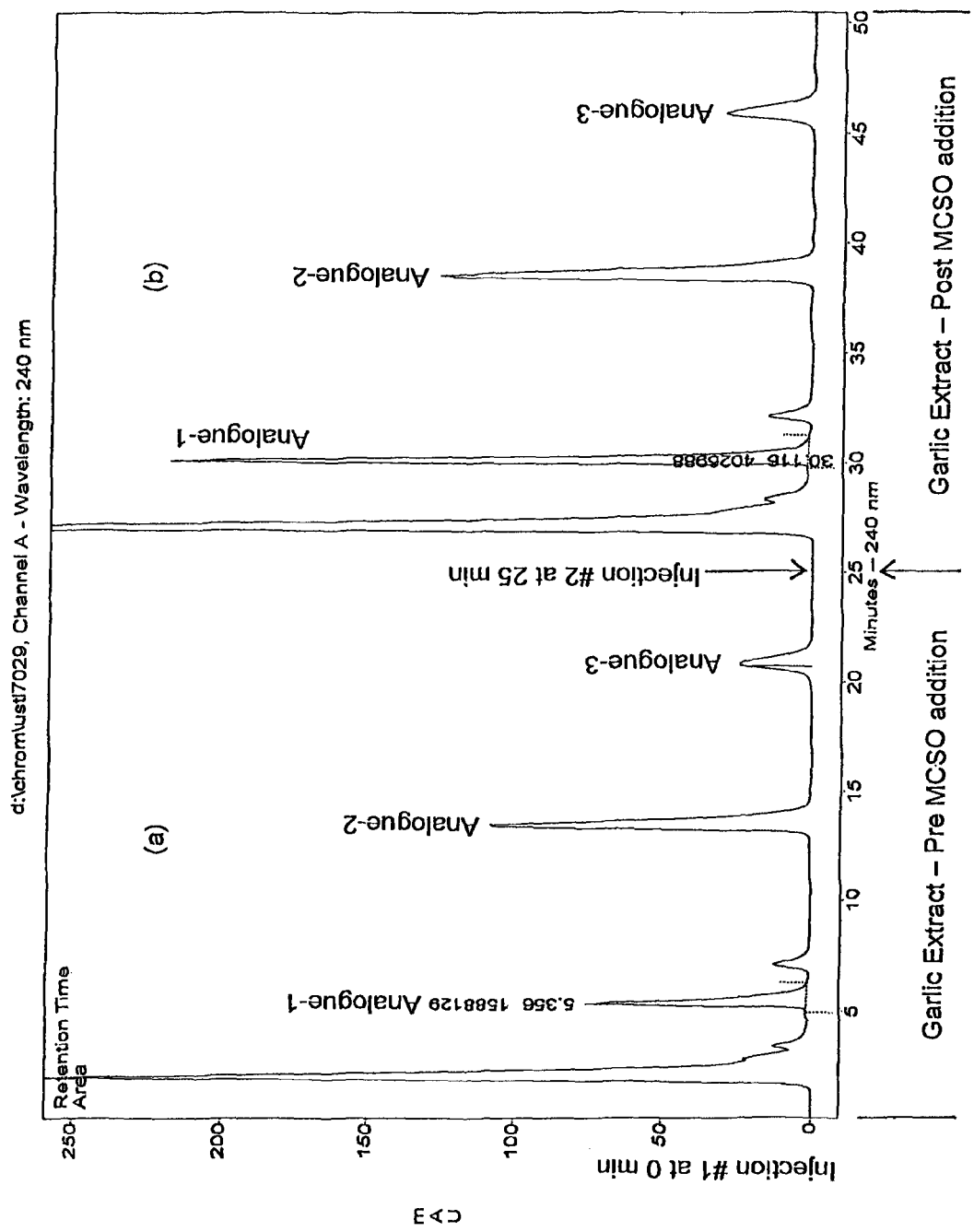
FIG. 7 is a feasibility study to demonstrate increased yield of Analogue-1 thiosulfinates via the addition of S-methyl-L-cysteine sulfoxide (MCSO) to aqueous garlic tissue homogenate solutions; (a) Pre-addition of MCSO and (b) Post-addition of MCSO.

The comparative reverse phase HPLC analyses shown in FIG. 7 clearly demonstrate that an increase in yield of MeS(O)SAll and AllS(O)SMe thiosulfinates can be obtained via the addition of synthetic methiin (sourced by Shanghai Boyle Chemical Company Ltd., Shanghai, China) to freshly homogenised garlic tissue blended in water. During the retention time interval 0-25 minutes the reverse phase HPLC profile obtained for a garlic extract made without the addition of methiin is shown, after which during retention interval 25-50 minutes the HPLC profile of an aqueous garlic extract to which methiin had been added is shown. Clearly the addition of methiin has boosted (allicin peak amplitude approximately the same value for both extracts) the concentration of MeS(O)SAll and AllS(O)SMe relative to the allicin concentration.

Accordingly, it was clear that the that the collective MeS(O)SAll and AllS(O)SMe concentration can indeed be boosted in the inventive method by addition of synthetic methiin to a fresh *Allium* species extract, in particular that made from a chopped/minced/ground/crushed garlic water slurry. This forms a further aspect to the present invention. The methiin can be provided by synthetic sources as used in our trial or from other sources, such as a powdered *Allium* species (for example, powdered garlic).

Figure 8:
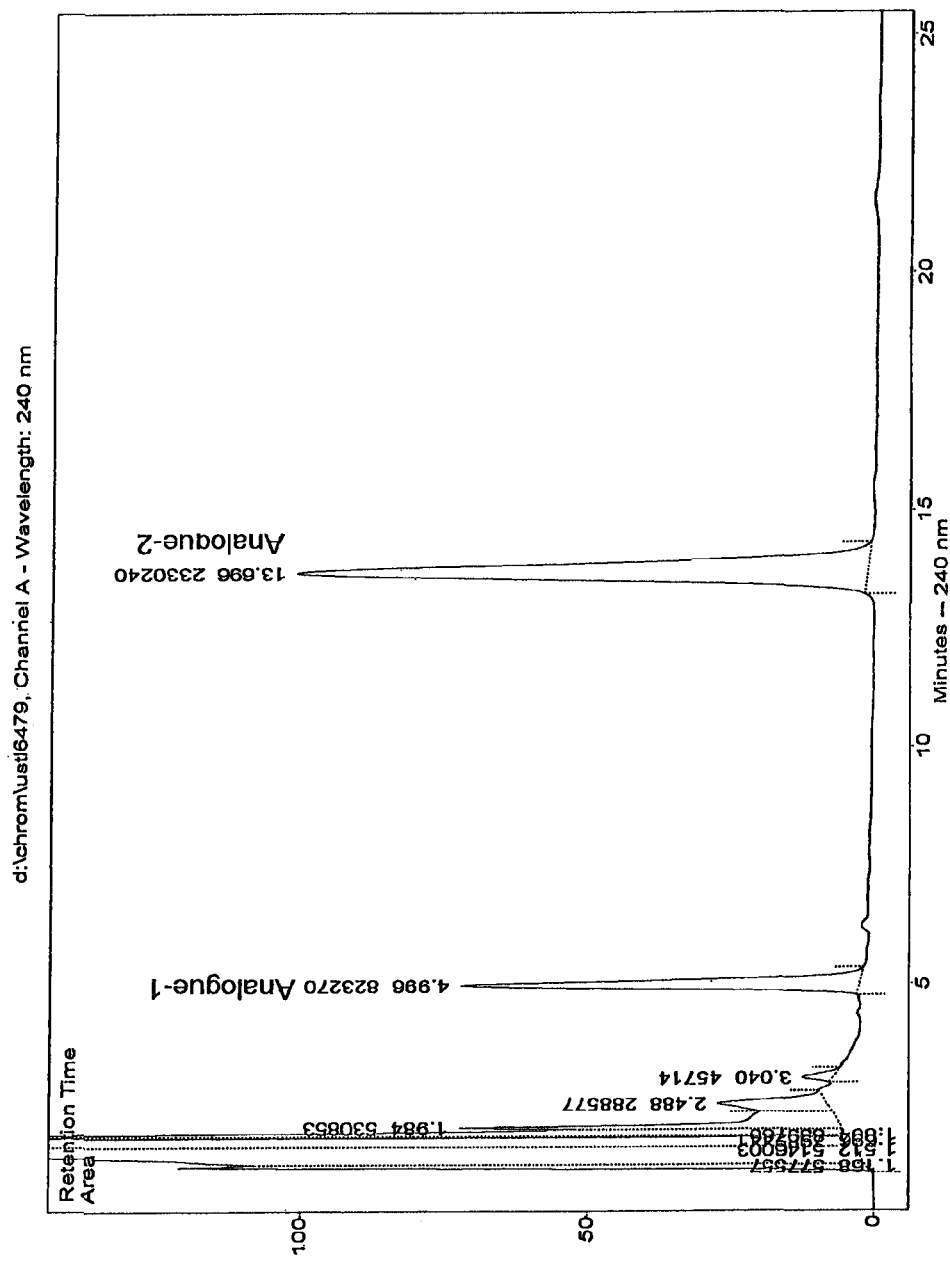
FIG. 8 is a reverse phase HPLC chromatogram of a garlic powder in water; reverse phase HPLC profile obtained for a solution prepared by treating garlic powder with water. Where the peak labeled as Analogue-1 is composed of MeS(O)SAll and AllS(O)SMe and peak labeled as Analogue-2 is allicin.
Figure 9:
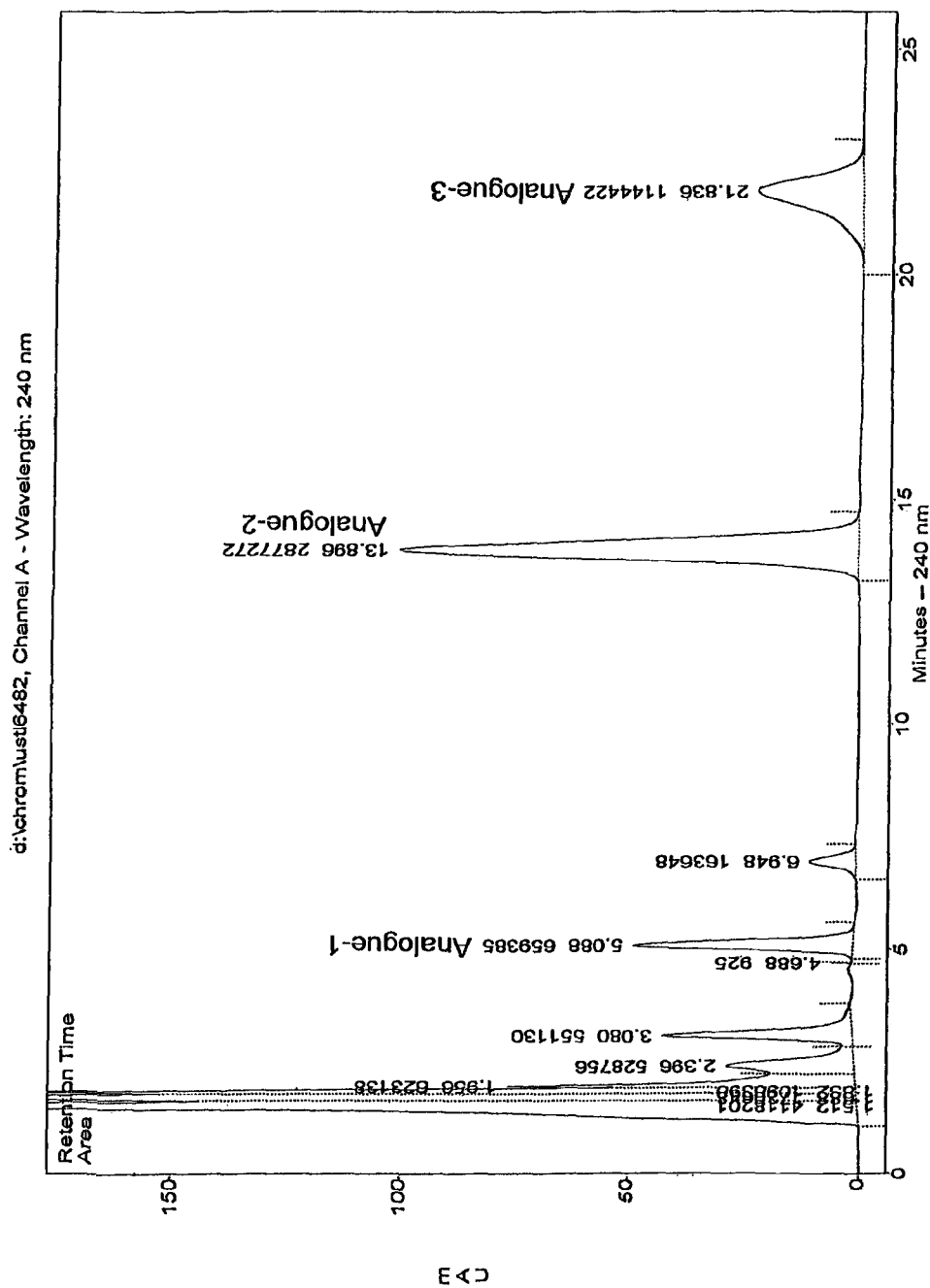
FIG. 9 is a reverse phase HPLC chromatogram of a freshly prepared garlic extract; reverse phase HPLC profile obtained for a garlic extract prepared from only garlic and water according to Process 1. Where peak labeled as Analogue-1 is derived from the unresolved MeS(O)SAll and AllS(O)SMe thiosulfinates; Analogue-2 is allicin and Analogue-3 is AllS(O)SPn-(E,Z).
Figure 10:
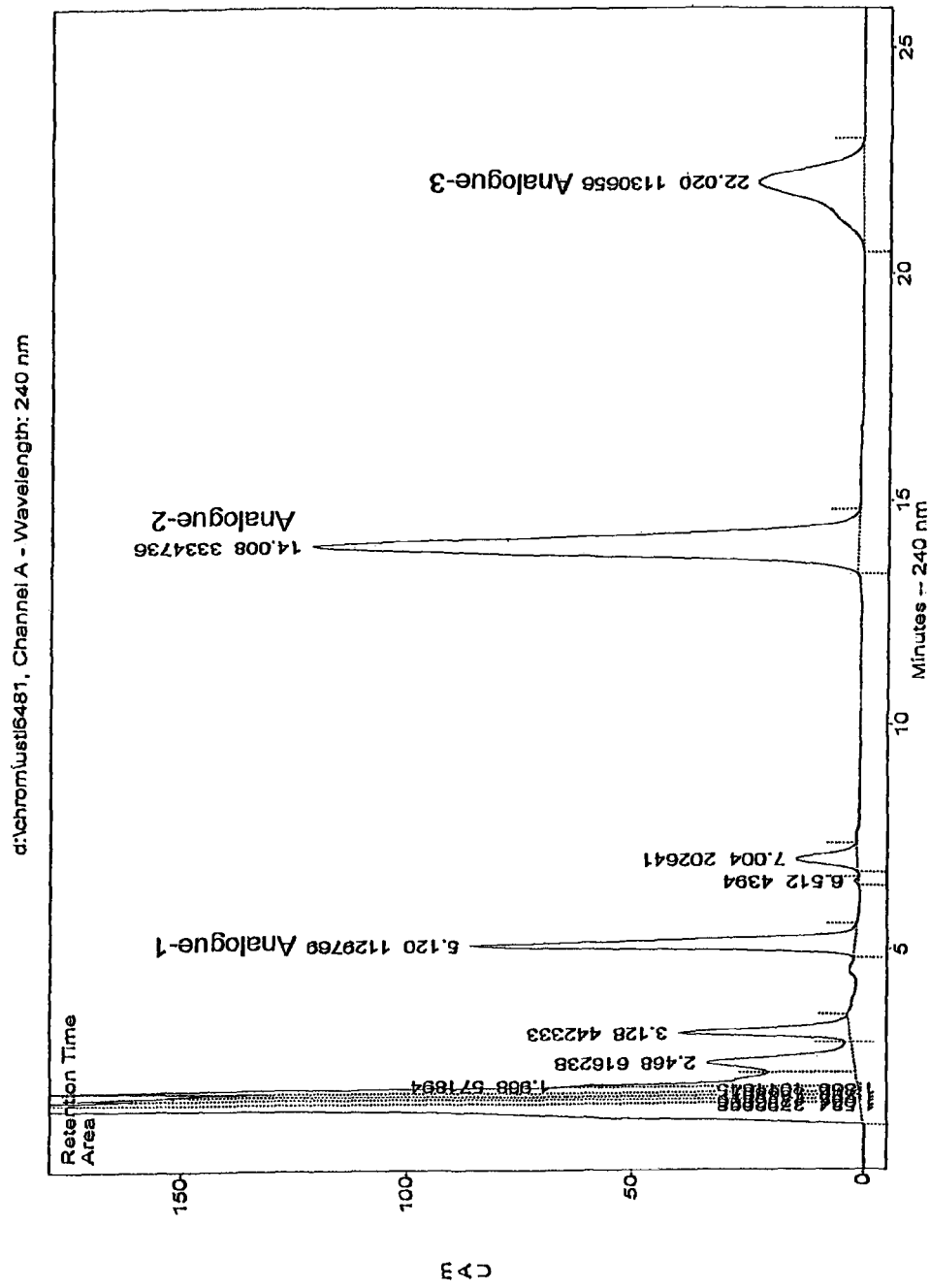
FIG. 10 is a reverse phase HPLC chromatogram of a freshly prepared garlic extract to which garlic powder has been added; reverse phase HPLC profile obtained for a garlic extract prepared from garlic and water according to Process 1 BUT including the addition of garlic powder. Where peak labeled as Analogue-1 is derived from the unresolved MeS(O)SAll and AllS(O)SMe thiosulfinates; Analogue-2 is allicin and Analogue-3 is AllS(O)SPn-(E,Z).

This is illustrated by a comparison of FIGS. 8 to 10. FIG. 8 shows a chromatogram (same conditions as above) of a commercial garlic powder mixed with water. A-1 is the chromatographic peak obtained for the co-eluting MeS(O)SAll and AllS(O)SMe analogues and A-2 is allicin (as above). It will be appreciated that hydrated garlic powder has not provided a source of AllS(O)SPn-(E,Z) (A-3). However, as the chromatogram in FIG. 8 establishes powdered garlic is a relatively rich source of both methiin and alliin providing sufficient allinase activity on being contacted with water to bring about the production of MeS(O)SAll and AllS(O)SMe and allicin.

FIG. 9 is a chromatogram of a fresh extract of garlic and FIG. 10 is a chromatogram of a garlic extract prepared as for FIG. 9 but with the addition of the garlic powder chromatographed in FIG. 8. FIG. 9 is a chromatogram obtained from a garlic extract prepared according to Process 1—using an initial mix of 625 g chopped garlic+1 liter of water only.

FIG. 10 is a chromatogram obtained from a garlic extract prepared according to Process 1—using an initial mix of 625 g chopped garlic+1 liter of water+25 g garlic powder. The 25 g garlic powder going into the initial mix is of the same type as that used to provide an extract whose chromatogram is shown in FIG. 8.

Comparing the integration values shown in FIGS. 9 and 10 for the collective MeS(O)SAll and AllS(O)SMe chromatographic peak there is an enhancement of the MeS(O)SAll and AllS(O)SMe concentration in the garlic extract prepared with garlic powder addition. Also, comparison of the allicin peak integration values in FIGS. 9 and 10 reveals that the allicin concentration has also been increased by the addition of garlic powder. The concentration of produced AllS(O)SPn-(E,Z) is virtually unaffected by the addition of garlic powder and its peak integration value is therefore almost the same in FIGS. 9 and 10. In FIG. 9 the collective MeS(O)SAll and AllS(O)SMe integrated peak area compared to the allicin integrated peak area is 22.9% whereas this ratio increases to 33.9% in FIG. 10. This result confirms that the addition of garlic powder constitutes an inventive step to preferentially boost the production of the MA-AM analogues relative to allicin whose concentration is also promoted via the addition of garlic powder to fresh garlic using Process 1.

Bioassay Study

A bioassay study was conducted to compare the liquid produced according to Process 1 with commercially available allicin containing liquid, i.e. Allisure® Liquid provided by Allicin International Limited (AIL), Half House, Military Road, Rye East Sussex TN31 7NY, United Kingdom.

A. AIL supplied liquid with relatively low A-1 concentration, relatively low A-2 and low A-3 concentration.

B. Liquid prepared from fresh garlic according to process 1—with high A-1 concentration, low A-3 concentration.

Details of Liquid Compositions

| Sample Origin | A-1 | A-2 | A-3 | Total |
|---|---|---|---|---|
| A - Allisure ® Liquid | 58 ppm | 570 ppm | 9 ppm | 637 ppm |
| B - Fresh Garlic Extract | 259 ppm | 561 ppm | 4 ppm | 824 ppm |

Figure 11:
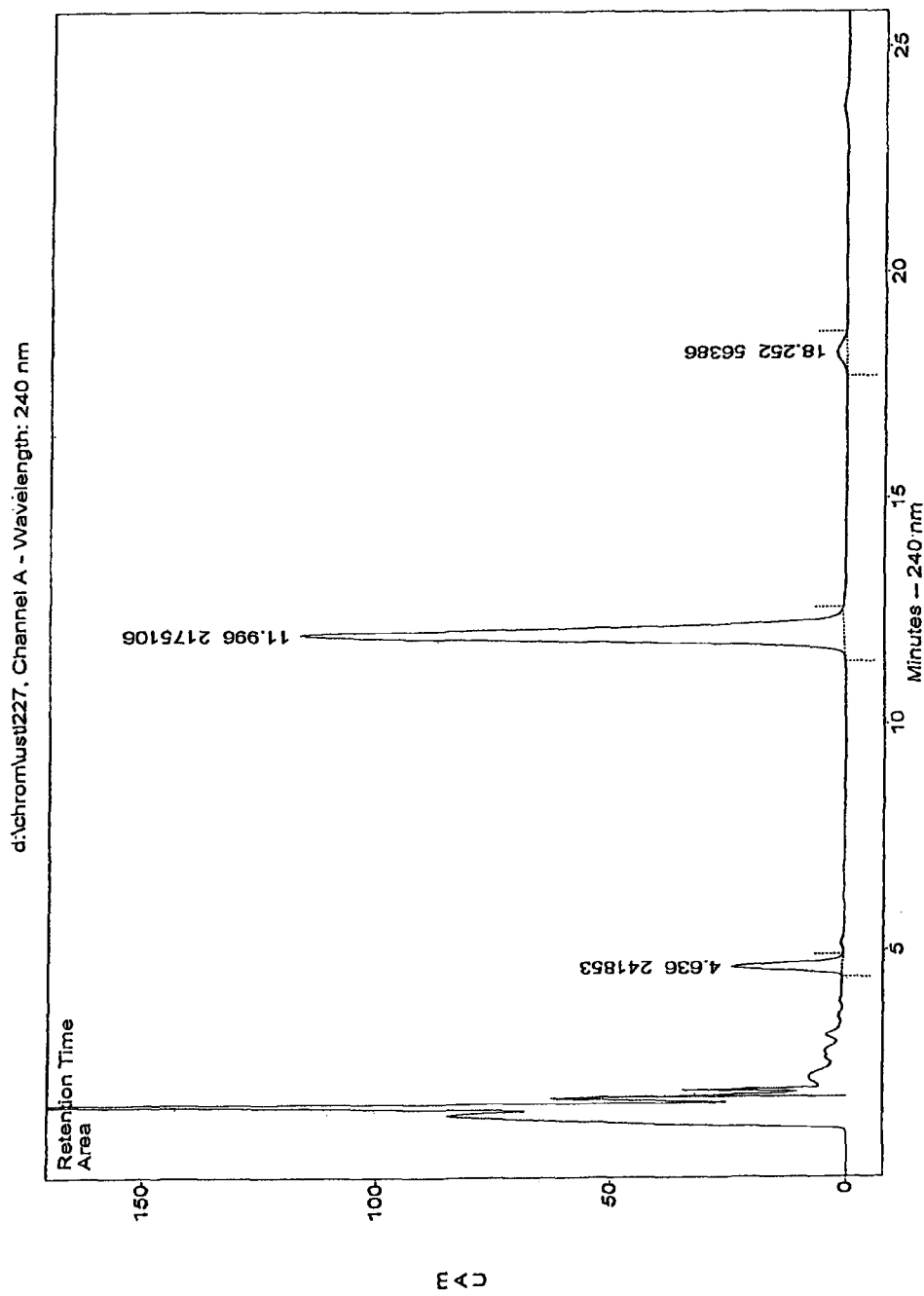
FIG. 11 is a reverse phase HPLC chromatogram of a commercially available garlic liquid.
Figure 12:
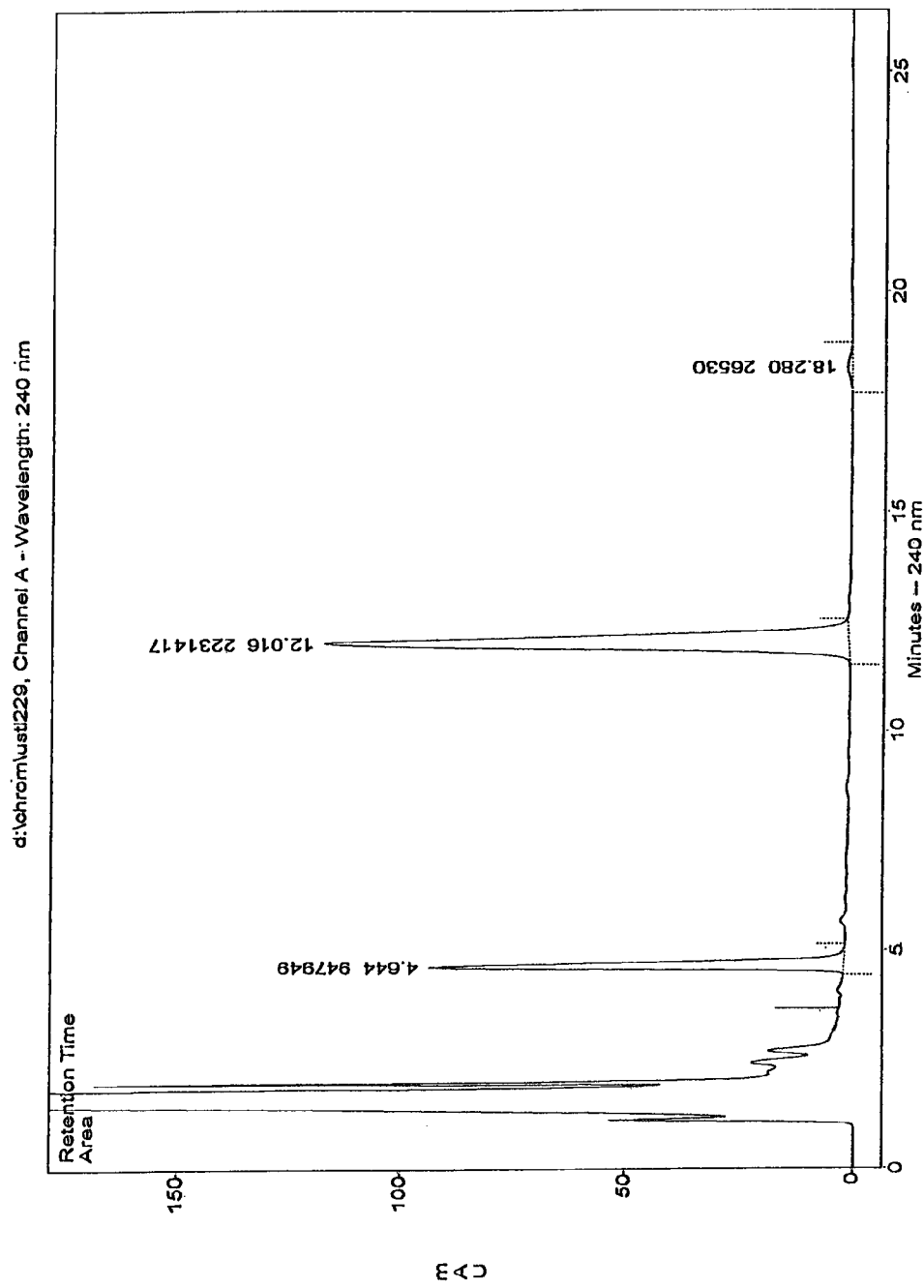
FIG. 12 is a reverse phase HPLC chromatogram of another freshly prepared garlic extract.

FIG. 11 shows the HPLC analysis of a comparative example of commercially available liquid, where A-1, A-2 and A-3 retention times are 4.636, 11.996 and 18.252 min respectively. Peak integration values for thiosulfinate analogue peaks are also shown. FIG. 12 shows the HPLC analysis of extract prepared from Fresh Garlic, according to process 1, where A-1, A-2 and A-3 retention times are 4.644, 12.016 and 18.28 min respectively. Peak integration values for thiosulfinate analogue peaks are also shown.

Theoretical Bioassay Performance

Assuming that the two thiosulfinate analogues provide approximately equivalent bioactivity then Fresh Garlic extract should provide a bioassay 824/637=approx. +29% higher than AIL liquid.

Bioassay Method

1. Sterile agar plate prepared with a broth containing a strain of *E. Coli*.
2. Plates air dried.
3. Plate divided into 3 sectors.
3. A 7.5 mm well cut into each of the 3 sectors of the plate.
4. 50 μl of liquid then added to two wells.
5. Plate incubated at 25° C. overnight.
6. Zones (diameters) of inhibition measured.

Bioassay Results

A 24 mm zone of bioactivity was obtained around the well of "AIL liquid". For the Fresh Garlic extract manufactured according to process 1, a 26 mm zone was obtained. To determine the performance, the following formula was used:

Area of bioactivity=Total area of Zone−Area of Well

Accordingly the area of bioactivity for the commercially available liquid=$[3.1416 \times (12)^2]-[3.1416 \times (3.75)^2]$=408 mm². The area of bioactivity for the liquid made in accordance with process 1=[3.1416×(13)²]−[3.1416×(3.75)²]=486 mm²

Accordingly, for extract prepared from fresh garlic extract, the relative performance improvement compared to commercially available AIL liquid is 486/408=+19%.

Conclusions:

Bioassay results confirm that for an aqueous allicin containing liquid—initial bioassay performance (liquids not aged) is improved if A-1 concentration is increased.

The liquids tested both had very low A-3 concentrations i.e. performance enhancement is due to increased A-1 concentration.

The experimentally determined +19% for the extracts prepared from fresh garlic and powdered garlic is below the theoretical +28-29%. Nevertheless, the enhancement (approx. 66% of that theoretically predicted) is commercially significant and confirms that A-1 (i.e. methyl allyl-thiosulfinate and/or allyl methyl-thiosulfinate) is effective.

The difference between theoretical and experimental bioassay results may be due to the accuracy in measuring zones of bioactivity in this instance a tolerance of ±0.5 mm is highly significant and the fact that the wells were not perfectly cut to provide accurate circles resulted in the zones not providing perfect circles—made it more difficult to accurately measure zones (diameters) of biological activity.

If the zone of activity for fresh garlic extract had been measured at 26.5 mm then the calculated improvement in biological activity would be +24% (i.e. approx. 83% of that theoretically predicted).

Process 3

A solution was prepared by dissolving 1.3 g alliin (7.3446 mmol) and 1.1 g methiin (7.2847 mmol) with mixing in 100 ml water at a temperature maintained at 10-40° C. The mixed alliin and methiin solution was then contacted with allinase (e.g. 0.2-2 g freshly minced garlic) and the solution stirred for 10 minutes. The solution was assayed periodically using HPLC to calculate the concentration of methyl allyl thiosulfinate and allyl methyl thiosulfinate. Once HPLC assay results indicated no further production of methyl allyl thiosulfinate and allyl methyl thiosulfinate, 900 ml of water at a temperature of 4° C. was added, to provide a methyl allyl thiosulfinate and allyl methyl thiosulfinate solution of approximately 1000 ppm concentration (based on the combined amounts of methyl allyl thiosulfinate and allyl methyl thiosulfinate). The resultant solution was filtered and stored at −20° C. until required.

Process 3 is highly adaptable. The concentration of methiin and alliin can be adjusted by varying the amount of water. The alliin can be added progressively to a solution of the methiin to allow time for methiin to form the methyl-sulfenic acid so that it is immediately available once alliin very rapidly is converted into allyl-sulfenic acid.

In a modification of this process, increasing an amount of alliin relative to a fixed mass of methiin above a 1:1 mole ratio, controlled quantity of allicin is formed in addition to the methyl allyl thiosulfinate and allyl methyl thiosulfinate formed.

Process 4

Further "almost fully synthetic" processes were also carried out, in which the source of alliin (herein also referred to as "Precursor-2") and methiin (herein also referred to as "Precursor-1") were synthetic and the source of allinase was garlic powder (GP).

Figure 13:
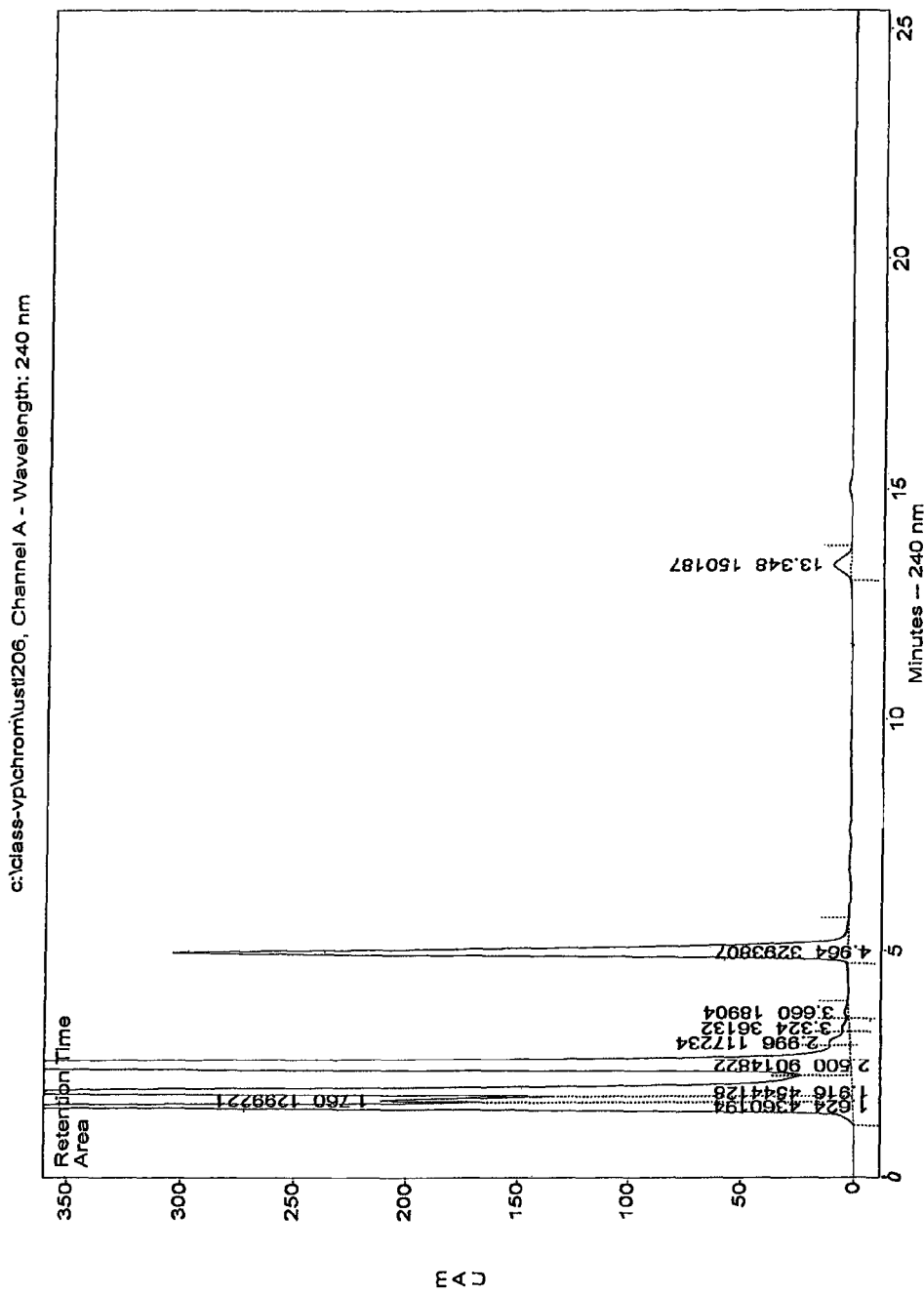
FIG. 13 is a reverse phase HPLC chromatogram obtained for a sample of liquid prepared in accordance with process 4(a)

In process 4(a) Garlic powder (3.0 g) was added to a solution of "Precursor-1" (200 mg of synthetic methiin dissolved in 35 ml water). After 60 min mixing at 21° C. a sample was withdrawn and analysed by HPLC. The result is shown in FIG. 13.

Figure 14:
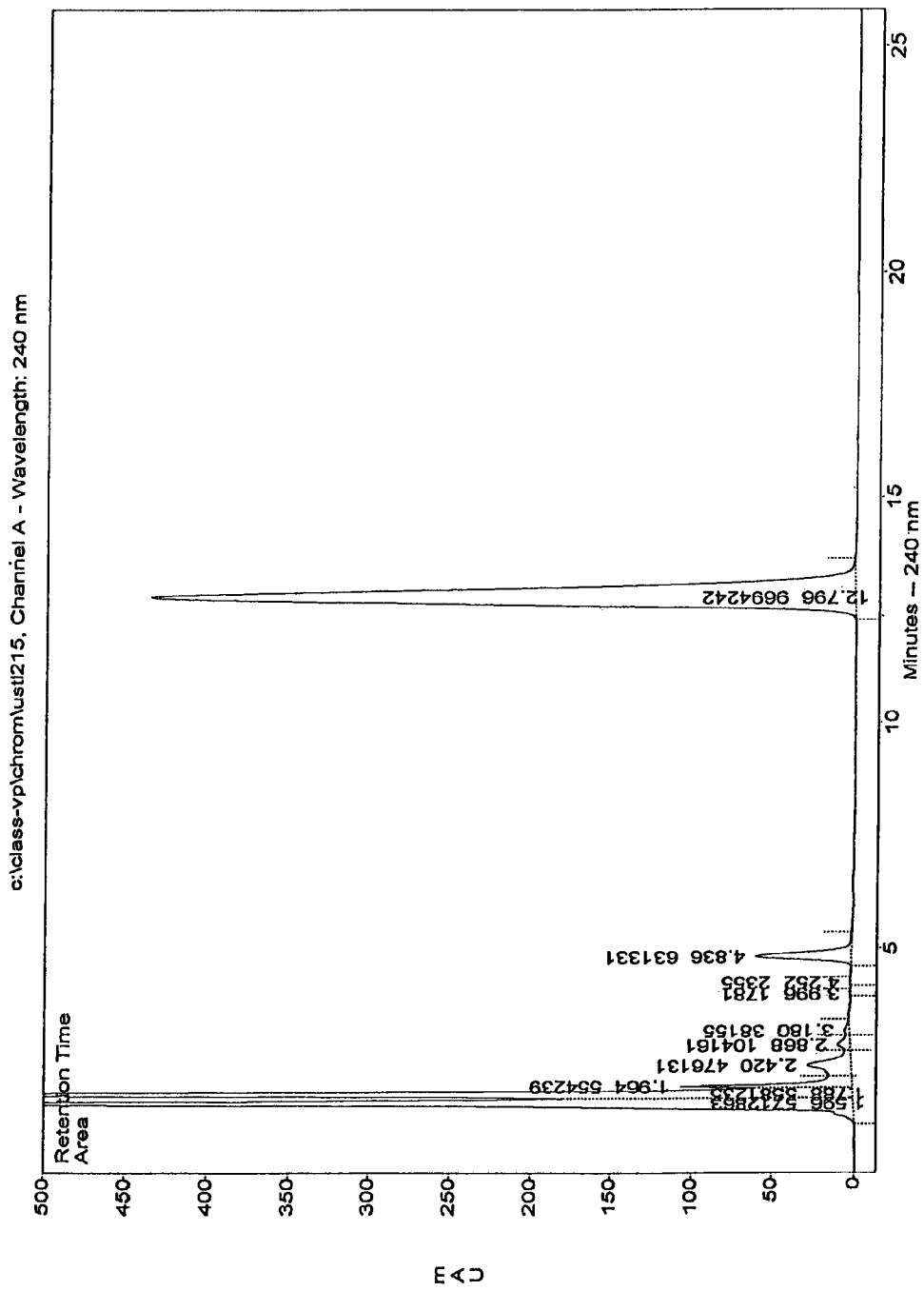
FIG. 14 is a reverse phase HPLC chromatogram obtained for a sample of liquid prepared in accordance with process 4(b)

In process 4(b) Garlic powder (3.0 g) was added to a solution of "Precursor-2" (200 mg of synthetic alliin dissolved in 35 ml water). After 60 min mixing at 21° C. a sample was withdrawn and analysed by HPLC. The result is shown in FIG. 14.

Figure 15:
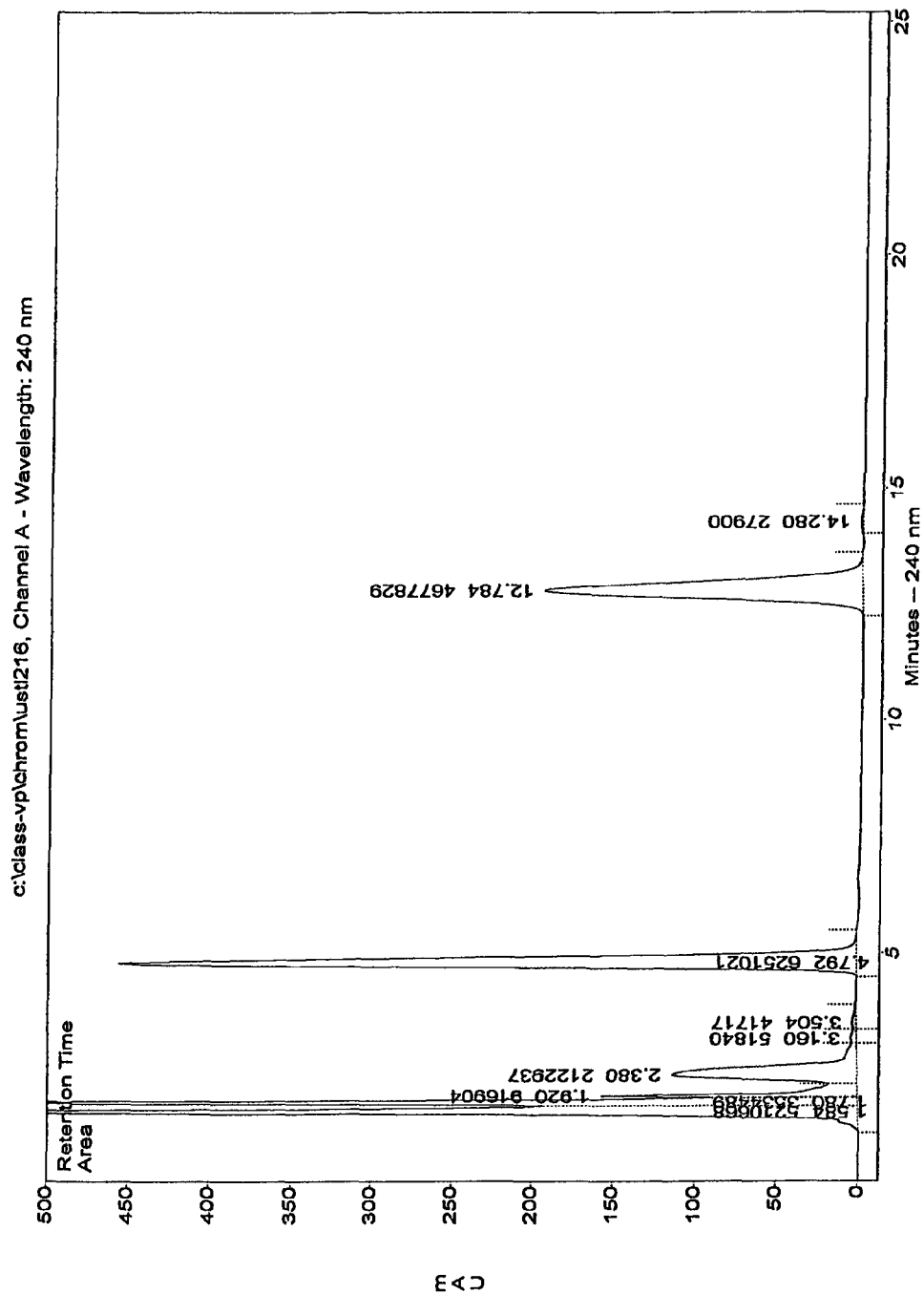
FIG. 15 is a reverse phase HPLC chromatogram obtained for a sample of liquid prepared in accordance with process 4(c)

In process 4(c) Garlic powder (3.0 g) was added to a solution of "Precursor-1" and "Precursor-2" (200 mg of each of synthetic methiin and synthetic alliin combined and dissolved in 35 ml water). After 60 min mixing at 21° C. a sample was withdrawn and analysed by HPLC. The result is shown in FIG. 15.

After 60 min mixing at 21° C. HPLC assays shown in FIGS. 13-15 show the following peaks:

| Solution | FIG. | Analogue-1 (MA-AM) | Analogue-2 (Allicin) |
|---|---|---|---|
| GP + Precursor-1 | 13 | 795 ppm | 39 ppm |
| GP + Precursor-2 | 14 | 152 | 2540 |
| GP + Precursor-1 + Precursor-2* | 15 | 1508 | 1225 |

It can be seen from the results that the concentration of Analogue-1 can be substantially boosted by contacting a solution of methiin and alliin with garlic powder. Examination of the chromatograms of FIGS. 13-15, reveals that solutions containing Precursor-1 when contacted with garlic powder produce a chromatographic peak at retention time of around 2.5 minutes. Some information concerning the possible identity of the peak whose retention time is about 2.5 mins, which is believed to be methyl methyl-thiosulfinate is set out below.

Figure 16:
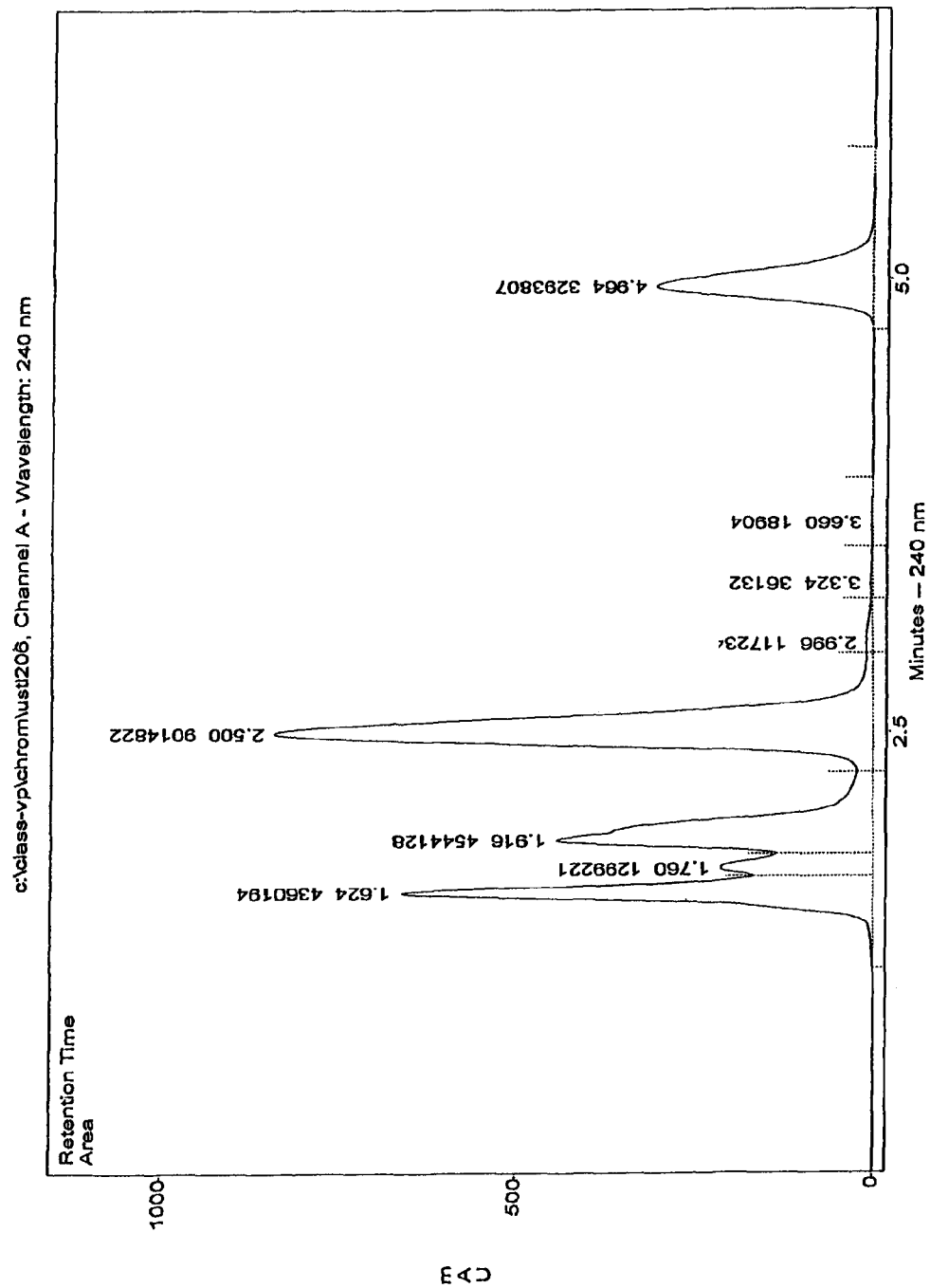
FIG. 16 shows an expanded section of the chromatogram of FIG. 13.
Figure 17:
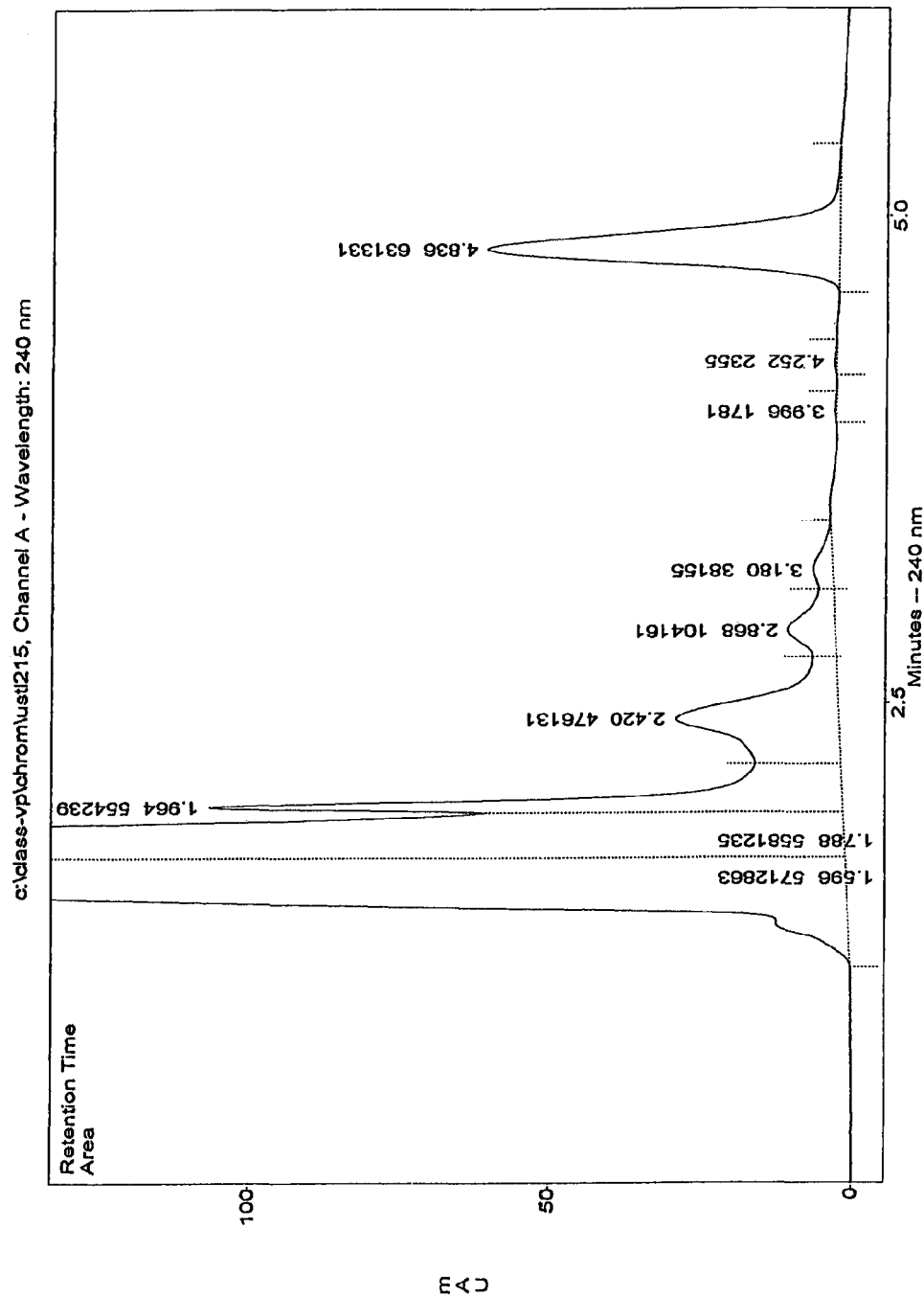
FIG. 17 shows an expanded section of the chromatogram of FIG. 14.
Figure 18:
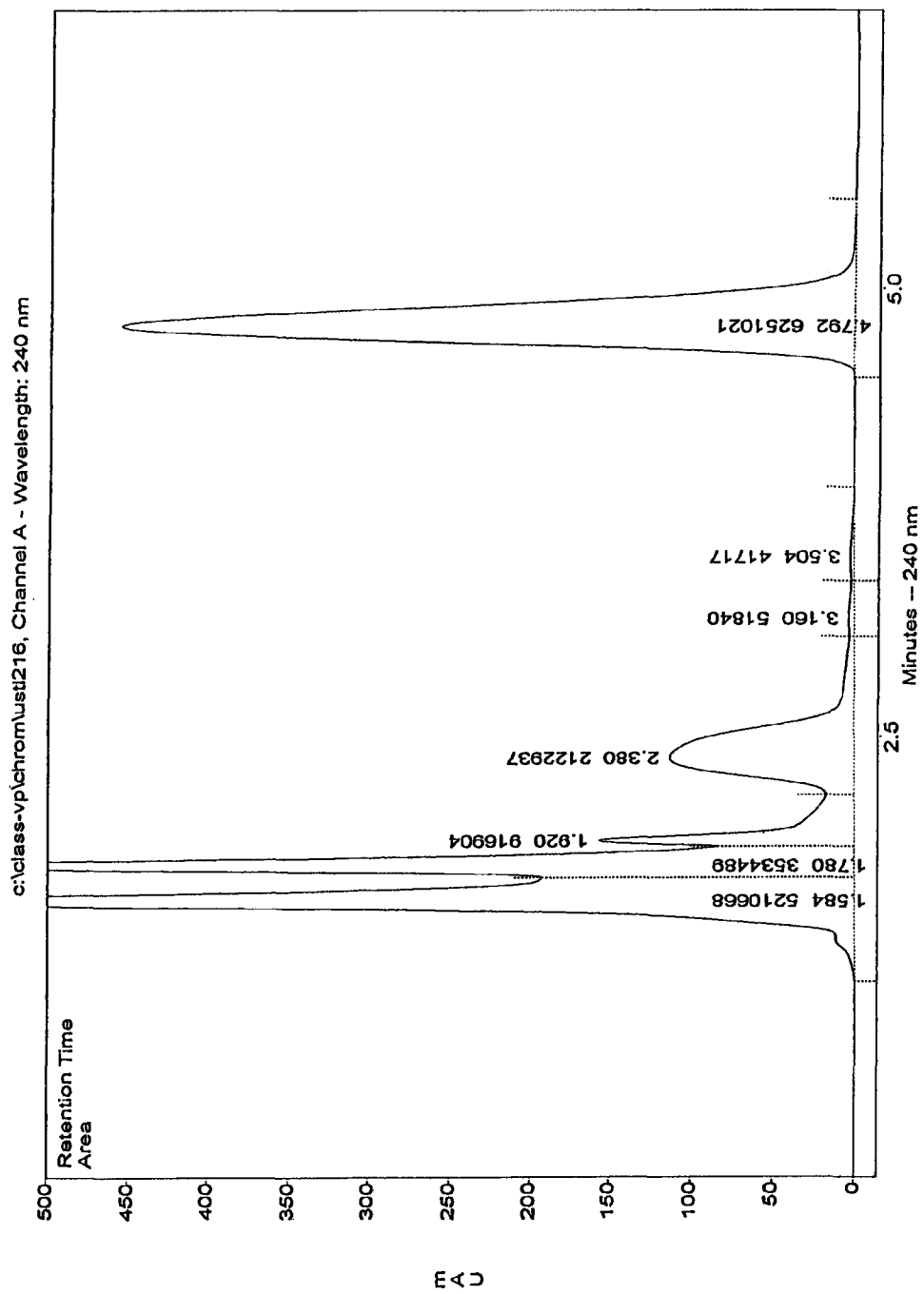
FIG. 18 shows an expanded section of the chromatogram of FIG. 15.

For comparative purposes early sections of FIGS. 13-15 are shown in FIGS. 16-18, respectively, with the mAU axis attenuation adjusted such that both the peak whose retention time at approx. 2.5 mins and Analogue-1 peak are on-scale.

Examination of FIGS. 16-18 reveals that the peak at about 2.5 minutes is most intense when only Precursor-1 is treated with GP and is virtually absent when only Precursor-2 is treated with GP.

Being aware of the relevant chemistry it is postulated that the peak whose retention time is approximately 2.5 mins is the methyl methyl-thiosulfinate.

In order to ascertain the compound causing the peak whose retention time is around 2.5 min LC-MS studies were performed.

Unfortunately the LC system could not be directly connected to the MS since the MS system could not directly handle the 1 ml/min flow rate. Therefore, a reduced flow rate was used with a gradient mobile phase of increasing methanol content.

The relative molecular weights of the species of interest are:

Methyl methyl-thiosulfinate: 110
Analogue-1 (MA-AM): 136
Analogue-2 (Allicin): 162

The ionization method was positive ion electrospray which means that for each of the above three species a protonated molecule ion [M+H]⁺ should be formed at m/z: 111, 137, and 163, respectively.

Due to the considerable changes in chromatography conditions retention data in the LC-MS studies will not correlate with those shown in FIGS. 13-18. However, relative peak position and intensity data will be considered.

Figure 19:
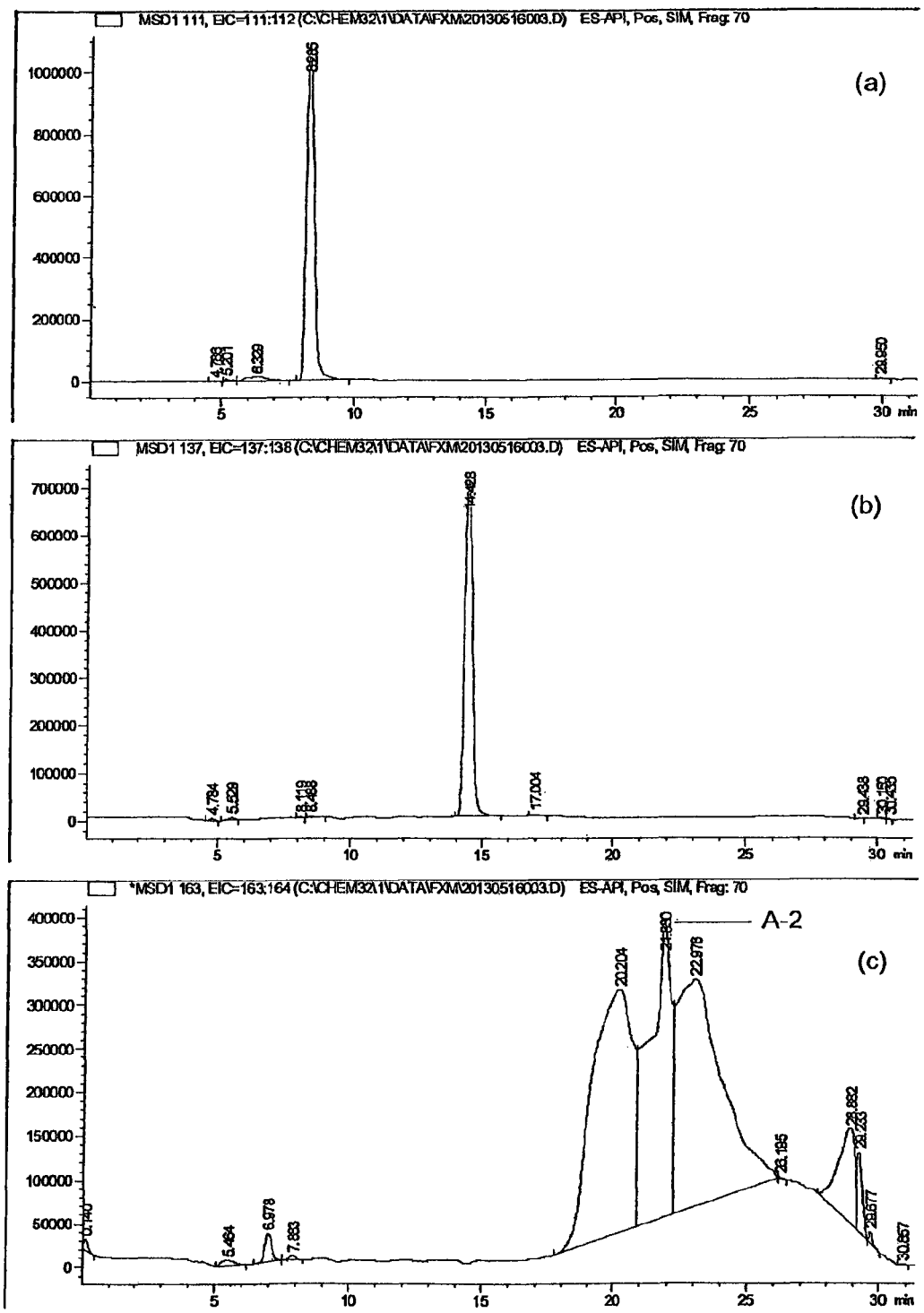
FIG. 19 (to be roughly compared to FIGS. 13 and 16) shows the LC-MS analysis for a solution prepared from GP+Precursor-1 (methiin)

FIG. 19: Sample: 3.0 g GP added to a solution of 200 mg Precursor-1 (methiin) in 35 ml water. Channels: (a) m/z 111 specific for detecting methyl methyl-thiosulfinate (b) for Analogue-1 and (c) for Analogue-2. Note: Rising baseline in channel (c)—possibly due to impurity in mobile phase. In FIG. 19 there are strong signals in the m/z channels: 111 and 137 with only a weak signal in the m/z channel 163. The peaks are in the correct relative retention time order. This result is consistent with high levels of formation of the methyl methyl-thiosulfinate and Analogue-1 (MA-AM) and a low level of Analogue-2 (allicin) that would be predicted taking into account the relevant thiosulfinate formation chemistry applicable for this specific reaction mixture.

Figure 20:
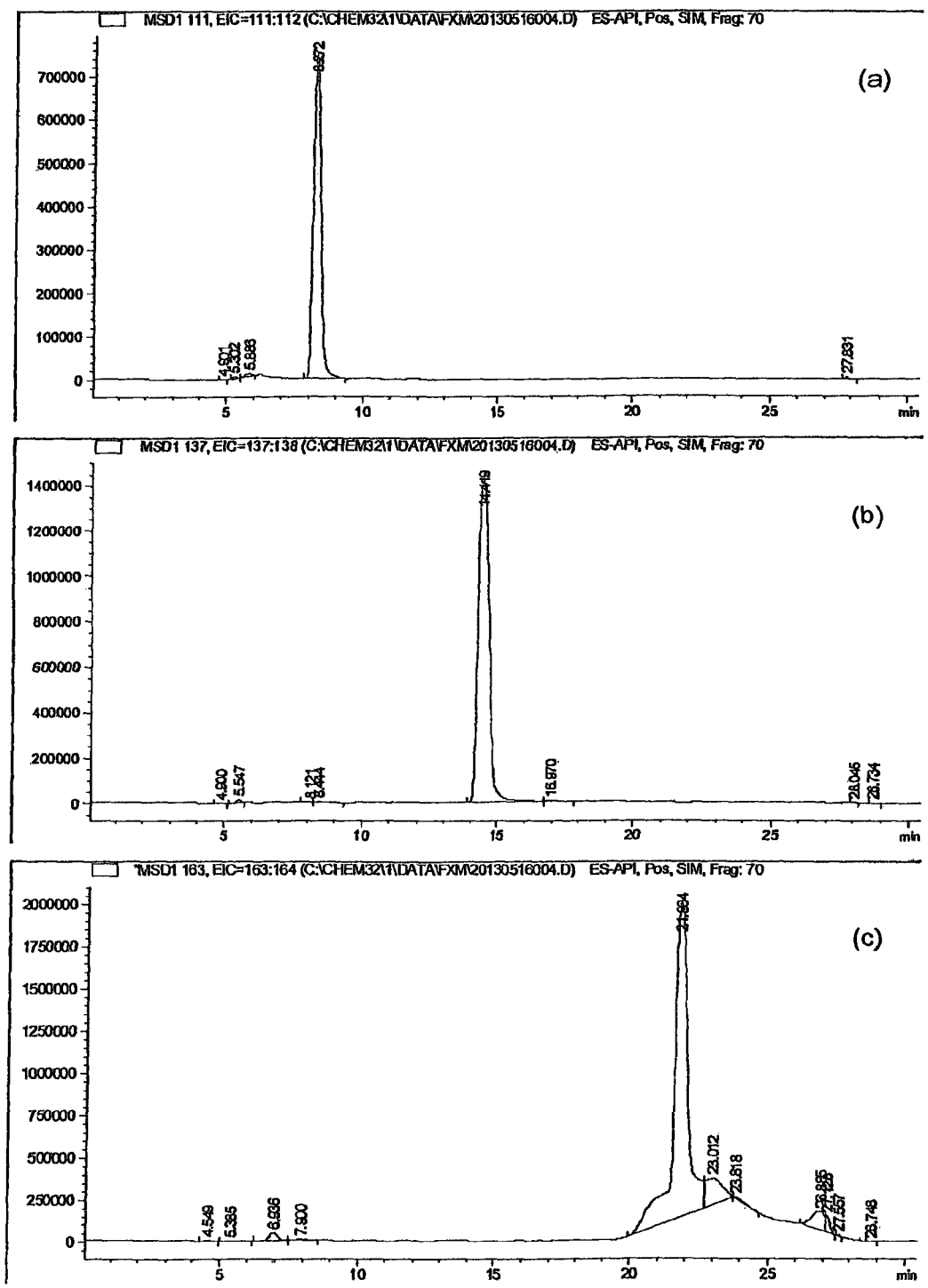
FIG. 20 (to be roughly compared to FIGS. 15 and 18) shows the LC-MS analysis for a solution prepared from GP+Precursor-1 (methiin)+Precursor-2 (allicin)

FIG. 20: Sample: 3.0 g GP added to a solution of a mixture of 200 mg Precursor-1 (methiin)+200 mg Precursor-2 (alliin) in 35 ml water. Channels: (a) m/z 111 specific for detecting methyl methyl-thiosulfinate (b) for Analogue-1 (MA-AM) and (c) for Analogue-2 (allicin). Note: Rising baseline in channel (c)—possibly due to impurity in mobile phase. In FIG. 20 there are strong signals in all the m/z channels: 111, 137 and 163. The peaks are in the correct relative retention time order. This result is consistent with high levels of formation of the methyl methyl-thiosulfinate, Analogue-1 (MA-AM) and Analogue-2 (allicin) that would be predicted taking into account the relevant thiosulfinate formation chemistry applicable for this specific reaction mixture.

From these results it can be concluded:
1. There is strong evidence to suggest that the peak at retention time approx. 2.5 min is methyl methyl-thiosulfinate.
2. Both the levels of formation of the methyl methyl-thiosilfinate species and of Analogue-2 (allicin) relative to the level of formation of Analogue-1 will be influenced by the specific quantities of Precursor-1 (methiin) and Precursor-2 (alliin) to be contacted with a source of allinase, and the reaction time used.

Process 5
Process 5.1

Concentrations of Analogue-1 (mixture of allyl methyl thiosulfinate and methyl allyl-thiosulfinate; this mixture is also called MA-AM) and Analogue-2 (allicin) are increased to various levels by contacting an aqueous solution of various synthetic mixtures of Precursor-1 (P-1; methiin) and Precursor-2 (P-2; alliin) with a source of allinase using appropriate reaction times.
1. Source of allinase—garlic powder (GP).
2. For comparative purposes:
(a) Garlic powder (3.0 g) is added to various solutions of Precursor-1 and Precursor-2 first dissolved in 35 ml water.
N.B—With the exception of a solution containing only 3.0 g of GP, the other solutions used contained a constant quantity of Precursor-1 (200 mg) but varying quantities of Precursor-2 (50-200 mg). The reaction solutions were stirred with a magnetic stir bar. At 60, 120, 180 and 240 minute intervals—samples were withdrawn and analysed by quantitative HPLC. The results are summarized in Tables 5-10. A representative complete set of 4 chromatograms (used to construct Table 9) is shown in FIGS. 28-31. Tables 5-10 also include data for the peak with approximate retention time of 2.5 minutes, previously identified as methyl methyl-thiosulfinate [$CH_3S(O)SCH_3$] whose structural formula can also be represented as MeS(O)SMe] and from now also referred to as Analogue-4. The structure of Analogue-3 is given in the previous patent application. Analogue-3 thus far has not been produced by GP itself but as the study extends to the use of fresh garlic tissue using mixtures of P-1 and P-2 its detection is anticipated.

Figure 21:
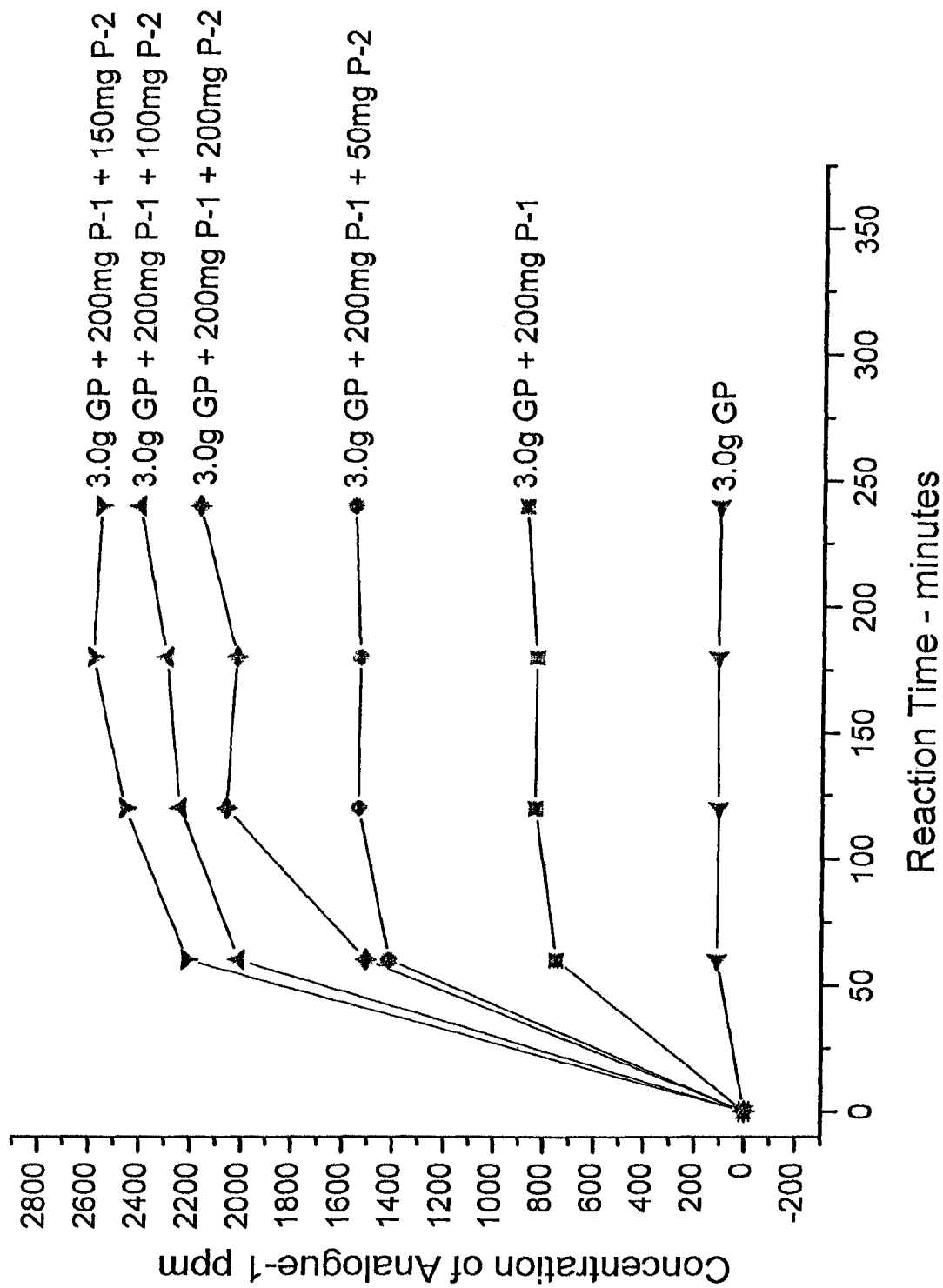
FIG. 21 shows the rate of production for Analogue-1 for various solutions contacted with 3.0 g GP, each of the ×6 aqueous solutions having different total concentrations of Precursor-1 (P-1) and Precursor-2 (P-2); rate of production of Analogue-1.
Figure 22:
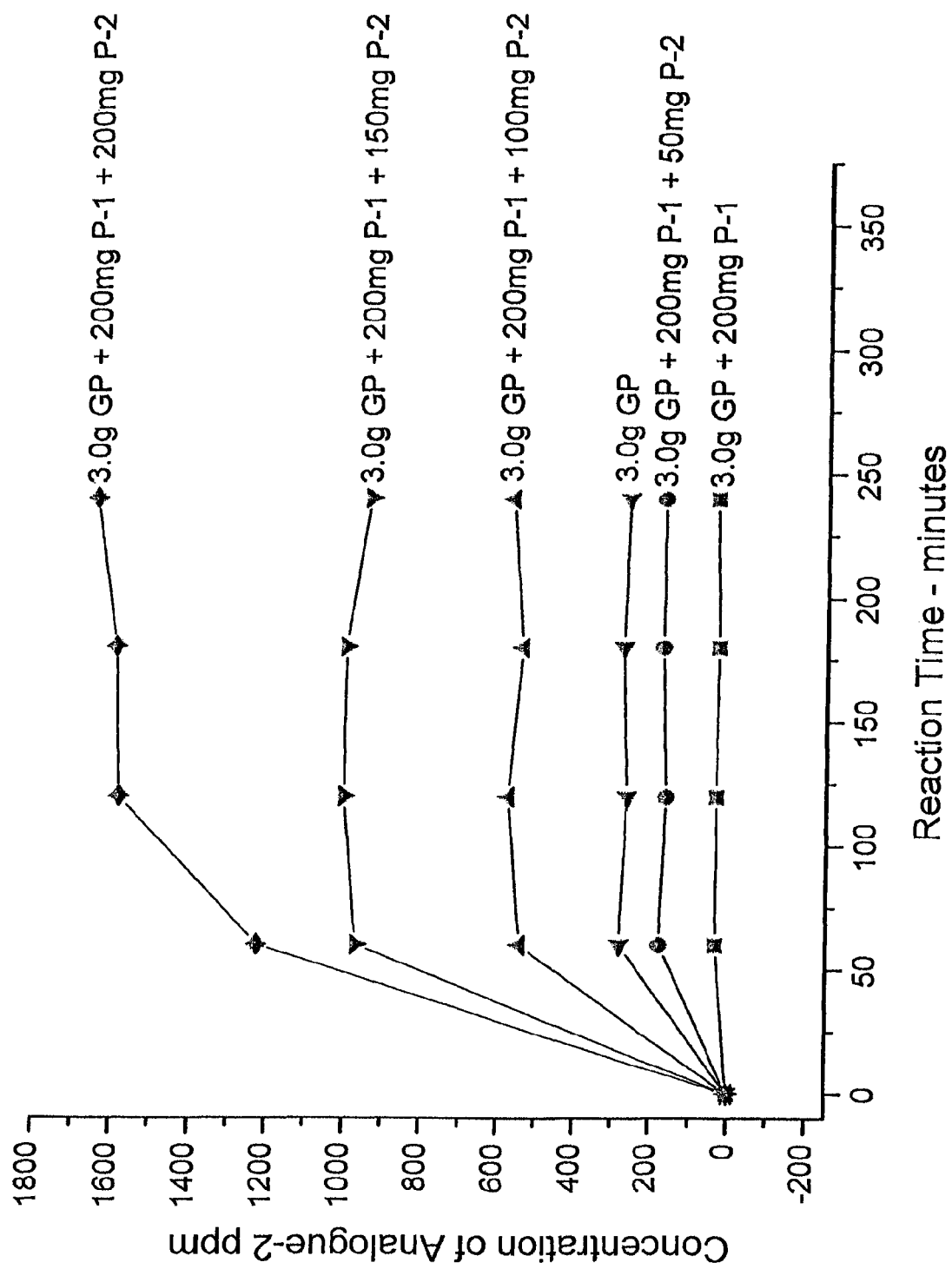
FIG. 22 shows the rate of production for Analogue-2 for various solutions contacted with 3.0 g GP, each of the ×6 aqueous solutions having different total concentrations of Precursor-1 (P-1) and Precursor-2 (P-2); rate of production of Analogue-2.

Treatment of Data Provided in Tables 5-10:

Various graphs have been constructed and inspection of FIGS. 21-23 reveals that for Analogue-1, Analogue-2 and Analogue-4 production—using the conditions employed—reaction can be generally considered to be approximately complete after 3 hrs of mixing. Stemming from this observation a fourth very informative graph as depicted in FIG. 24 can be constructed. The 3 hour concentration values can now be selected from Tables 5-10 to construct FIG. 24. FIG. 24 illustrates several important points:
1. Maximum production of Analogue-1 is obtained from a mixture utilizing 3.0 g GP+200 mg P-1+150 mg P-2.
2. The concentration of Analogue-4 produced declines in a linear manner as the concentration of P-2 incrementally increases. This would be expected since the allyl sulfenic acid produced from Precursor-2 (on contacting with allinase) would react very quickly with methyl sulfenic acid produced from Precursor-1. In other words with higher concentrations of allyl sulfenic acid the tendency for two molecules of methyl sulfenic acid to react to produce Analogue-4 are reduced. From a basic "wet chemistry" perspective this observation lends yet further support to ("tallies with") the LC/MS data presented for PROCESS 4 above.
3. Why should the production of Analogue-1 show a maximum value? This is probably related to the speed of formation of the relevant sulfenic acids from P-1 and P-2 and then their following individual reaction speeds (kinetics) in forming the various thiosulfinates. It is well documented that Precursor-2 very rapidly forms allyl sulfenic acid when contacted with allinase whereas Precursor-1 reacts more slowly with allinase to produce methyl sulfenic acid.
4. Inspection of Table 5 reveals that 3.0 g GP would produce approximately 273 ppm of Analogue-2 after 3 hours reaction time—a single "diamond data point" is shown in FIG. 24 to denote this value. Using this point for extrapolation it is estimated that the addition of more than approximately 75 mg of P-2 to a mixture of 3.0 g GP+200 mg P-1 would be the point at which more than 273 ppm of Analogue-2 would be formed.
5. The graphs shown in FIG. 24 are of the type that can provide a valuable prediction aid concerning the relatively complex outcome of contacting GP with various mixtures of P-1 and P-2.

Conclusions:
1. The data categorically demonstrates the feasibility of controlling an almost totally synthetic reaction to produce Analogue-1 and Analogue-2 using GP as the source of allinase.
2. Reaction time can be controlled to maximize yields of Analogue-1, Analogue-2 and Analogue-4.
3. As summarized in FIG. 24, a wide range of different and very novel aqueous based liquid types can be prepared containing different concentrations of Analogue-1, Analogue-2 and Analogue-4. In fact different types of liquids produced by contacting varying quantities of P-1 and P-2 with GP could be blended to greatly extend the range of products.
4. The major unanticipated finding relates to the formation of Analogue-4. This may in fact be serendipitous since it is documented that Analogue-4 is biologically active. In other words, deliberately manufactured Analogue-4 may provide real commercial potential. Accordingly, this provides a new set of standards for urgent bioassays. One of these standards has a high Analogue-4 concentration—this liquid was made from a diluted type shown in Table 6.

5. The GP (McCormick a Chinese brand) used throughout these studies was obtained at a local store. It may well transpire that other more carefully screened GPs may provide higher intrinsic P-1 and P-2 concentrations and far more importantly better allinase activity once hydrated.

TABLE 5

GP (3.0 g)

| Reaction Time Min | A-1 Concentration ppm | A-2 Concentration ppm | Peak Retention Time (R.T.) = 2.5 min (corresponding to A-4 Concentration) Integration Value × $10^{-4}$ |
|---|---|---|---|
| 60 | 110 | 281 | — |
| 120 | 107 | 262 | — |
| 180 | 110 | 273 | — |
| 240 | 106 | 260 | — |

TABLE 6

GP (3.0 g) + P-1 (200 mg)

| Reaction Time Min | A-1 Concentration ppm | A-2 Concentration ppm | A-4 Concentration Integration Value × $10^{-4}$ |
|---|---|---|---|
| 60 | 752 | 31 | 932 |
| 120 | 836 | 30 | 1104 |
| 180 | 835 | 26 | 1118 |
| 240 | 876 | 30 | 1163 |

TABLE 7

GP (3.0 g) + P-1 (200 mg) + P-2 (50 mg)

| Reaction Time Min | A-1 Concentration ppm | A-2 Concentration ppm | A-4 Concentration Integration Value × $10^{-4}$ |
|---|---|---|---|
| 60 | 1415 | 177 | 681 |
| 120 | 1541 | 161 | 824 |
| 180 | 1538 | 170 | 855 |
| 240 | 1562 | 168 | 873 |

TABLE 8

GP (3.0 g) + P-1 (200 mg) + P-2 (100 mg)

| Reaction Time Min | A-1 Concentration ppm | A-2 Concentration ppm | A-4 Concentration Integration Value × $10^{-4}$ |
|---|---|---|---|
| 60 | 2012 | 543 | 514 |
| 120 | 2248 | 574 | 670 |
| 180 | 2307 | 538 | 710 |
| 240 | 2417 | 566 | 707 |

TABLE 9

GP (3.0 g) + P-1 (200 mg) + P-2 (150 mg)

| Reaction Time Min | A-1 Concentration ppm | A-2 Concentration ppm | A-4 Concentration Integration Value × $10^{-4}$ |
|---|---|---|---|
| 60 | 2215 | 968 | 433 |
| 120 | 2465 | 1002 | 506 |
| 180 | 2597 | 998 | 551 |
| 240 | 2570 | 937 | 564 |

TABLE 10

GP (3.0 g) + P-1 (200 mg) + P-2 (200 mg)

| Reaction Time Min | A-1 Concentration ppm | A-2 Concentration ppm | A-4 Concentration Integration Value × $10^{-4}$ |
|---|---|---|---|
| 60 | 1508 | 1225 | 212 |
| 120 | 2067 | 1584 | 280 |
| 180 | 2031 | 1593 | 287 |
| 240 | 2180 | 1648 | 311 |

Process 5.2

The manufacture of Analogue-2 (allicin) is boosted by contacting allinase provided by GP (garlic powder) with Precursor-2. The possibility of using less than 3.0 g GP in 35 ml water to manufacture both Analogue-1 and Analogue-2 is investigated. Potential benefits include (i) easier separation of the liquid from hydrated GP at the end of the reaction period and (ii) improving the colour of the liquid manufactured.

1. Source of allinase is garlic powder (GP).
2. For comparative purposes:
   (a) The compositions of the solutions, all prepared in 35 ml of water, are provided in the headers of Tables 11-16. At 60, 120, 180 and 240 minute intervals samples were withdrawn and analyzed by quantitative HPLC. The results are summarized in Tables 11-16. A representative complete set of 4 chromatograms (to go with Table 14) is also included. Tables 11-16 also include data for the peak with approximate retention time of 2.5 minutes, previously identified as methyl methyl-thiosulfinate [$CH_3S(O)SCH_3$ i.e. MeS(O)SMe] and now also referred to as Analogue-4. The structure of Analogue-3 is $CH_2=CH-CH_2-S(O)-S-CH=CH-CH_3$ whose abbreviation is AllS(O)SPn-(E,Z), as given already further above.

Treatment of Data Provided in Tables 11-16:

Various graphs have been constructed:

FIG. 25 has been constructed using the data given in Tables 11-16. These graphs illustrate that in the case of Analogue-2 formed from 200 mg P-2 both 3.0 g GP and 1.0 g GP contain sufficient allinase for the conversion of this quantity of P-2 to Analogue-2. The four graphs use the raw data given in Tables 13-14 and also show the corrected graphs when the Analogue-2 concentrations given in Tables 11-12 for either 3.0 g GP or 1.0 g GP are deducted.

For example, for graph —C— in FIG. 25, at 60 min the corrected concentration for Analogue-2 is calculated as (2042-101) ppm. Then next for —C—, at 120 min the corrected concentration for Analogue-2 is calculated as (2302-92) ppm etc.

Under "mass balance calculations" further below the conversion of P-2 to Analogue-2 is illustrated as a very efficient process.

FIG. 26 has been constructed using the data given in Tables 10 (see Process 5.1) and 15. As indicated in Table 15 virtually no allinase activity was detected after 60 min reaction time. Consequently immediately after the third sample was taken at 180 min (third sample taken to confirm no significant allinase activity) a further 1.0 g GP was added to the reaction mixture. Comparison of graphs B and D (for Analogue-1) then E and C (for Analogue-2) shown in FIG. 26 confirm that the addition of a further 1.0 g GP at 180 min restored allinase activity resulting in yields of Analogue-1 and Analogue-2 at 240 min closely approximating those that had been obtained using 3.0 g GP. This is potentially an important finding: unlike the situation described for FIG. 25, it would appear that the initial addition of 1.0 g GP to a mixture of (200 mg P-1+200 mg P-2) did not provide sufficient allinase activity. This may be due to the ability of Analogue-1 and/or Analogue-4 to more effectively and rapidly stop the action of allinase (when the enzyme is initially present at lower levels) compared to Analogue-2.

FIG. 27 has been constructed using the data in Tables 6 (see Process 5.1) and 16. FIG. 27 confirms that GP does not contain sufficient P-2 to make a very strong solution of Analogue-1—recall that Analogue-1 (MA-AM) is formed by the condensation reaction between methyl sulfenic acid and allyl sulfenic acid produced when allinase contacts P-1 and P-2 respectively. However, visual inspection of the data shown in Table 6 (see Process 5.1) demonstrates that contacting 3.0 g GP with 200 mg P-1 produced the strongest strength solution of Analogue-4. This is because a self condensation reaction between two molecules of methyl sulfenic acid is more likely to occur with this reaction mixture. A diluted solution of the type Table 6 refers to has been supplied for bioassay.

Conclusions:

1. Contacting an aqueous solution of P-2 with GP is an effective and rapid means to produce an aqueous solution of Analogue-2. The yield of Analogue-2 is high (see Mass Balance Calculations).
2. Conversion of P-2 to Analogue-2 can be efficiently and rapidly achieved using reduced quantities of GP, to provide the same yield of Analogue-2 that a larger quantity of GP can provide. See previous notes concerning FIG. 25.
3. Compared to an aqueous solution containing only P-2, for solutions containing both P-1 and P-2 higher quantities of GP are required to attain maximum yields of Analogue-1 combined with Analogue-2.
4. Related to preceding point: Analogue-1 and/or Analogue-4 appear to be more efficient in preventing allinase activity than Analogue-2. See previous notes concerning FIG. 26.
5. By treating a solution containing only P-1 with GP, apart from Analogue-1, Analogue-4 can be produced in high quantity. See previous notes concerning FIG. 27.
6. The GP (McCormick a Chinese brand) used throughout these studies was obtained at a local store. It may well transpire that other more carefully screened GPs may provide higher intrinsic P-1 and P-2 concentrations and far more importantly better allinase activity once hydrated.
7. The colour of the liquid produced is directly influenced by the quality and quantity of GP used.

TABLE 11

(same as for Table 5). GP (3.0 g)

| Reaction Time Min | A-1 Concentration ppm | A-2 Concentration ppm | A-4 Concentration Integration Value × $10^{-4}$ |
|---|---|---|---|
| 60 | 110 | 281 | — |
| 120 | 107 | 262 | — |

TABLE 11-continued (same as for Table 5). GP (3.0 g)

| Reaction Time Min | A-1 Concentration ppm | A-2 Concentration ppm | A-4 Concentration Integration Value × $10^{-4}$ |
|---|---|---|---|
| 180 | 110 | 273 | — |
| 240 | 106 | 260 | — |

TABLE 12

GP (1.0 g)

| Reaction Time Min | A-1 Concentration ppm | A-2 Concentration ppm | A-4 Concentration Integration Value × $10^{-4}$ |
|---|---|---|---|
| 60 | 38 | 101 | — |
| 120 | 37 | 92 | — |
| 180 | 36 | 89 | — |
| 240 | 37 | 90 | — |

TABLE 13

GP (3.0 g) + P-2 (200 mg)

| Reaction Time Min | A-1 Concentration ppm | A-2 Concentration ppm | A-4 Concentration Integration Value × $10^{-4}$ |
|---|---|---|---|
| 60 | 141 | 2473 | — |
| 120 | 139 | 2342 | — |
| 180 | 152 | 2536 | — |
| 240 | 150 | 2545 | — |

TABLE 14

GP (1.0 g) + P-2 (200 mg)

| Reaction Time Min | A-1 Concentration ppm | A-2 Concentration ppm | A-4 Concentration Integration Value × $10^{-4}$ |
|---|---|---|---|
| 60 | 49 | 2042 | — |
| 120 | 53 | 2302 | — |
| 180 | 54 | 2400 | — |
| 240 | 55 | 2409 | — |

TABLE 15

GP (1.0 g)** + P-1 (200 mg) + P-2 (200 mg)

| Reaction Time Min | A-1 Concentration ppm | A-2 Concentration ppm | A-4 Concentration Integration Value × $10^{-4}$ |
|---|---|---|---|
| 60 | 1179 | 1071 | 132 |
| 120 | 1187 | 980 | 140 |
| 180** (+1.0 GP) | 1260 | 1054 | 140 |
| 240 | 2302 | 1547 | 307 |

**After sample withdrawn at 180 min, an additional 1.0 g garlic powder added. Action taken since between 60-120 min no significant allinase activity detected. The results at 240 min confirm that the addition of 1.0 g GP at 180 min provided fresh allinase activity.

TABLE 16

GP (1.0 g) + P-1 (200 mg)

| Reaction Time Min | A-1 Concentration ppm | A-2 Concentration ppm | A-4 Concentration Integration Value × $10^{-4}$ |
|---|---|---|---|
| 60 | 328 | — | 801 |
| 120 | 315 | — | 896 |
| 180 | 326 | — | 978 |
| 240 | 326 | — | 997 |

An example of a representative complete set of four chromatograms now follows in FIGS. 28-31. This set of chromatograms provided the data to construct Table 9.

The reaction conditions employed (3.0 g GP+200 mg P-1+150 mg P-2) produced the liquid with highest Analogue-1 concentration—see FIG. 24.

A further example of a representative complete set of ×4 chromatograms now follows in FIGS. 32-35. This set of chromatograms provided the data to construct Table 14.

The reaction conditions employed produced the liquid with highest Analogue-2 concentration (note the small difference between using 3.0 g GP and 1.0 g GP to contact 200 mg P-2 is most probably related to experimental errors)—after a correction had been made for the quantity of Analogue-2 GP intrinsically produces by itself—see FIG. 25 (corrected graph with black circle data points).

Process 5—Appendix (Mass Balance Calculations):

A fully worked specimen calculation is applied to the reaction mixture of (3.0 g GP+200 mg P-2) to determine the theoretical efficiency of producing Analogue-2. The calculation will involve considering the concentration determined for Analogue-2 after 3 hrs reaction time in Table 9. Also the concentration determined for Analogue-2 after 3 hrs reaction time in Table 7 is required.

Before the calculation is presented the following information is also required:

Relative Molecular Weight of Analogue-2 is 162 i.e. 1 mole weighs 162 g

Relative Molecular Weight of P-2 is 177 i.e. 1 mole weighs 177 g

Basic Chemical Equation for Analogue-2 synthesis is:

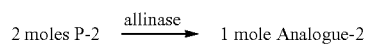

With the above information the calculation is as follows:

200 mg $P$-2=0.2/177 mole $P$-2

Therefore number of moles Analogue-2 produced at 100% efficiency level is:

Theoretical Maximum Analogue Yield=0.5×(0.2/177) moles Analogue-2

Or theoretical Maximum Analogue Yield=0.5×(0.2/177)× 162 g Analogue-2

This would equate to 0.092 g Analogue-2 in 35 ml water.

We now convert the above concentration to equivalent g/L concentration:

Hence, Maximum Yield for Analogue-2 in equivalent g/L=0.092×(1000/35)=2.629 g/L

In other words maximum theoretical concentration for fully converting 200 mg P-2 into Analogue-2 is 2629 ppm After 3 hr measured concentration (see Table 9) is 2536 ppm of which 273 ppm (Table 7) would be expected to be obtained from the P-2 converted to Analogue-2 in 3.0 g GP Therefore Experimentally Determined Conversion Efficiency = [(2536 − 273)/2629]100 = 86% Efficiency*

* This efficiency calculation is based upon using the HPLC Method described above.

In April 2013 the inventors compared the results for their HPLC Method against the official British Pharmacopeia HPLC Method and it was demonstrated that the inventors' HPLC METHOD provided a lower value of 90% when compared to the official BP HPLC Method, meaning that 86% inventors Efficiency=95.6% Efficiency by the BP HPLC Method.

The BP HPLC METHOD due to its chromatographic mobile phase conditions is not capable of providing a chromatogram showing resolved peaks for both Analogue-1 and Analogue-4. It is strictly designed to measure Analogue-2 content in garlic powder.

Process 6

Process 6.A

Boosting of Analogue-1 (A-1; mixture of allyl methyl thiosulfinate and methyl allyl-thiosulfinate; this mixture is also called MA-AM) and Analogue-2 (A-2; allicin) concentrations to various levels by contacting an aqueous solution of various synthetic mixtures of Precursor-1 (P-1; methiin) and Precursor-2 (P-2; alliin) with a source of allinase—in this process specifically fresh garlic bulb tissue—is investigated while also determining appropriate reaction times.

1. Source of allinase—fresh garlic (FG), minced using a domestic garlic press. N.B. Only minced garlic tissue that had been forced through the perforated face of the press was used. Larger pieces were discarded. Timing was important—the method protocol involved contacting weighed, freshly minced garlic with aqueous solutions before 2 minutes had lapsed from the time when garlic mincing had commenced.

Source and type of garlic: Harvested Shandong Province—Early Summer Crop. See FIG. 52.

2. Initial experiments were performed to determine the mass of minced fresh garlic (FG) that would provide equivalent performance characteristics to 3.0 g garlic powder that had been widely used in the experiments to generate the data presented for Process 5 above. Appendix 1 presents details of these initial experiments.

It was determined that 6.0 g minced fresh garlic of the type used in these studies provided equivalent performance to 3.0 g garlic powder of the type previously used.

3. For comparative purposes: Experiments for Process 5 generally involved adding 3.0 g garlic powder to solutions of P-1 and P-2 prepared in 35 ml water:

(a) For this Process Section A minced fresh garlic (12.0 g) was added to various solutions of Precursor-1 and Precursor-2 first dissolved in 70 ml water. N.B—With the exception of a solution containing only 12.0 g FG, the other solutions used contained a constant quantity of Precursor-1 (400 mg) but varying quantities of Precursor-2 (100-400 mg).

N.B. Due to sampling considerations the standard solutions made using FG were of equivalent composition w.r.t. to P-1 and P-2 concentrations to those prepared for Process 5.1 that utilized garlic powder. The volume of water (70 ml) used to prepare the FG standard solutions prepared was twice that previously used (35 ml) to prepare the standard solutions treated with garlic powder.

The reaction solutions were stirred with a magnetic stir bar. At 60, 120, 180 and 240 minute intervals—samples were withdrawn and analysed by quantitative HPLC. The results are summarized in Tables 17-21. A representative complete set of 4 chromatograms (used to construct Table 20) are also included. Tables 17-21 also include data for the peak with approximate retention time of 2.5 minutes, previously identified as methyl methyl-thiosulfinate [CH$_3$S(O)SCH$_3$ whose structural formula can also be represented as MeS(O)SMe] and from now also referred to as Analogue-4. The structure of Analogue-3 is CH$_2$=CH—CH$_2$—S(O)—S—CH=CH—CH$_3$ named 1-propenyl-(E,Z) allyl-thiosulfinate whose abbreviation is AllS(O)SPn-(E,Z), and whose geometric isomers are collectively referred to as Analogue-3.

Treatment of Data Provided in Tables 13-17:
1. Various graphs have been constructed—these largely mirror those presented in FIGS. 21-24.
2. In order to facilitate ease of comparison with FIGS. 21-24 the quantities of FG, P-1 and P-2 shown in the graphs in FIGS. 36-39 are those that would be present had only 35 ml water been used to prepare lower volume solutions of the same composition. Inspection of FIGS. 33-37 reveals that for Analogue-1, Analogue-2 and Analogue-4 production—using the conditions employed—reaction can be generally considered to be approximately complete after 3 hrs of mixing.

Based on the above observation (same as for garlic powder) and was explained for Process 5, FIG. 39 was constructed. FIG. 39 shows identical characteristics to those previously shown and discussed for FIG. 24 (see Process 5), hence discussion of these points will not be duplicated here.
Process 6.A—Conclusions:
(Conclusions 1-4 below are the same that were derived for Process 5.1 except they now apply to the use of FG).
1. The data categorically demonstrates the feasibility of controlling an almost totally synthetic reaction to produce Analogue-1 and Analogue-2 using FG as the source of allinase.
2. Reaction time can be controlled to maximize yields of Analogue-1, Analogue-2 and Analogue-4.
3. As summarized in FIG. 39, a wide range of different and very novel aqueous based liquid types can be prepared containing different concentrations of Analogue-1, Analogue-2 and Analogue-4. In fact different types of liquids produced by contacting varying quantities of P-1 and P-2 with FG could be blended to greatly extend the range of products.
4. The major unanticipated finding relates to the formation of Analogue-4. This may in fact be serendipitous since it is documented that Analogue-4 is biologically active. In other words, deliberately manufactured Analogue-4 may provide real commercial potential. Accordingly, this provides a new set of standards for urgent bioassays. One of these standards has a high Analogue-4 concentration—this liquid was made from a diluted type shown in Table 6 (see Process 5).
Additional Conclusion:
5. Though not described within this section an additional experiment was performed—this entailed delaying the introduction of freshly minced and weighed fresh garlic into a solution (400 mg P-1+400 mg P-2+70 ml water) until 5 minutes (not 2 minutes) after the mincing had commenced. The resultant reaction solutions provided significantly higher concentrations of A-2 than those shown in Table 17. There are important consequences to this observation—see Appendix 2 for details.

TABLE 17

FG (12.0 g)

| Reaction Time Min | A-1 Concentration ppm | A-2 Concentration ppm | A-4 Concentration Integration Value × 10$^{-4}$ |
|---|---|---|---|
| 60 | 102 | 393 | — |
| 120 | 105 | 378 | — |
| 180 | 113 | 426 | — |
| 240 | 110 | 391 | — |

TABLE 18

FG (12.0 g) + P-1 (400 mg) + P-2 (100 mg)

| Reaction Time Min | A-1 Concentration ppm | A-2 Concentration ppm | A-4 Concentration Integration Value × 10$^{-4}$ |
|---|---|---|---|
| 60 | 1854 | 312 | 842 |
| 120 | 1928 | 293 | 936 |
| 180 | 1924 | 276 | 963 |
| 240 | 1926 | 270 | 991 |

TABLE 19

FG (12.0 g) + P-1 (400 mg) + P-2 (200 mg)

| Reaction Time Min | A-1 Concentration ppm | A-2 Concentration ppm | A-4 Concentration Integration Value × 10$^{-4}$ |
|---|---|---|---|
| 60 | 2096 | 512 | 594 |
| 120 | 2146 | 532 | 682 |
| 180 | 2328 | 574 | 727 |
| 240 | 2299 | 558 | 762 |

TABLE 20

FG (12.0 g) + P-1 (400 mg) + P-2 (300 mg)

| Reaction Time min | A-1 Concentration ppm | A-2 Concentration ppm | A-4 Concentration Integration Value × 10$^{-4}$ |
|---|---|---|---|
| 60 | 2103 | 1051 | 392 |
| 120 | 2349 | 1120 | 447 |
| 180 | 2437 | 1128 | 465 |
| 240 | 2408 | 1124 | 473 |

TABLE 21

FG (12.0 g) + P-1 (400 mg) + P-2 (400 mg)

| Reaction Time Min | A-1 Concentration ppm | A-2 Concentration ppm | A-4 Concentration Integration Value × 10$^{-4}$ |
|---|---|---|---|
| 60 | 1961 | 1586 | 249 |
| 120 | 2010 | 1618 | 256 |
| 180 | 1978 | 1578 | 255 |
| 240 | 2025 | 1618 | 260 |

An example of a representative complete set of ×4 chromatograms now follows in FIGS. 40-43. This set of chromatograms provided the data to construct Table 20.

Of the reaction conditions employed, 12.0 g FG+400 mg P-1+350 mg P-2+70 ml water produced the liquid with highest Analogue-1 concentration after 3 hours reaction (see FIG. 39).

The data provided by FIGS. 40-43 were also used to construct the graphs shown in FIGS. 36-38, but were labelled as being produced from the half-volume equivalent solution, i.e. [6.0 g FG+200 mg P-1+200 mg P-2+35 ml water].

Process 6.B

In the following solutions of P-1 are contacted with minced fresh garlic to boost the production of Analogue-1. In doing so, Analogue-4 is also manufactured. Further, the relationship between the mass of minced fresh garlic and the yields of Analogue-1 and Analogue-4 are determined and reaction time data obtained.

Method:

1. Source of allinase and P-1 fresh garlic (FG), minced using a domestic garlic press.

N.B. Only minced garlic tissue that had been forced through the perforated face of the press was used. Larger pieces were discarded. Timing was important—the method protocol involved contacting weighed, freshly minced garlic with aqueous solutions before 2 minutes had lapsed from the time when garlic mincing had commenced.

Source and type of garlic: Harvested Shandong Province—Early Summer Crop. See FIG. 52.

2. Various masses of minced fresh garlic (6.0 g-24.0 g) were added to separate solutions each containing 400 mg Precursor-1 dissolved in 70 ml water.

The reaction solutions were stirred with a magnetic stir bar. At 60, 120, 180 and 240 minute intervals—samples were withdrawn and analysed by quantitative HPLC. The results are summarized in Tables 22-25. Tables 22-25 also include data for the peak with approximate retention time of 2.5 minutes, previously identified as methyl methyl-thiosulfinate [$CH_3S(O)SCH_3$ whose structural formula can also be represented as $MeS(O)SMe$] and herein also referred to as Analogue-4. The structure of Analogue-3 is given elsewhere herein.

Treatment of Data Provided in Tables 22-25:

1. Various graphs have been constructed.
2. In order to facilitate ease of comparison—the quantities of FG and P-1 and shown in the graphs in FIGS. 44-47 are those that would be present had only 35 ml water been used to prepare lower volume solutions of the same composition.

Inspection of FIGS. 44-46 reveals that for Analogue-1 and Analogue-4 production—using the conditions employed, reaction can be generally considered to be approximately complete after 3 hrs of mixing.

Based on the above observation FIG. 47 can be constructed and shows the concentrations of Analogue-1, Analogue-2 and Analogue-4 determined at 3 hours as a function of the mass of FG used. Inspection of the graphs shown in FIG. 47 reveals:

1. For the range of different masses of FG studied the concentrations of Analogue-1 and Analogue-2 show a linear increase as the amount of FG is increased.
2. There is a small linear decrease in the amount of Analogue-4 produced.

Conclusions:

1. Mixing solutions of P-1 with FG is an effective means of producing liquids with high Analogue-1 and Analogue-4 content but with low Analogue-2 content.
2. A very large mass of FG would be required to boost Analogue-2 content using this method. Such mixtures would be slurries.

3. If a liquid was required that would provide a high (greater than 1000 ppm) Analogue-1 and Analogue-2 content, liquids prepared by contacting only P-1 with FG would have to be blended with liquids separately manufactured to provide high Analogue-2 content e.g. liquids manufactured by contacting solutions of P-2 with garlic powder.

4. And so concerning Process 1 and 2 in this patent application this showed a modest increase in Analogue-1 production with relatively high Analogue-2 concentration. The processes 1 and 2 cannot be directly compared with this study since the quantity of P-1 used in Processes 1 and 2 was very small and the reaction dynamics were completely different—the P-1 used in Processes 1 and 2 was added not at the start of the reaction but sometime after the reaction of FG in water had been initiated by which time Analogue-2 had been independently preformed. Clearly in Processes 1 and 2 timing was such that when P-1 was added, sufficient P-2 was still available to give rise to the enhancement in Analogue-1 concentration. The point being that this current process uses more controlled conditions to enhance the manufacture of Analogue-1 by contacting solutions of P-1 with fresh garlic at the start of the reaction period.

TABLE 22

| FG (6.0 g) + P-1 (400 mg) | | | |
|---|---|---|---|
| Reaction Time Min | A-1 Concentration ppm | A-2 Concentration ppm | A-4 Concentration Integration Value × $10^{-4}$ |
| 60 | 474 | 21 | 901 |
| 120 | 531 | 18 | 1065 |
| 180 | 537 | 18 | 1098 |
| 240 | 543 | 19 | 1123 |

TABLE 23

| FG (12.0 g) + P-1 (400 mg) | | | |
|---|---|---|---|
| Reaction Time Min | A-1 Concentration ppm | A-2 Concentration ppm | A-4 Concentration Integration Value × $10^{-4}$ |
| 60 | 807 | 47 | 1065 |
| 120 | 832 | 45 | 1131 |
| 180 | 841 | 45 | 1151 |
| 240 | 843 | 47 | 1153 |

TABLE 24

| FG (18.0 g) + P-1 (400 mg) | | | |
|---|---|---|---|
| Reaction Time Min | A-1 Concentration ppm | A-2 Concentration ppm | A-4 Concentration Integration Value × $10^{-4}$ |
| 60 | 1086 | 102 | 989 |
| 120 | 1136 | 103 | 1042 |
| 180 | 1159 | 112 | 1051 |
| 240 | 1112 | 111 | 1015 |

TABLE 25

FG (24.0 g) + P-1 (400 mg)

| Reaction Time Min | A-1 Concentration ppm | A-2 Concentration ppm | A-4 Concentration Integration Value × $10^{-4}$ |
|---|---|---|---|
| 60 | 1333 | 169 | 1011 |
| 120 | 1325 | 170 | 1013 |
| 180 | 1378 | 176 | 1052 |
| 240 | 1396 | 173 | 1038 |

The set of chromatograms used to construct the graphs shown in FIG. 27 follows. These 4 chromatograms were obtained after 3 hour reaction period and involved contacting 6.0-24.0 g FG with 400 mg P-1 that had been dissolved in 70 ml water.

The x-axis for the graphs shown in FIG. 47 was labelled as being produced from the half-volume equivalent solution i.e. 3.0-12.0 g FG with 200 mg P-1 dissolved in 35 ml water. Process 6—Appendix 1

Experiments to determine the mass of the type of minced fresh garlic used in these studies that would provide equivalent allinase activity to 3.0 g of the type of garlic powder used to generate the data presented for Process 5.

The initial assumption made as a start point was that 3.0 g FG would provide equivalent allinase activity to 3.0 g garlic powder.

Preparation and use of minced fresh garlic: Only minced garlic tissue that had been forced through the perforated face of a small domestic press was used. Larger pieces were discarded. Timing was important—the method protocol involved contacting weighed, freshly minced garlic with aqueous solutions before 2 minutes had lapsed from the time when garlic mincing had commenced.

In order to test the initial assumption and using Process 5 as a reference point it was decided that the equivalent of 3.0 g minced fresh garlic should be contacted with an aqueous solution with the equivalent composition of [200 mg P-1+ 150 mg P-2+35 ml water]since this aqueous solution had provided the highest yield of Analogue-1 in the study involving garlic powder.

Table 26 summarises the results obtained. If compared to Table 9 (see Process 5) visual inspection of these two Tables reveals that little correlation exists in terms of the production of Analogue-1, Analogue-2 and Analogue-4.

Following this finding it was decided that various masses of minced fresh garlic should be mixed with 70 ml water and the results obtained should be compared with the equivalent results obtained by mixing 3.0 g garlic powder in 35 ml water.

Tables 27-30 summarize the data obtained for mixing 2.0-24.0 g FG in 70 ml water. Inspection of the Analogue-1 concentrations reveals that 12.0 g FG in 70 ml water provides the closest match to 3.0 g garlic powder in 35 ml water (Table 5 also shown for comparison). In other words 6.0 g FG in 35 ml water approximately equates to 3.0 g garlic powder in 35 ml water in terms of Analogue-1 production. Therefore the experiments performed in Report 5 Section A involved the use of the equivalent of 6.0 g FG in 35 ml water.

As a reference/record to the quality of the FG used throughout this report FIG. 52 shows the chromatogram obtained for 12.0 g FG mixed in 70 ml water that was obtained after 60 minutes mixing.

As a means of verification Table 20 is now compared with Table 9, both Tables previously presented herein. Visual inspection reveals that a reasonable correlation regarding the conversion of P-1 and P-2 to: Analogue-1, Analogue-2 and Analogue-4 was achieved. This provided further measure of confidence in 12.0 g FG garlic in 70 ml water providing approximately the same allinase activity to 3.0 g GP in 35 ml water.

TABLE 26

FG (6.0 g) + P-1 (400 mg) + P-2 (300 mg) - in 70 ml Water

Equivalent to: FG (3.0 g) + P-1 (200 mg) + P-2 (150 mg) - in 35 ml Water

| Reaction Time min | A-1 Concentration ppm | A-2 Concentration ppm | A-4 Concentration Integration Value × $10^{-4}$ |
|---|---|---|---|
| 60 | 1381 | 748 | 231 |
| 120 | 1518 | 860 | 243 |
| 180 | 1609 | 966 | 268 |
| 240 | 1658 | 1000 | 273 |

TABLE 9

(for comparison).

GP (3.0 g) + P-1 (200 mg) + P-2 (150 mg) - in 35 ml Water

| Reaction Time min | A-1 Concentration ppm | A-2 Concentration ppm | A-4 Concentration Integration Value × $10^{-4}$ |
|---|---|---|---|
| 60 | 2215 | 968 | 433 |
| 120 | 2465 | 1002 | 506 |
| 180 | 2597 | 998 | 551 |
| 240 | 2570 | 937 | 564 |

TABLE 27

FG (2.0 g) - in 70 ml Water

| Reaction Time Min | A-1 Concentration ppm | A-2 Concentration ppm | A-4 Concentration Integration Value × $10^{-4}$ |
|---|---|---|---|
| 60 | 21 | 62 | — |
| 120 | 24 | 77 | — |
| 180 | 24 | 80 | — |
| 240 | 25 | 84 | — |

TABLE 28

FG (6.0 g) - in 70 ml Water

| Reaction Time Min | A-1 Concentration ppm | A-2 Concentration ppm | A-4 Concentration Integration Value × $10^{-4}$ |
|---|---|---|---|
| 60 | 58 | 196 | — |
| 120 | 65 | 211 | — |
| 180 | 70 | 221 | — |
| 240 | 73 | 240 | — |

TABLE 29

FG (12.0 g) - in 70 ml Water

| Reaction Time Min | A-1 Concentration ppm | A-2 Concentration ppm | A-4 Concentration Integration Value × $10^{-4}$ |
|---|---|---|---|
| 60 | 102 | 393 | — |
| 120 | 105 | 378 | — |
| 180 | 113 | 426 | — |
| 240 | 110 | 391 | — |

TABLE 30

FG (24.0 g) - in 70 ml Water

| Reaction Time min | A-1 Concentration ppm | A-2 Concentration ppm | A-4 Concentration Integration Value × $10^{-4}$ |
|---|---|---|---|
| 60 | 229 | 653 | — |
| 120 | 233 | 691 | — |
| 180 | 248 | 709 | — |
| 240 | 245 | 698 | — |

TABLE 5

(for comparison). GP (3.0 g) - in 35 ml Water

| Reaction Time Min | A-1 Concentration ppm | A-2 Concentration ppm | A-4 Concentration Integration Value × $10^{-4}$ |
|---|---|---|---|
| 60 | 110 | 281 | — |
| 120 | 107 | 262 | — |
| 180 | 110 | 273 | — |
| 240 | 106 | 260 | — |

TABLE 20

FG (12.0 g) + P-1 (400 mg) + P-2 (300 mg) - in 70 ml Water
Equivalent to: FG (6.0 g) + P-1 (200 mg) + P-2 (150 mg) - in 35 ml Water

| Reaction Time min | A-1 Concentration ppm | A-2 Concentration ppm | A-4 Concentration Integration Value × $10^{-4}$ |
|---|---|---|---|
| 60 | 2103 | 1051 | 392 |
| 120 | 2349 | 1120 | 447 |
| 180 | 2437 | 1128 | 465 |
| 240 | 2408 | 1124 | 473 |

TABLE 9

(for comparison). GP (3.0 g) + P-1 (200 mg) + P-2 (150 mg) - in 35 ml Water

| Reaction Time Min | A-1 Concentration ppm | A-2 Concentration ppm | A-4 Concentration Integration Value × $10^{-4}$ |
|---|---|---|---|
| 60 | 2215 | 968 | 433 |
| 120 | 2465 | 1002 | 506 |
| 180 | 2597 | 998 | 551 |
| 240 | 2570 | 937 | 564 |

Process 6—Appendix 2

Effect of varying minced fresh garlic preparation time on the composition of liquids.

Preparation and use of minced fresh garlic used throughout this report: Only minced garlic tissue that had been forced through the perforated face of the a small domestic press was used. Larger pieces were discarded. Timing was important—the method protocol involved contacting weighed, freshly minced garlic with aqueous solutions before 2 minutes had lapsed from the time when garlic mincing had commenced.

In fact the very instant fresh garlic bulb tissue is damaged allinase immediately starts to convert both P-1 and P-2 to the various thiosulfinates. From a production perspective this may cause a potential problem in terms of quality assurance if minced fresh garlic is to be used as the source of allinase to separately contact: P-1 or P-2 or mixtures of P-1 and P-2. The potential problem relates to contact timing.

To gain an appreciation of the type of problem the use of minced fresh garlic may introduce an experiment was conducted. This involved delaying the introduction of 12.0 g FG into a solution of [400 mg P-1+400 mg P-2+70 ml] 5 minutes after the mincing had commenced. Table 31 summarises the results. Comparison of Table 31 with Table 21 reveals that the 3 minute extension to introducing the 12.0 g FG to the aqueous mixture had a dramatic effect on the concentration of Analogues produced.

No further confirmatory work was conducted in this area but the result is included to highlight a potential problem in using fresh garlic as a source of allinase. In comparison garlic powder only becomes active once it has been hydrated thus making process control a lot easier.

TABLE 31

FG (12.0 g) + P-1 (400 mg) + P-2 (400 mg)
FG - Contacted 5 minutes after mincing commenced.

| Reaction Time Min | A-1 Concentration ppm | A-2 Concentration Ppm | A-4 Concentration Integration Value × $10^{-4}$ |
|---|---|---|---|
| 60 | 2232 | 1458 | 324 |
| 120 | 2498 | 1589 | 371 |
| 180 | 2484 | 1497 | 383 |
| 240 | 2581 | 1565 | 401 |

TABLE 21

(for comparison). FG (12.0 g) + P-1 (400 mg) + P-2 (400 mg)
FG - Contacted 2 minutes after mincing commenced.

| Reaction Time min | A-1 Concentration ppm | A-2 Concentration Ppm | A-4 Concentration Integration Value × $10^{-4}$ |
|---|---|---|---|
| 60 | 1961 | 1586 | 249 |
| 120 | 2010 | 1618 | 256 |
| 180 | 1978 | 1578 | 255 |
| 240 | 2025 | 1618 | 260 |

Synthetic Procedures to Prepare Alliin and Methiin

Note both Methiin (Precursor-1 or briefly P-1) and Alliin (Precursor-2 or P-2) are commercially available but their current extremely high price precludes their purchase at the quantities required for manufacturing purposes and even an R&D program.

1. Preparation of Alliin (P-2):
This falls into two stages that involves
(i) the initial manufacture of L-deoxyalliin (S-allyl-L-cysteine) that is then
(ii) oxidized to produce alliin (S-allyl-L-cysteine sulphoxide).

The method described to produce P-1 is a modified version of that previously published by Bernhard Iberl, Georg Winkler, Bernd Muller and Karl Knobloch, in Planta Medica, Volume 56, pages 320-326, 1990.

(i) The Synthesis of L-Deoxyalliin (S-Allyl-L-Cysteine):

L-Cysteine and allyl chloride were used as the precursor for the synthesis of L-deoxyalliin. The procedure is as follows:

L-Cysteine (30.25 g—obtained from Sigma-Aldrich) was suspended in 750 ml ethanol. Whilst the suspension was stirred a solution of sodium hydroxide (35 g dissolved in 45 ml water) was added dropwise using a burette. The stirred solution was cooled to 4° C. Allyl chloride (23.5 ml—obtained from Dickma) was then slowly added dropwise during which the solution temperature was maintained at 4° C. Once all the allyl chloride was added the cooled solution was stirred for 1 hour after which time its temperature was adjusted to 25° C. and the solution was then stirred for a further 2 hours. After this period the pH of the solution was adjusted to 5.5 via the gradual addition of glacial acetic acid with the temperature maintained at 25° C. The solution was then cooled to 4° C. to complete the crystallization of L-deoxyalliin. The crude deoxyalliin was isolated via filtration with the crystals being washed with two cold 25 ml aliquots of ethanol. Purification was then achieved by dissolving the crystals in the minimum volume of 1% v/v boiling aqueous acetic acid solution. This volume of solution was then poured into a 15-fold volume amount of boiling ethanol. Recrystallisation occurred as the solution gradually cooled to room temperature and was completed by cooling at 4° C. The purified L-deoxyalliin crystals were then isolated by filtration and washed with two aliquots of 25 ml acetone. Thereafter, the L-deoxyalliin was air dried at 25° C.

(ii) The Synthesis of Alliin (S-Allyl-L-Cysteine Sulphoxide):

L-Deoxyalliin (5 g—as prepared in step (i) above) was dissolved in 25 ml water and whilst the solution was stirred 5.5 ml of 30% m/m hydrogen peroxide was added dropwise whilst the solution temperature was maintained at 25° C. The solution was stirred for 24 hours during which time the temperature was maintained at 25° C. After this period, the solvent was removed at 60° C. under vacuum using a rotary evaporator. The white residue was dissolved in the minimum volume of acetone:water:acetic acid (65:34:1 v/v) whose temperature was 45° C. with alliin crystals forming on cooling at 4° C. The alliin crystals were isolated by filtration and were washed with two 25 ml aliquots of cold acetone. Thereafter, the alliin was air dried at 25° C. and then stored at 4° C. prior to use.

2. Preparation of Methiin (P-1; S-Methyl-L-Cysteine Sulphoxide):

S-Methyl-L-cysteine (5 g—obtained from Dickma) was dissolved in 25 ml water and whilst the solution was stirred 5.5 ml of 30% m/m hydrogen peroxide was added dropwise whilst the solution temperature was maintained at 25° C. The solution was stirred for 24 hours during which time the temperature was maintained at 25° C. After this period, the solvent was removed at 60° C. under vacuum using a rotary evaporator. The white residue was dissolved in the minimum volume of acetone:water:acetic acid (65:34:1 v/v) whose temperature was 45° C. with methiin crystals forming on cooling at 4° C. The methiin crystals were isolated by filtration and were washed with two 25 ml aliquots of cold acetone. Thereafter, the methiin was air dried at 25° C. and then stored at 4° C. prior to use.

Bioassays and Half-Life Data

Half Life:

Experiments were carried out which rapidly assess the half-lives of Analogue 4 (MMTSO) and Analogue 1 (MAAM) and which show that the lives of these analogues are remarkably long. In order to accelerate the decomposition, a solution containing the compounds of interest was diluted with ethanol.

1. Initially, a solution was manufactured in accordance with process 5, table 6, row 4: 200 mg Methiin was dissolved in 35 ml water and then reacted with garlic powder for 4 hours).
2. At the end of the 4 hour reaction period a 25% aqueous ethanol solution was prepared as follows: 5 ml of the above reaction solution was mixed with 5 ml ethanol. The 10 ml solution so produced was then mixed with 10 ml water.
3. The above 20 ml of 25% aqueous ethanol solution was then filtered through a fluted filter paper.
4. Approximately 3 ml of the first filtered solution was then filtered through a membrane filter disc (0.25 micron pore rating) compatible with aqueous samples. The disc was fitted to a syringe in order to pull a sample through the membrane.
5. A 20 µl aliquot of the fine filtered 3 ml solution was then analysed by HPLC with the integrated diode-array chromatogram obtained at 240 nm being used to obtain peak integration values for Analogue-4 and Analogue-1.
6. The time at which the first sample was analysed by HPLC was considered to be time zero. Thereafter, the sealed syringe containing the remaining volume of the 3 ml 25% v/v aqueous solution of the reaction mixture (see point 1 above) was placed in an oven whose temperature was maintained at 40° C.
7. Periodically the solution stored at 40° C. was analysed by HPLC to obtain peak integration values for Analogue-4 and Analogue-1.

Treatment of Data

Initial concentrations of A1 and A4 in the 25% ethanolic solution were 161 ppm and 537 ppm respectively.

As shown in FIG. 53 and FIG. 54—separate graphs were constructed each expressing peak integration area measured at 240 nm as a function of time that the 25% aqueous ethanol dilution of the original reaction solution was stored at 40° C.

FIG. 53 Demonstrates that Analogue-1 exhibits a first order exponential decomposition profile. Its half-life is determined from the graph by interpolation (using the same s/w used to construct the graph—Micocal Origin). The half-life is the time at which the integrated peak area obtained for Analogue-1 provided half the value of that obtained in the chromatogram obtained at time zero. The half-life of Analogue-1, of 38 hours, is shorter than that previously disclosed—this is due to the fact its concentration was higher than in the solutions previously used. It is well known that more concentrated solutions of thiosulfinates decompose more rapidly.

FIG. 54 demonstrates that Analogue-4 exhibits a more linear decomposition profile. Its half-life again is determined by interpolation using the s/w used to construct the graph and can be seen to be very long indeed—179.7 hours under these conditions.

FIG. 55 shows the chromatogram obtained for the 25% aqueous ethanol solution of the diluted reaction mixture at time zero and FIG. 56 shows the chromatogram obtained for the 25% aqueous ethanol solution 263.5 hours after being stored at 40° C. The significant difference in retention times for Analogue-1 and Analogue-4 in the two chromatograms is probably due to a change of pre-columns during analysis times. Also for the chromatogram shown in FIG. 54—probably the column not having been equilibrated for sufficient time with the mobile phase prior to sample injection. The results are potentially very significant from a commercial perspective.

Analogue-4 provides a significantly longer half-life than Analogue-1, even when stored in 25% aqueous ethanol solution at 40° C. Until the ease of manufacture of Analogue-4 was discovered it was thought that Analogue-1 was the thiosulfinate providing longest half-life.

This half-life data obtained so far for A-4 compared to A-1 coupled with the bioassay result set out below suggests that apart from the initial target of successful MAAM (analogue-1) synthesis, analogue-4 may provide considerable potential commercial interest in its own right.

Similar studies were conducted with an aqueous solution of analogue 4 (MMTSO) produced by the method of process 6a, as set out in row 4 of table 23.
1. The reaction mixture (12.0 g FG+400 mg P-1+70 ml $H_2O$) was filtered immediately after 4 hour reaction time and served as the stock solution for this study.
2. The filtered solution was divided into 2 portions. One to be stored frozen and the other to be stored at 40° C.

40° C. was selected as it had been previously determined that A4 was likely to be substantially more stable than A1 and for comparative purposes whilst decomposing A4 as quickly as possible 40° C. was selected.
3. The portion of filtered solution to be used to determine the half-life of A4 was placed in a sealed glass bottle that was placed in an oven that provided a stable temperature of 40° C.
4. At irregular intervals a sample of the aqueous solution was withdrawn and analysed by HPLC.

FIGS. 57-60 show the chromatogram obtained after 0, 120, 168 and 672 hours respectively. Their concentrations are set out below in table 32:

TABLE 32

| Number of hours aged at 40° C. | A4 Peak Integration Value × $10^{-4}$ | A1 concentration (ppm) | A2 concentration (ppm) |
|---|---|---|---|
| 0 | 1153 (=2410 ppm) | 843 | 47 |
| 120 | 1074 | 415 | — |
| 168 | 1004 | 314 | — |
| 672 | 764 | 35 | — |

This data shows clearly that A4 deteriorates more slowly than either A1 or A2.

Bioassay:

The activity of powders and liquids was determined using standard agar diffusion tests. Susceptibility of isolates by measuring the zones of inhibition around a measured amount of the anti-microbial agent.

Materials and Methods

Bacteria: MRSA clinical isolate QMUL301 was used. Overnight broth cultures in isosensitest broth were prepared. These were diluted to give a final concentration of $10^5$ cfu/ml Media: Isosensitest agar (Oxoid Ltd).

Method:
A broth containing $10^5$ cfu/ml was prepared in peptone water.

0.2 ml was spread over each isosensitest plate.

Plates were air dried and a 6 mm well cut in the centre of the plate.

A volume of 100 ul of liquid or 100 ug of solid was added to each well.

Plates were incubated overnight at 37° C.

The presence of zones of inhibition around a well is indicative of biological activity being present. No zone around the 6 mm well, (as with the negative control) represented no biological activity.

The aqueous solutions discussed immediately above (produced by the method of process 6a, as set out in row 4 of table 23) were used in a bioassay study. Two solutions were assayed in triplicate (1) "Blue Spot"—a control solution that was frozen at −20° C. immediately after preparation and had concentrations as set out in row 1 of table 22 and (2) "Red Spot"—identical solution to Blue Spot but with this portion being stored at 40° C. for 672 hrs, such that the concentrations of thiosulfinates are as set out in table 33 below.

The samples of Blue Spot (frozen control) and Red Spot (40° C. aged) solutions were tested for antimicrobial activity using Agar plates inoculated with the super-bug MRSA as set out above. The results are set out below in tables 33 and 34.

TABLE 33

| | R&D Samples | | | | |
|---|---|---|---|---|---|
| Spot Colour | A-1 ppm | A-2 ppm | A-4 ppm | Bioassay Zone | Comment |
| Red | 35 ppm | — | 1597 ppm (743) | 35.3 mm | A portion of "Blue Spot" - stored at 40° C. for 672 hours. IN VIEW OF WARM STORAGE - THIS IS AN OUTSTANDING BIOASSAY RESULT |
| Blue | 843 ppm | 47 ppm | 2410 ppm (1153) | 39.3 mm | Control to "Red Spot" - stored frozen at −20° C. after manufacture. |

Values in parentheses - A-4 Peak Integration Value (at 240 nm) × $10^{-4}$

TABLE 34

Full Bioassay Results - Given as diameters (mm) of observed bioactivity.

| Sample | Analysis 1 | Analysis 2 | Analysis 3 | Average (mm) |
|---|---|---|---|---|
| Red Spot - Stored 40° C. | 35.0 | 35.0 | 36.0 | 35.3 |
| Blue Spot - Stored −20° C. | 40.0 | 40.0 | 39.0 | 39.3 |

Test Bacteria Culture: MRSA inoculated Agar plates

Conclusions:

1. A-4 demonstrates significant antimicrobial activity—this is confirmed by the bioassay result obtained for "Red Spot". After storage at 40° C. 672 hrs the A-1 content in the aqueous "Red Spot" solution had decayed to a very low value i.e. from 843 ppm to 35 ppm.

2. Based upon the results above there is little doubt that A-4 provides very significant potential to provide potent antimicrobial activity in aqueous solution for relatively very long periods compared with other aqueous solutions containing other *allium* derived thiosulfinates, in particular when compared to either A-1 or A-2. As the bioassay results establish, A-4 aqueous solutions remain bioactive for relatively long periods even when stored at warm temperatures.

3. Since A-4 only occurs at relatively very low levels in aqueous extracts prepared from fresh garlic tissue (typically less than 50-95 ppm resulting in a very small HPLC peak) its literature reference in such preparations is largely confined to a very small chromatographic peak identity statement. As demonstrated for the first time, only when an aqueous solution of methiin is contacted with allinase derived from either fresh *allium* species tissue or dry powdered *allium* species tissue, specifically fresh or dried garlic tissue is A-4 produced in very high quantity at manufactured concentrations that can be controlled using a semi-synthetic method (synthetic methiin contacted with a natural biosource of allinase).

Further Bioassays were carried out on solutions produced by the alternative methods disclosed herein.

Process 7

Initially a solution of MMTSO was produced by initially dissolving 1.25 g P-1 in 400 ml water, then stirring in 5.7 g Garlic Powder (McCormick Brand). The mixture was stirred for 3 hr at 21° C. The mixture was filtered and analysed by HPLC. Approx. 325 ml of the frozen filtered liquid was then used for bioassay studies. The Process 8:

A solution of Allicin was prepared by initially dissolving 1.25 g P-2 in 400 ml water then stirring in 5.7 g Garlic Powder (McCormick Brand). The mixture was stirred for 3 hr at 21° C. The mixture was filtered and analysed by HPLC. Approx. 325 ml of the frozen filtered liquid used for bioassay studies.

Control

A control solution was also produced by stirring 5.7 g or Garlic Powder in 400 ml water for 3 hours at 21° C.

FIG. 61 shows a chromatogram of the process 7, MMTSO liquid; FIG. 62 shows the chromatogram of the process 8, allicin liquid; and FIG. 63 shows the chromatogram of the control liquid. From these chromatograms, table 35 (below) can be constructed, showing the concentrations of the solutions obtained.

TABLE 35

HPLC Analysis - Results

| Liquid-Type | A-1 ppm | A-2 ppm | A-4 ppm | Total ppm |
|---|---|---|---|---|
| Control | 14 | 39 | — | 53 |
| P-1 (325 ml) | 157 | — | 925 | 1082 |
| P-2 (325 ml) | 27 | 1318 | — | 1345 |

A 925 ppm A-4 solution equates to a 8.4 × 10$^{-3}$ mole A-4 solution.
A 1318 ppm A-2 solution equates to a 8.14 × 10$^{-3}$ mole A-2 solution.
In other words in terms of molarity the A-4 concentration and A-2 concentration in the P-1 and P-2 solutions are approximately equal i.e. approximately the same numbers of molecules of A-4 and A-2 in respective aqueous solutions.

Evaluation of the Process 7 and Process 8 Liquids

Two 25 ml aliquots of the process 7 (table 26, row 2) liquid were measured into ×2 sample bottles and sealed.

Likewise, two 25 ml aliquots of the process 8 (table 26 row 3) liquid were measured into ×2 sample bottles and sealed.

One bottle of Process 7 (MMTSO) liquid and one bottle of Process 8 (Allicin) liquid were stored in freezer at −20° C.

One bottle of Process 7 (MMTSO) liquid and one bottle of Process 8 (Allicin) liquid were allowed to stand for 8 weeks at 17° C., a stable room like temperature. Shaken daily.

At the end of the storage time—all 4 bottles containing −20° C. and 17° C. stored samples tested by bioassay according to the protocol set out above. The results are set out in table 36 below.

TABLE 36

Bioassay results.

| Solution | Analysis #1 | Analysis #2 | Analysis #3 | Average* |
|---|---|---|---|---|
| Process 7 liquid - frozen | 38 | 35 | 35 | 36 |
| Process 8 liquid - frozen | 32 | 34 | 33 | 33 |
| Process 7 liquid - stored at 17° for 56 days | 28 | 29 | 28 | 28 |
| Process 8 liquid - stored at 17° for 56 days | 0 | 0 | 0 | 0 |

The average diameter values are based upon the inhibition zones measured in mm.

Where the solutions have been stored frozen at −20° C., they are high in initial A-4 and A-2 concentrations respectively (see Table 26). On the other hand where solutions have been stored at 17° C. for 56 days, the process 7 liquid had a high initial A-4 concentration whereas the process 8 liquid had a high initial A-2 concentration. However, whereas the solution of A-4 (MMTSO) remains active, the solution of A-2 (Allicin) has lost all measurable activity.

Conclusions:

1. These bioassay results are clear—A-4 (MMTSO) provides at least the same level of antimicrobial activity against MRSA as A-2 (Allicin) when the bioassay is performed using fresh A-4 and A-2 solutions with almost identical molarity values see footnote to Table 35.

2. A-4 (MMTSO) is considerably more stable than A-2 (Allicin) in aqueous solution thus providing very potent antimicrobial activity at 17° C. for very long time periods compared to A-2—namely allicin whose antimicrobial activity has been the subject of many scientific reports now spanning several decades.

3. These bioassay results correlate with the half-life data trends for A-4 and A-2 as determined using HPLC.
4. A-4 is only present in aqueous extracts of natural crushed/minced garlic at very low levels (typically less than 50-95 ppm), hitherto not making it an obvious major naturally occurring candidate for process development and commercial exploitation.

Yet further studies were carried out storing liquids prepared from garlic powder and alliin or methiin at high temperatures another liquid composed of a mixture of a liquid formed from GP+alliin, a liquid formed from GP+methiin and a liquid formed from GP+alliin and methiin was also tested.

Method
1. Aqueous solutions were prepared using 70 ml water and 6 g McCormick garlic powder, along with methiin or alliin in the proportions shown in table 37 below. The liquid in the top row was prepared from a blend of the following liquids:
Blend:
Liquid prepared from: [400 mg P-1+400 mg P-2+6 g GP+70 ml Water]—2 parts volume
Liquid prepared from: [400 mg P-1+6 g GP+70 ml Water]—3 parts volume
Liquid prepared from: [400 mg P-2+6 g GP+70 ml Water]—1 part volume 2. All solutions were prepared at a temperature of 21° C. with the garlic powder reaction mixture being stirred for 3 hours. At the end of the 3 hour stirred reaction period, the solutions were filtered and immediately assayed by HPLC for their respective A-1, A-2 and A-4 content. These initial concentration values were considered as Time Zero values.
3. After Time Zero thiosulfinate concentrations had been obtained, the solutions were stored at stable temperatures within accurate temperature regulated ovens. The temperatures are shown in table 37 above.
4. Samples of each temperature stored aqueous solution were withdrawn at appropriate time intervals and assayed by HPLC for A-1, A-2 and A-4 content. The decay of the blended liquid can be seen in FIGS. 64, 65 and 66. FIG. 64 shows the time zero results (Chromatographic peak integral values measured at 240 nm as shown are considered to represent 100% Relative Thiosulfinate Concentration Values) with: A-4 Retention Time at 2.532 min; A-1 Retention Time at 5.036 min; and A-2 Retention Time at 13.420 min.
5. The decomposition profile graphs for MMTSO, MA-AM and Allicin are shown in FIGS. 67, 68 and 69 respectively. These figures were constructed by expressing their respective HPLC peak area integration values measured at 240 nm as a function of sample storage time to obtain Relative % Concentration values. In all cases the best fit was obtained with MicroCal Origin s/w using a first order exponential decay fit. In FIG. 67, the half-life value was obtained by interpolating the time at which the A-4 (MMTSO) peak provides ½ integral value of that initially obtained for A-4 peak at Time Zero. Half-life for A-4 at 55° C. was determined as 51.1 hrs. Similarly in FIG. 68, the half-life value was obtained by interpolating the time at which A-1 (MA-AM) peak provides ½ integral value of that initially obtained for A-1 peak at Time Zero. Half-life for A-1 was determined as 30.2 hrs. Once again, the half-life value was obtained by interpolating the time at which A-2 (Allicin) peak provides ½ integral value of that initially obtained for A-2 peak at Time Zero. Half-life for A-2 is determined as 9.4 hrs.

The same methods were used to obtain the other data in table 37, the half-life of A-4 (MMTSO) in the liquids formed from 400 mg of methiin and 6 g of garlic powder, stored at 45° C. A-4 had a very long half-life of 345.9 hours, while at 40° C. A-4, its half-life was extremely long, 824.9 hours (about 5 weeks). This indicates a very long half-life is obtained from these mixtures formed from garlic powder and methiin.

TABLE 37

Table 1. Half-Life Data Obtained For Thiosulfinates Stored in Pure Water Solutions at Various Temperatures.

| Temperature | Constituents added to 70 ml Water | A-1 Half-Life hrs | A-2 Half-Life hrs | A-4 Half-Life hrs |
|---|---|---|---|---|
| 55° C. | Blend$^a$ - of x3 liquids | 30.2 (1433) | 9.4 (1228) | 51.1 (1083) |
| 45° C. | 400 mg P-1 + 6 g GP | 53.3 (867) | — (trace level) | 345.9 (2158) |
| 45° C. | 400 mg P-2 + 6 g GP | 40.5 (160) | 24 (3166) | — (not detected) |
| 40° C. | 400 mg P-1 + 6 g GP | 94 (858) | — (trace level) | 824.9 (2173) |
| 40° C. | 400 mg P-2 + 6 g GP | 85.6 (167) | 36.2 (3430) | — (not detected) |

Values shown in parentheses are initial thiosulfinate concentration expressed in ppm.

The following conclusions can be drawn from the data shown in table 37 and discussed above:
1. As illustrated in FIG. 67, MMTSO provides a first order exponential decomposition profile when stored in aqueous solution at 55° C.
2. A-4 (MMTSO) provides a significantly longer half-life than either A-1 (MAAM) or A-2 (Allicin).
3. In this study a storage temperature of 55° C. was used to rapidly to confirm that A-4 provides a first order exponential decay profile; in practice liquids will rarely be subjected to such high temperatures.
4. Although MAAM (A-1), Allicin (A-2) and MMTSO (A-4) all provide first order exponential decay profiles—at 55° C. there appears to be little difference in relative half-life values at this storage temperature for A-1 and A-4. The difference in half-life values between A-1 and A-4 becomes very significant at lower normal temperatures, particularly the types of ambient temperature ranges in which these products are used.
5. Inspection of the half-life values shown for MAAM, A-1 at 40° C. and 45° C. shown in Table 1—tend to indicate that MAAM (A-1) is more stable in the presence of MMTSO (A-4) rather than Allicin (A-2).

It may be noted that some values for the MMTSO (A-4) concentration are given in ppm whilst others use the raw A-4 peak integration values×$10^{-4}$ values. These can be converted as follows:
(A-4 Peak Integration Value×$10^{-4}$)×$10^4$×2.09=A-4 concentration in ppm.
By way of 2 types of relevant examples:
for Table 6. GP (3.0 g)+P-1 (200 mg) the A-4 values in ppm would be:
At 60 min A-4 was: (932×$10^4$)×$10^4$×2.09=1948 ppm
At 120 min A-4 was: (1104×$10^{-4}$)×$10^4$×2.09=2307 ppm
At 180 min A-4 was: (1118×$10^{-4}$)×$10^4$×2.09=2337 ppm
At 240 min A-4 was: (1163×$10^{-4}$)×$10^4$×2.09=2431 ppm
By way of a second relevant type of example the A-4 concentration for the A-4 peak whose peak integral is shown in FIG. 64 is:

$$(518×10^{-4})×10^4×2.09=1083 \text{ ppm}$$

Any embodiment described herein or in the appended claims may be combined with any one or more other embodiment(s) disclosed herein or in the claims. Such combinations can form yet further embodiment or further define one or more features or ranges of (numerical) values or parameters of the embodiments previously described and/or claimed.

INDUSTRIAL APPLICABILITY

The methods described above for preparing solutions of useful thiosulfinates may be carried out by manufacturers for sale of such liquids, or use of the liquids. Moreover manufacturers may provide kits incorporating the raw ingredients in appropriate ratios such that users may make solutions containing thiosulfinates at their leisure. Kits intended for the methods using garlic powder are particularly suitable for this application and containers comprising appropriate ratios of garlic powder and methiin and/or alliin can be supplied to users. Such powder kits would avoid sending large consignments of bulk liquid to customers around the world as is currently done to supply allicin. This would have cost advantages and would also allow shipments to be sent to hot countries without refrigeration.

By sending kits of powder, it would enable the end user to make the amount of liquid they require for immediate use, without wastage and without the need for cold storage.

Once the powder kits have been made into a liquid, their uses are manifold and have a global application in several industries, as follows:
1. Arboriculture—trees may be injected with the liquid to treat, for example, Chestnut Canker, Leaf Minor.
2. Agriculture/Horticulture—flowers and plants may be sprayed to treat pestilence and disease eg black fly
3. Agriculture—the liquids may be used to treat chickens and horses, for example.
4. Healthcare/Hospitals—treatment of disease, especially in hot countries where cold storage may be an issue. Kits do not require cold storage and would have cost advantages.

What is claimed is:

1. A method of treating an infection caused by methicillin-resistant *staphylococcus aureus* comprising administering methyl methyl-thiosulfinate to a subject in need thereof.

2. The method according to claim 1, wherein the methyl methyl-thiosulfinate is present in a solution.

3. The method according to claim 2, wherein said solution of methyl methyl-thiosulfinate has a concentration of greater than 200 ppm.

4. The method according to claim 3, wherein said solution of methyl methyl-thiosulfinate has a concentration of greater than 1000 ppm.

5. The method of claim 2, wherein said solution is an aqueous alcoholic solution.

6. A method of treating an infection caused by methicillin-resistant *Staphylococcus aureus* comprising administering an aqueous solution of methyl methyl-thiosulfinate to a subject in need thereof.

7. A method of treating an infection caused by methicillin-resistant *Staphylococcus aureus* comprising administering pharmaceutical composition comprising methyl methyl-thiosulfinate as an active ingredient to a patient in need thereof.

* * * * *